United States Patent
Lindhout et al.

(10) Patent No.: US 10,524,436 B2
(45) Date of Patent: Jan. 7, 2020

(54) HYBRID SEED POTATO BREEDING

(75) Inventors: Willem Hendrik Lindhout, Wageningen (NL); Teunis Philippus Schotte, Hazerswoude-Dorp (NL); Richard Gerardus Franciscus Visser, Bennekom (NL); Herman Johannes van Eck, Wageningen (NL); Ronaldus Cornelis Bernardus Hutten, Rhenen (NL)

(73) Assignee: AGVENTURE B.V., Diepenveen (NL)

( * ) Notice: Subject to any disclaimer, the term of this patent is extended or adjusted under 35 U.S.C. 154(b) by 418 days.

(21) Appl. No.: 13/504,156

(22) PCT Filed: Oct. 26, 2010

(86) PCT No.: PCT/NL2010/050716
§ 371 (c)(1),
(2), (4) Date: Jul. 10, 2012

(87) PCT Pub. No.: WO2011/053135
PCT Pub. Date: May 5, 2011

(65) Prior Publication Data
US 2012/0284852 A1    Nov. 8, 2012

Related U.S. Application Data

(60) Provisional application No. 61/254,980, filed on Oct. 26, 2009.

(30) Foreign Application Priority Data

Oct. 26, 2009    (EP) .................................... 09013474

(51) Int. Cl.
*A01H 5/04*    (2018.01)
*A01H 6/82*    (2018.01)

(52) U.S. Cl.
CPC .............. *A01H 5/04* (2013.01); *A01H 6/827* (2018.05)

(58) Field of Classification Search
None
See application file for complete search history.

(56) References Cited

U.S. PATENT DOCUMENTS

2014/0115736 A1    4/2014 Lindhout et al.

FOREIGN PATENT DOCUMENTS

| CA | 1289094 | 9/1991 |
|---|---|---|
| EP | 0913081 A1 | 5/1999 |
| EP | 0913081 A1 * | 6/1999 |
| WO | 2011-053135 A2 | 5/2011 |

OTHER PUBLICATIONS

Watanable et al., Breed Sci 46:329-36 (1996).*
Hermundstad & Peloquin, Potato Res 29:289-97 (1986).*
Juan Pablo Raimondi et al., Euphytica 132(3):287-95 (2003).*
Dinu et al., Int'l J Plant Breed Res 110(3):403-15 (2003).*
Visker et al., Euphytica 137(3):311-23 (2004).*
Bani-Aameur et al., Euphytica 68(3):169-79 (1993).*
Jansky, Adv Potato Chem & Tech, ed. J. Singh & L. Kaur, pp. 27-62 (2009).*
Spooner et al., Bot Rev 80:283-383 (2014).*
Veilleux, Sol CAP News 3(2):4 (2011).*
Phumichai et al., Genome 48:977-84 (2005).*
Simmonds, Potato Res 40:191-214 (1997).*
Lippman & Zamir, Trends Genet 23(2):61-66 (2006).*
Spooner et al., Bot Rev 80:283-383 (2014) (Year: 2014).*
Veilleux, Sol CAP News 3(2):4-4 (2011) (Year: 2011).*
Phumichai et al., Genome 48:977-94 (2005) (Year: 2006).*
Phumichai et al., Euphytica 148:227-34 (2006) (Year: 2006).*
Lindhout et al., Potato Res 54:301-12 (2011).*
Watanabe et al., Breed Sci 46:329-36 (1996).*
Uijtewaal et al., Euphytica 36: 745-53 (1987).*
EP 2 493 286 A2, Remarks to EPO (Dec. 21, 2012).*
Bairu et al., Plant Growth Regul 63:147-73 (2011).*
Merriam-Webster, "as", accessed Dec. 2, 2016.*
Mullins et al., Trends Plant Sci 11(5):254-60 (2006).*
Jansky et al., Crop Sci. 56:1412-22 (2016).*
Wang & Ran (NZ J Crop Hort Sci 28:1-8 (2000)).*
Phumichai et al., Euphytica 148:227-34 (2006).*
Maris, Euphytica 46:15-33 (1990).*
Hosaka & Hanneman, Jr., Euphytica 99:191-97 (1998).*
Bradshaw et al., Potato Res 49:49-65 (2006).*
Phumichai et al. (2005) Genome 48:977-94.*
Phumichai et al. (2006) Euphytica 148:227-34.*
J Jansky, "Breeding, Genetics, and Cultivar Development," Advances in Potato Chemistry and Technology, ed. J. Singh & L. Kaur, pp. 27-62 (Jun. 2009).*
Colon et al. (1995) Theor Appl Genet 90:691-98.*
Hosaka & Hanneman, Jr. (1998) Euphytica 99:191-97.*
De Jong & Rowe (1971) Potato Res 14:74-83.*
Lippman & Zamir, Trends Genet 23(2):61-66.*
Bradshaw et al. (2006) Potato Res 49:49-65.*
International Search Report relating to corresponding PCT/NL2010/050716, dated Jun. 8, 2011.
International Preliminary Report on Patentability relating to corresponding PCT/NL2010/050716, dated Apr. 26, 2012.
Bani-Aameur, et al., "Enhancement of Diploid Solanum Chacoense Bitt. Using Adapted Clones of Solanum Phureja Juz. & Buk.," Euphytica, 68: 169-179, 1993.
Buso, et al., "Tuber Yield and Quality of 4x-2x (FDR) Potato Progenies Derived from the Wild Diploid Species *Solanum berthaultii* and *Solanum tarijense*," Plant Breeding, 122, 229-232 (2003).

(Continued)

*Primary Examiner* — Russell T Boggs
(74) *Attorney, Agent, or Firm* — Dentons US LLP

(57) ABSTRACT

The present invention relates to diploid, fertile, self-compatible and essentially homozygous potato lines, wherein said lines comprise an agronomically desirable trait such as vigour. The invention further relates to methods for producing such plants and to hybrid seeds obtained by crossing such homozygous potato lines and to potato plants grown from said seed.

19 Claims, 11 Drawing Sheets

Specification includes a Sequence Listing.

(56) References Cited

OTHER PUBLICATIONS

DeMaine, M. J., "The Effects of Inbreeding on the Parental Values of Potato Dihaploids," Ann. Appl. Biol. (1995) 127: 151-156.
Dinu, et al., "Novel Inter-Series Hybrids in Solanum, Section Petota," Theor Appl Genet (2005) 110: 403-415.
Eijlander, et al., "Selection of Vigorous and Fertile S-homo- and Heterozygous Tester Clones From Self-Incompatible Diploid Potato, *Solanum tuberosum* L.," Euphytica, 97: 97-111, 1997.
Hermsen, et al., "Inheritance of Genetic Markers From Two Potato Dihaploids and Their Respective Parent Cultivars," Euphytica, 27 (1978) 681-688.
Hermundstad, et al., "Tuber Yield and Tuber Traits of Haploid-Wild Species F1 Hybrids," Potato Research 29 (1986) 289-297.
Hosaka, et al., "Genetics of Self-Compatibility Wild Diploid Potato Species *Solanum chacoense*. 1. Detection of an S Locus Inhibitor (Sli) Gene," Euphytica, 99: 191-197, 1998.
Jansky, S., "Overcoming Hybridization Barriers in Potato," Plant Breeding, 125, 1-12 (2006).
Maris, B., "Comparison of Diploid and Tetraploid Potato Families Derived from Solanum Phureja x Dihaploid S. Tuberosum Hybrids and Their Vegetatively Doubled Counterparts," Euphytica, 46: 15-33, 1990.
Pablo, et al., "Crossability Relationships Among the Wild Diploid Potato Species *Solanum kurtzianum*, S. Chacoense and S. Ruiz-Lealii from Argentina," Euphytica, 132: 2987-295, 2003.
Phumichai, et al., "Toward the Development of Highly Homozygous Diploid Potato Lines Using the Self-Compatability Controlling Sli Gene," Genome, 48: 977-984 (2005).
Simmonds, N. W., "A Review of Potato Propagation by Means of Seed, as Distinct from Clonal Propagation by Tubers," Potato Research, 40 (1997) 191-214.
Visker, et al., "Correlation Between Late Blight Resistance and Foliage Maturity Type in Potato," Euphytica, 137: 311-323, 2004.
Wang, et al., "Improving Main Agronomic Characters of Dihaploids with 2n Gametes by Means of Sexual Hybridisation and Another Culture of Potato (*Solanum tuberosum*)," New Zealand Journal of Crop and Horticultural Science, 2000, vol. 28: 1-8.
Watanabe et al., "Generation of Pest Resistant. Diploid Potato Germplasm with Short-Day Adaptation from Diverse Genetic Stocks," Breeding Science, 46: 329-336 (1996).
Uijtewaal, et al., "Morphology and Vigour of Monohaploid Potato Clones, Their Corresponding Homozygous Diploids and Tetraploids and Their Heterozygous Diploid Parent", Euphytica, Apr. 10, 1987, pp. 745-753, v. 36.
Krantz, "Potato Breeding Methods", Technical Bulletin 25, Dec. 1924, pp. 1-32, The University of Minnesota Department of Agriculture, University Farm, St. Paul.
Jackson, et al., "Inbreeding and True Potato Seed Production", Innovative Methods for Propagating Potatoes, Report of the XXVIII Planning Conference, Dec. 10-14, 1984, pp. 169-179, International Potato Center (CIP), Lima, Peru.
Birhman, et al., "Production of Inbred Progenies of Diploid Potatoes Using an S-locus Inhibitor (Sli) Gene, and Their Characterization", Genome, (2000) pp. 495-502, v. 43.
Hougas, et al., "The Potential of Potato Haplois in Breeding and Genetic Research", Am. Potato Journal, 1958, v. 35, pp. 701-707.
Haynes, "The Use of Cultivated Diploid *Solanum* Species in Potato Breeding", Prospects for the Potato in the Developing World, Symposium held at Lima, Peru, Jul. 17-19, 1972, pp. 101-110.
Jacobsen, et al., "The Influence and Possible Recombination of Genotypes on the Production of Microspore Embryoids in Anther Cultures of Solanum Tuberosum and Dihaploid Hybrids", Theor. Appl. Genet., 1978, pp. 119-123, v. 52.
Bachem, "Unravelling the Potato Genome", Retrieved from the Internet: http://www.fao.org/potato-2008/en/perspectives/bachem.html, International year of the potato (2008).
Simko, et al., "Assessment of Linkage Disequilibrium in Potato Genome with Single Nucleotide Polymorphism Markers", Genetics, Aug. 2006, pp. 2237-2245, v. 173.
Bradshaw, "New and Modern Methods of Potato Breeding", Chapter 8, pp. 157-177 (2007).
Phumichai et al., "Cryptic Improvement for Fertility by Continuous Selfing of Diploid Potatoes using Sli Gene," Euphytica, 149: pp. 251-258 (2006).
Phumichai et al., "Expression of S-locus Inhibitor Gene (Sli) in Various Diploid Potatoes," Euphytica, 148: pp. 227-234 (2006).
The International Search Report from corresponding PCT/NL2012/050269, dated Sep. 19, 2012.
Trofimov et al., Translated Title: "Utilizing Diploid Varieties and Dihaploids to Intensify Potato Selection and How to Better Preserve the Viability of the Pollen of Various Species of Gourds", Translated Journal Title: Potatoes and Vegetables 6 (2007) (English translation).
Trofimov et al., "Ispol'zovaniye Diploidnykh Vidov I Digaploidov Dlya Intensifikatsii Selektsii Kartofelya and Kak Lushche Sokhranit' Zhiznesposobnost' Pylytsy Raznykh Vidov Tykvy", Kartofel' I Ovoshchi 6 (2007) (Russian).
International Search Report relating to PCT/NL2012/050269, dated Sep. 19, 2012.
Johnstone, Jr., Francis E. "Chromosome Doubling in Potatoes Induced by Colchicine Treatment," American Journal of Potato Research, vol. 16, No. 11, pp. 288-304, Nov. 1, 1939.
Ramulu, K. Sree, H. A. Verhoeven, and P. Dijkhuis. "Mitotic blocking, micronucleation, and chromosome doubling by oryzalin, amiprophos-methyl, and colchicine in potato." Protoplasma, vol. 160, No. 2-3, pp. 65-71, Jun. 1, 1991.
Stokstad, "The New Potato: Breeders seek a breakthrough to help farmers facing an uncertain future," Science, vol. 363, Issue 6427, pp. 574-577, Feb. 8, 2019.
Birhman, R.K. and K. Hosaka, "Production of inbred progenies of diploid potatoes using an S-locus inhibitor (Sli) gene, and their characterization," Genome 43: 495-502 (2000).
Jansky, S.H., et al., "M6: A Diploid Potato Inbred Line for Use in Breeding and Genetics Research," J. Plant Registrations (Feb. 21, 2014).
Hanneman; "Self Fertility in Solanum," Am Potato J 62: 428-429 (1985).
Hosaka, K. and R.E. Hanneman, Jr., "Genetics of self-compatibility in a self-incompatable wild diploid potato species *Solanum chacoense*. 2. Localization of an S locus inhibitor (Sli) gene on the potato genome using DNA markers," Euphhytica 103:265-271 (1998).

* cited by examiner

SEQUENCE LISTING

<160> NUMBER OF SEQ ID NOS: 100

<210> SEQ ID NO 1
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: S is C or G

<400> SEQUENCE: 1
acctggtgca ggcctscgta ttgatacgat t                           31

<210> SEQ ID NO 2
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 2
gactgtgatt cgaaaygttt acctatctct t                          31

<210> SEQ ID NO 3
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 3
tcgtagaaat gacatytggg gtgctagaga t                          31

<210> SEQ ID NO 4
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 4
agtttccagc tgatgytatt ctaggagacg a                          31

<210> SEQ ID NO 5
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 5
agaggctctt gaggcrcagc gaaaagagga a                          31

<210> SEQ ID NO 6
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 6
tggtgacgtt catgtyggac gtaatgcttc t                          31

<210> SEQ ID NO 7
<211> LENGTH: 31
<212> TYPE: DNA
<213> ORGANISM: Solanum tuberosum
<220> FEATURE:
<221> NAME/KEY: misc
<222> LOCATION: (16)..(16)

<223> OTHER INFORMATION: M is A or C

<400> SEQUENCE: 7
agtatctccg tccgamtcac agtcctactc t                                31

<210> SEQ ID NO 8
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 8
ggtgctaaga ttcgcrttga tgattcacta g                                31

<210> SEQ ID NO 9
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 9
ccaacactgg aaaaaytatg gaagcagaaa g                                31

<210> SEQ ID NO 10
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 10
gctagcatta gagctygcta agcgactcaa t                                31

<210> SEQ ID NO 11
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 11
gccttggagt aagagrtttt ctgttttggg c                                31

<210> SEQ ID NO 12
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 12
ggatgttcat caacgycgac ttcgacaagc t                                31

<210> SEQ ID NO 13
<211> LENGTH: 31

```
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 13
acaacctgca agagcyttgc atctgtttag t                                  31

<210> SEQ ID NO 14
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 14
tacaatcatg atcctyttgc ctaattgccc t                                  31

<210> SEQ ID NO 15
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 15
ctgagctagt agatcratca aacggtgctc c                                  31

<210> SEQ ID NO 16
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: K is T or G

<400> SEQUENCE: 16
gactgtatgg acagtkattg ggtcagagga c                                  31

<210> SEQ ID NO 17
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 17
aagatgacgt ggagtycggc actgcgccgt t                                  31

<210> SEQ ID NO 18
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 18
```
gccgcacaag gtgctygccg tcgatgttag c                31

<210> SEQ ID NO 19
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 19
aggtagtgtt gcaaayacaa ttagagggtt g                31

<210> SEQ ID NO 20
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 20
aagtacattt atgagragat taacaagtgt t                31

<210> SEQ ID NO 21
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 21
actgctggaa ctgagytgaa caatgctatt a                31

<210> SEQ ID NO 22
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 22
gagtgccggc agcgtyacag atccgacgat g                31

<210> SEQ ID NO 23
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 23
tatggcagag aaagaratgg agtatagagt g                31

<210> SEQ ID NO 24
<211> LENGTH: 31
<212> TYPE: DNA
<213> ORGANISM: Solanum tuberosum
<220> FEATURE:
<221> NAME/KEY: msic
<222> LOCATION: (16)..(16)
<223> OTHER INFORMATION: S is C or G

<400> SEQUENCE: 24
taaactccaa catatsaaca caaattagtg c                              31

<210> SEQ ID NO 25
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 25
ttctacatcc ttcgcrggca tttttgagga g                              31

<210> SEQ ID NO 26
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is C or T

<400> SEQUENCE: 26
tttggggagg aacacytgtg ctttagaact c                              31

<210> SEQ ID NO 27
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: M is C or A

<400> SEQUENCE: 27
tgtcactaag aaagcmcaag aggcaatgca g                              31

<210> SEQ ID NO 28
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: K is T or G

<400> SEQUENCE: 28
gcaagctact tgttckaaag gacctgctac t                              31

<210> SEQ ID NO 29
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: K is T or G

<400> SEQUENCE: 29
agcgagtttg gatgckgagc ttttgcagtt a                              31

<210> SEQ ID NO 30

-continued

<210> SEQ ID NO 30
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 30
tacaaagttc actgcygagg aggtcatgca g                                  31

<210> SEQ ID NO 31
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: M is C or A

<400> SEQUENCE: 31
gatgaggaaa ggcacmggcg gaggtgttgg a                                  31

<210> SEQ ID NO 32
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is C or T

<400> SEQUENCE: 32
caccaccgtc caaacyggtt ttgccaatcg c                                  31

<210> SEQ ID NO 33
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is C or T

<400> SEQUENCE: 33
ggtccctgag caaggyaatc aacgaattag g                                  31

<210> SEQ ID NO 34
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 34
agtctctaca aacccrtggt ttcgatcttg a                                  31

<210> SEQ ID NO 35
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 35
taatgtggtc ggcacrctga cgcttgctga t                                     31

<210> SEQ ID NO 36
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 36
agatgcattc tatgcrgaac cacaaagata t                                     31

<210> SEQ ID NO 37
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 37
ttcgtgttgc actcarcgat tcagttggat g                                     31

<210> SEQ ID NO 38
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 38
agcttgtgct aatagytgtg ctgattttct c                                     31

<210> SEQ ID NO 39
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 39
tatgcaatcc cagccracat atccgatcca t                                     31

<210> SEQ ID NO 40
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 40
tcatacttca catatrtcag agtggtctga t                                     31

<210> SEQ ID NO 41
<211> LENGTH: 31
<212> TYPE: DNA
<213> ORGANISM: Solanum tuberosum
<220> FEATURE:

```
<221> NAME/KEY: misc
<222> LOCATION: (16)..(16)
<223> OTHER INFORMATION: Y is T or C

<400> SEQUENCE: 41
agagaaaaaa gctgtygttg ttgatgacga g                              31

<210> SEQ ID NO 42
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 42
cgcgtatttc ccttaytata actcgttctc t                              31

<210> SEQ ID NO 43
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 43
ttacatatgc aatagyggtg gtgatctttta t                             31

<210> SEQ ID NO 44
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 44
gaagttgtct tacatygctc ttgactatga a                              31

<210> SEQ ID NO 45
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 45
ctatgatgca tttagytcat ggagcaaact t                              31

<210> SEQ ID NO 46
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 46
agttcctttt tctccragtt ctcagactcc g                              31
```

-continued

<210> SEQ ID NO 47
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: K is T or G

<400> SEQUENCE: 47
gaggaattga tgcgtkctga actggcacag t					31

<210> SEQ ID NO 48
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 48
atacacagga agggtraagt gcttcaaatt g					31

<210> SEQ ID NO 49
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 49
tttgaccatt ctttcrgtcc tagctaacca c					31

<210> SEQ ID NO 50
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 50
aagataagaa gaaagytaag agaaccaaga t					31

<210> SEQ ID NO 51
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 51
ggcccacttt ccacayattc aatttggtct c					31

<210> SEQ ID NO 52
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 52
tcaactcacc actggrtttt actcaaaatc a 31

<210> SEQ ID NO 53
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 53
taatatgttg tgtctrtaat ttttgggtca t 31

<210> SEQ ID NO 54
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 54
cattaaccaa ggttgyatcg ttcgagagat c 31

<210> SEQ ID NO 55
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 55
tcctttgtca ttgtaygcca tggaagaagc a 31

<210> SEQ ID NO 56
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: W is A or T

<400> SEQUENCE: 56
gctttgttta agaacwgcca gaagaagttg c 31

<210> SEQ ID NO 57
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 57
gcctacgcgg catgargatg tggatattgt t 31

<210> SEQ ID NO 58
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is C or T

<400> SEQUENCE: 58
aaagctcaaa ttaaaygacg atgttcagga a                               31

<210> SEQ ID NO 59
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is G or A

<400> SEQUENCE: 59
ggccaaccaa ttccarcgtc ttctcccaga c                               31

<210> SEQ ID NO 60
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 60
aaaaccattt ggtctygttg ataattctga g                               31

<210> SEQ ID NO 61
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is G or A

<400> SEQUENCE: 61
tacatagctc tacaarcttg gaaacatgtc a                               31

<210> SEQ ID NO 62
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: W is A or T

<400> SEQUENCE: 62
gacacaaaat tcatawtggc tgatactttg t                               31

<210> SEQ ID NO 63
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: W is A or T

<400> SEQUENCE: 63
gcaacttgtc gtcggwaaac tcgactagat t                               31

<210> SEQ ID NO 64
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: M is C or A

<400> SEQUENCE: 64
ctagaaacaa aatcamaata taagttacat a                                    31

<210> SEQ ID NO 65
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 65
gttgtttgct ttgttrtgct gacttattgt a                                    31

<210> SEQ ID NO 66
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 66
atgcttcttg gttgcygttt gtttaggctc t                                    31

<210> SEQ ID NO 67
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is C or T

<400> SEQUENCE: 67
aaatatgttg ttccaytaga aaaaagagta a                                    31

<210> SEQ ID NO 68
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 68
gtgaatactg gtatcyttcc aattgaagtc a                                    31

<210> SEQ ID NO 69
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 69
aatattcttg tagtayatat tgtctaaaat c                                              31

<210> SEQ ID NO 70
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is C or T

<400> SEQUENCE: 70
caacgatatc gagaaytatt gttctaaggg a                                              31

<210> SEQ ID NO 71
<211> LENGTH: 31
<212> TYPE: DNA
<213> ORGANISM: Solanum tuberosum
<220> FEATURE:
<221> NAME/KEY: msic
<222> LOCATION: (16)..(16)
<223> OTHER INFORMATION: R is A or G

<400> SEQUENCE: 71
gctgaaagta aagacrgtgt tcaacatctt g                                              31

<210> SEQ ID NO 72
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: K is G or T

<400> SEQUENCE: 72
catgcaattg taataktatc aatgtttgtt g                                              31

<210> SEQ ID NO 73
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is C or T

<400> SEQUENCE: 73
tgctcaagct gccaaygcta atccgcttta c                                              31

<210> SEQ ID NO 74
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 74
caagatatat gcagcrgagt cccttcgagc a                                              31

<210> SEQ ID NO 75
<211> LENGTH: 31
<212> TYPE: DNA

<213> ORGANISM: Solanum tuberosum
<220> FEATURE:
<221> NAME/KEY: misc
<222> LOCATION: (16)..(16)
<223> OTHER INFORMATION: W is T or A

<400> SEQUENCE: 75
ttatggttat ggtggwggag gttggattaa t                       31

<210> SEQ ID NO 76
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: S is G or C

<400> SEQUENCE: 76
gggagggtga aaatastcga aaacgggcaa c                       31

<210> SEQ ID NO 77
<211> LENGTH: 31
<212> TYPE: DNA
<213> ORGANISM: Solanum tuberosum
<220> FEATURE:
<221> NAME/KEY: msic
<222> LOCATION: (16)..(16)
<223> OTHER INFORMATION: R is A or G

<400> SEQUENCE: 77
gattgttatc cttccrccac ctccaacaga t                       31

<210> SEQ ID NO 78
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is G or A

<400> SEQUENCE: 78
caacttccag tcgtgrgagt ggggttaacg g                       31

<210> SEQ ID NO 79
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 79
atggtgtctc caaggracta ttacagtcac t                       31

<210> SEQ ID NO 80
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 80
aacatcgata ggactytgaa ggccgcggat g                       31

<210> SEQ ID NO 81
<211> LENGTH: 31
<212> TYPE: DNA
<213> ORGANISM: Solanum tuberosum
<220> FEATURE:
<221> NAME/KEY: msic
<222> LOCATION: (16)..(16)
<223> OTHER INFORMATION: Y is C or T

<400> SEQUENCE: 81
ctgccactgc ggctgyaggt tctgcagctg c                              31

<210> SEQ ID NO 82
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 82
tgaaatgatt ggattrtgac ccatagttta g                              31

<210> SEQ ID NO 83
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: M is A or C

<400> SEQUENCE: 83
atctctaagt tggggmaacc cataatttct a                              31

<210> SEQ ID NO 84
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: W is A or T

<400> SEQUENCE: 84
cgcttgggaa gaaccwttcg gtccagtttt g                              31

<210> SEQ ID NO 85
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is C or T

<400> SEQUENCE: 85
ccaattccga cggccytcgt cgtttcaccg c                              31

<210> SEQ ID NO 86
<211> LENGTH: 31
<212> TYPE: DNA
<213> ORGANISM: Solanum tuberosum
<220> FEATURE:
<221> NAME/KEY: misc
<222> LOCATION: (16)..(16)

<223> OTHER INFORMATION: M is C or A

<400> SEQUENCE: 86
ggtcgaccat tggggmcccg tagagggtat a              31

<210> SEQ ID NO 87
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: K is T or G

<400> SEQUENCE: 87
aaggcgaatt ccggtkcccg aaatggatct c              31

<210> SEQ ID NO 88
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is G or A

<400> SEQUENCE: 88
tcattacatc aaaatrtttt atcaatgccc a              31

<210> SEQ ID NO 89
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: W is A or T

<400> SEQUENCE: 89
tgatccattt ggtctwgacc agttcttgac a              31

<210> SEQ ID NO 90
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: W is A or T

<400> SEQUENCE: 90
tgctgtgctc cttctwttcc tcatctctca c              31

<210> SEQ ID NO 91
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: W is T or A

<400> SEQUENCE: 91
tcattctcac tctccwgctg aacaagccat t              31

<210> SEQ ID NO 92
<211> LENGTH: 31

```
<212> TYPE: DNA
<213> ORGANISM: Solanum tuberosum
<220> FEATURE:
<221> NAME/KEY: misc
<222> LOCATION: (16)..(16)
<223> OTHER INFORMATION: K is G or T

<400> SEQUENCE: 92
aaaagacaag aatctkgttc agattctcca g                              31

<210> SEQ ID NO 93
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: W is A or T

<400> SEQUENCE: 93
tggggaaaac ttaatwtgac agccaaggcg t                              31

<210> SEQ ID NO 94
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 94
ggttttgtgg actgcyaaca ctgaaagata c                              31

<210> SEQ ID NO 95
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: W is T or A

<400> SEQUENCE: 95
ttatttcaat gaagcwtctg gtggacgtta t                              31

<210> SEQ ID NO 96
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: Y is T or C

<400> SEQUENCE: 96
tctgtggttt tttcaycacc tccatcttca a                              31

<210> SEQ ID NO 97
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is A or G

<400> SEQUENCE: 97
```

```
taagattagt tctaarctta gcgcagaaga c                              31

<210> SEQ ID NO 98
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: R is G or A

<400> SEQUENCE: 98
gagctctata agtgcrcctg ttactccacc t                              31

<210> SEQ ID NO 99
<211> LENGTH: 31
<212> TYPE: DNA
<213> ORGANISM: Solanum tuberosum
<220> FEATURE:
<221> NAME/KEY: misc
<222> LOCATION: (16)..(16)
<223> OTHER INFORMATION: M is A or C

<400> SEQUENCE: 99
gggctatggt tggttmggaa aaaaggtgca a                              31

<210> SEQ ID NO 100
<211> LENGTH: 31
<212> TYPE: DNA
<213> ORGANISM: Solanum tuberosum
<220> FEATURE:
<221> NAME/KEY: msic
<222> LOCATION: (16)..(16)
<223> OTHER INFORMATION: Y is T or C

<400> SEQUENCE: 100
ggatattggg ttcgtyccat gattcgtggc a                              31
```

HYBRID SEED POTATO BREEDING

RELATED APPLICATION DATA

This application is a National Stage Application under 35 U.S.C. 371 of co-pending PCT application PCT/NL2010/050716 designating the United States and filed Oct. 26, 2010; which claims the benefit of EP patent application number 09013474.3 and filed Oct. 26, 2009 and U.S. provisional patent application No. 61/254,980 and filed Oct. 26, 2009 each of which are hereby incorporated by reference in their entireties.

FIELD OF THE INVENTION

The invention relates to the field of agriculture, in particular to new plants and processes for obtaining them. The invention also relates to methods for improving the genetic constitution of crop plants, and to plants thus obtained. The invention further relates to a method for producing hybrid seeds and to hybrid seeds thus produced and to methods of producing crops using the hybrid seeds of the invention.

BACKGROUND OF THE INVENTION

The potato (*Solanum tuberosum* L.) is an integral part of the global food system. It is the world's number one non-grain food commodity, with production reaching a record 325 million tonnes in 2007.

Unlike other major field crops, potatoes are reproduced vegetatively from other potatoes. Therefore, a part of each year's crop—ranging from 5 to 15 percent, depending on the quality of the harvested tubers—is set aside for re-use in the next planting season. Most farmers in developing countries select and store their own seed tubers. In developed countries, farmers are more likely to purchase disease-free "certified seed" from dedicated suppliers.

Seed potatoes are more difficult to produce and supply than grain or pulse seed. A seed:harvest ratio of 1:20 for potatoes is considered good, compared to 1:400 for maize or 1:10.000 for tomato. One hectare may therefore require two tonnes of seed material to maximize the yield of harvestable products, compared to 18 kg for maize. In order to break dormancy, seed potatoes should be stored for several weeks before they can be planted. The right conditions during storage such as amount of light, temperature and humidity are crucial to ensure good "seed" quality.

In addition to the poor seed:harvest ratio, seed potatoes attract and transport pests and diseases. These include (amongst others) late blight, Andean potato weevils, nematodes, tuber moths and viruses. The latter are transmitted in the field by aphids and then carried from generation to generation in the seed. Such a virus infection can decrease yields by up to 20 percent.

Seed potatoes have high transportation costs because of the great distances between the major seed production areas and the major consumer production areas and the relatively high weight of individual seed potato tubers.

To feed the growing world population now and in future, the potato industry has to keep growing to meet the needs of the consuming public. Substantial research and development efforts are devoted to the modernization of planting and harvesting of fields and processing of potatoes, and to the development of economically advantageous potato varieties. Through crossbreeding of potatoes, researchers hope to obtain potatoes with the desirable characteristics of good processing, both for fresh consumption as well as for industrial purposes, high soluble solids content, high yield, resistance to diseases and pests and adaptability to various growing areas and conditions.

The research leading to potato varieties which combine the advantageous characteristics referred to above is largely empirical. This research requires large investments of time, manpower, and money. The development of a potato cultivar can often take up to eight years or more followed by at least five years of propagation to get sufficient quantities for commercial usage. Breeding begins with careful selection of superior parents to incorporate the most important characteristics into the progeny. Since all desired traits usually do not appear in one progeny, breeding is a continuous process of selecting the best recombinants, combining favourable traits of the ancestors.

The arduous task of producing a new potato variety is best understood when understanding the genetics of potato. The commercial potato has a tetraploid genome. Diploid tubers are generally too small for important commercial applications. In addition, the tetraploid genome is extremely heterozygous, often harbouring multiple alleles per locus. It is believed that self-incompatibility, which is primarily experienced at diploid level, and inbreeding depression are responsible for the maintenance of the high genetic variability found in potato and that overdominance of heterozygous alleles (heterosis) results in vigorous plants. In a typical potato offspring obtained from a cross between two unrelated parental lines deleterious alleles may therefore contribute to either a reduced fitness in case of homozygosity or an increased vigour in case of heterozygosity. It is clear that a breeder needs large populations to maximise the chance of finding individuals that carry a relatively high number of heterozygotic loci and a low number of homozygotic loci, while also exhibiting beneficial combinations of agronomically desirable traits.

Present potato breeding techniques rely on the controlled crossing of parental clones which themselves are the result of a comprehensive pre-breeding development during which amongst others special techniques such as chromosome doubling, embryo rescue, and somatic fusion are applied in order to introduce the beneficial characteristics of for instance wild and primitive *Solanum* species into these clones. The parental material that is found suitable for further breeding after a phenotypic selection procedure is then mutually crossed and the resulting non-uniform hybrid seeds are sown in large numbers in greenhouses. From tens of thousands of individual F1 seedlings tubers are harvested and retained for the next year's planting. The next year a single "seed" tuber from each resulting seedling is planted in the field. Extreme caution must be taken to avoid the introduction of viruses and diseases since the material is only clonally (vegetatively) expanded before it is sold to individual customers years later. After the second year, samples of tubers are taken for density measurements and preliminary fry tests to determine the suitability of the tubers for commercial use. A multitude of tubers of plants which have survived the selection process to this point are then planted in the third year for a more comprehensive series of fry tests and density determinations. At the fourth-year stage of development, a diminishing number of surviving selections is grown in ever expanding numbers and plants thereof are subjected to field trials in several stages to determine their adaptability to different growing conditions. Eventually, the varieties having superior agronomical qualities are transferred to other farms and the "seed" (in the form of tubers) is increased to commercial scale. Since one "seed" tuber may generate between 6 and 20 harvested tubers this up-scaling process may take years before sufficient "seed" is produced. Generally, by this time, eight or more years of planting, harvesting and testing have been invested in attempting to develop a new and improved potato cultivar.

To reduce inbreeding depression a breeder may introduce new genes from a genetically more remote parent such as from wild and primitive species with ploidy levels ranging from diploid to hexaploid. However, when two genetically unrelated potato plants are crossed, the level of heterozygosity may be increased but simultaneously more deleterious genes are also introduced. As a consequence, a breeder will typically make additional crosses with more commercial germplasm to enrich the population for favourable alleles. All together such a multiple crossing breeding programme may take dozens of years as the selection of the favourable genotypes in each generation may already take five years. Therefore, potato breeding is currently a predominantly empirical exercise, strongly characterised by trial and error.

Potatoes and their related wild species (tuber-bearing *Solanum* species) are mostly outbreeding because self fertilisation is hampered by a gametophytic self-incompatibility system. Self-incompatibility (SI) is a general name for several genetic mechanisms in angiosperms, which prevent self-fertilization and inbreeding. In plants with SI, when a pollen grain produced in a plant reaches a stigma of the same plant or another plant with a similar genotype, the process of pollen germination, pollen tube growth, ovule fertilization, and embryo development is halted at one of its stages, and consequently no seeds are produced. Self-incompatibility is not found in tetraploid potatoes.

The provision of such self-compatible clones may facilitate the generation of selfed progenies of potato, and hence the production of (highly) homozygous potato lines. This could provide a great opportunity to the development of homozygous elite breeding lines in potato. However, to date, the development of homozygous elite lines with genetically fixed agronomically desirable traits, that would enable the production of genetically uniform hybrid potato seed, has been unsuccessful.

The provision of homozygous elite lines is hampered by unknown causes. Selfing of an occasionally encountered self-compatible clone results in a slower decrease of heterozygosity than theoretically expected. The slower decline of heterozygosity may be the result of unintentional but unavoidable selection during selfing for the heterozygous plants in the offspring that exhibit higher vigour, fertility and seed germination. It is implied that, as the heterozygosity is reduced by selfing, the fertility and vigour are also reduced and the plants may become weak and completely sterile. The situation is perhaps worsened by the establishment of homozygous configurations of recessive deleterious genes. This phenomenon which is generally referred to as inbreeding depression has greatly hampered the development for homozygous potato lines and hence the production of uniform hybrid potato seed.

There is a large prejudice against the production of homozygous breeding lines in potato due to inbreeding depression. Uijtewaal et al. (Euphytica 36 (1987) 745-753) indicated that owing to sterility problems, homozygous potato clones would be of little importance for practical breeding. Developing homozygous inbred lines was considered, but rendered impossible in potato (Umaerus, 1987, Proceeding of the 10th Triennial Conference of the European Association of Potato Research, Aalborg, Denmark, pp 72-103 as cited in Almekinders et al. 2009 Potato Research 52:275-293). Routes involving doubling of haploids have long been presumed as promising. Nontheless, up to the present day the ruling opinion is that inbreeding depression in diploid potato is too strong to ever result in vigorous homozygous plants.

Birhman and Hosaka (Genome 43: 495-502 (2000)) have suggested the possibility to utilize the Sli gene derived from *S. chacoense* for development of highly homozygous true potato seed (TPS) lines and heterosis breeding of the potato. However, to date, no homozygous lines with good agronomic traits such as good tuber yield, have ever been reported from this proposed line of research. Rather, those homozygotes that have been produced do not exhibit any agronomically relevant tuber yield.

Rommens in 2010 (Genetic modification of Plants, Kempen & Jung, eds, In: Biotechnology in Agriculture and Forestry 64(1): 61-77 (2010)), advocates the route of genetic transformation, due to the fact that efforts to improve the yield and quality of this crop are hampered by inbreeding depression.

In short, production of true breeding lines of potato is considered impossible. Due to this fact, potato breeding cannot escape the traditional schemes based on crossing of tetraploid heterozygotes. As a result, the challenge is considered formidable to combine various utilization traits (relating to fresh and processing uses), resistances to pathogens and pests, and numerous other relevant agronomic traits with improvements in yield into a commercially acceptable cultivar (Douches et al. 1999, Crop Science 36(6):1544-1552).

It is an objective of the present invention to provide means and methods for the production of elite breeding lines of potato and for the production of uniform hybrid potato seed from which plants can be grown that exhibit agronomically relevant tuber yield.

SUMMARY OF THE INVENTION

The present inventors have attempted to achieve homozygous parental breeding lines for generative propagation of potatoes via a number of routes, none of which were successful. These unsuccessful routes included androgenesis, gynogenesis, doubling of haploids and continued selfings. Only by repeated selfing of a self-compatible plant comprising the Sli gene derived from *S. chacoense* and the use of did the inventors arrive at the product of the present invention. The present invention now provides in a first aspect a diploid, fertile, self-compatible and essentially homozygous potato line comprising plants having an average tuber yield expressed in grams of fresh weight of at least 200 grams per plant. Plants having an average tuber yield expressed in grams of fresh weight of at least 200 grams per plant are in general terms also referred to herein as being vigorous.

In a preferred embodiment, said line in addition to said tuber yield comprises at least one, more preferably at least 2, 3, 4, 5 or 6 (additional) agronomically desirable traits. Preferably, said agronomically desirable traits are selected from the group consisting of insect tolerance, nematode resistance, disease resistance (including but not limited to resistance to Scab caused by *Streptomyces* spp, Powdery scab, *Rhizoctonia*, Silver scurf, *Phytophthora infestans*), herbicide tolerance, cold tolerance, drought tolerance, wet tolerance, tolerance to dry and wet rot, salinity tolerance, and cold sweetening resistance.

In another preferred embodiment of said potato line of the invention, plants of said line when mature attain an average fresh weight of the foliage and shoots of at least 500 grams per plant. Plants attaining an average fresh weight of the foliage and shoots of at least 500 grams per plant are in general terms also referred to herein as being vigorous.

In another aspect, the present invention provides a plant of a line according to the invention as described above. Preferably, said plant is diploid, fertile, self-compatible and essentially homozygous and has an average tuber yield expressed in grams of fresh weight of at least 200 grams per plant.

In another aspect, the present invention provides a seed of a plant as described above. Said seed may be homozygous (i.e. represent a selfed seed), but may also be heterozygous for the alleles where the parents differ. In one embodiment, said seed is preferably a uniform hybrid potato seed. Such uniform hybrid potato seed being the result of a cross between two homozygous, self-compatible, fertile and vigorous plants of a line according to the invention as described above, preferably of two different lines, wherein the lines contain at least 20% contrasting homozygous loci as determinable by molecular marker analysis.

In another aspect, the present invention provides a method for producing a diploid, fertile, self-compatible and essentially homozygous potato line comprising plants having an average tuber yield expressed in grams of fresh weight of at least 200 grams per plant, comprising:

(a) providing a first potato plant, which first potato plant is a plant of a first diploid, self-compatible, fertile and essentially homozygous potato line;

(b) providing a second potato plant, wherein said second potato plant is a plant of a diploid or tetraploid potato line which may have any level of homozygosity, said line of said second potato plant comprising plants having an average tuber yield expressed in grams of fresh weight of at least 200 grams per plant;

(c) cross pollinating said first and second potato plant to provide seeds and collecting said seeds to thereby provide an offspring generation in the form of a hybrid offspring seed;

(d) growing said hybrid offspring seed into a population of hybrid offspring potato plant and selecting from said population plants producing tubers at a yield expressed in grams of fresh weight of at least 200 grams per plant, and (e) selfing said hybrid offspring potato plant or backcrossing said hybrid offspring potato plant to a potato plant of said line of said first potato plant, for between 1 to 8 selfings or backcrosses, to thereby provide a diploid, self-compatible and essentially homozygous potato breeding line comprising plants having an average tuber yield expressed in grams of fresh weight of at least 200 grams per plant.

A first potato plant in a method as described herein is preferably a plant of a first diploid, self-compatible, fertile and essentially homozygous potato line, wherein the self-compatibility is conditioned by the presence of a dominant allele of an S-locus (self-incompatibility locus) inhibitor gene (Sli) that is nonallelic to the S locus as described in Hosaka and Hanneman 1998 Euphytica, 99: 191-197.

The above method, when performed on a sufficiently large scale (at least more than 10,000 plants) and performed with the use of a suitable second potato plant, which is preferably a diploid potato clone that is essentially not homozygous, said line of said second potato plant comprising plants having an average tuber yield expressed in grams of fresh weight of at least 200 grams per plant, preferably a line such as IVPAA-096-18 (D2) as described in the Examples herein below, results in the production of an essentially homozygous, fertile, vigorous and self-compatible breeding line, wherein said vigour is in particular represented by an average tuber yield expressed in grams of fresh weight of at least 200 grams per plant. The provision of such a breeding line is a crucial step in the provision of genetically homozygous true potato seed (TPS).

The first and second breeding line can subsequently be used in the production of the TPS when both the first and second breeding line comprise agronomically desirable characteristics, have good general combining abilities, and preferably have at least 20% contrasting homozygous loci as determinable by molecular marker analysis.

In a preferred embodiment of said method for producing a diploid, fertile, self-compatible and essentially homozygous potato line according to the invention, said steps a-e are repeated wherein step b comprises the provision of third (or further) potato plant wherein said third potato plant is a plant of a diploid or tetraploid potato line which may have any level of homozygosity, wherein said third potato plant is a donor for an additional agronomically desirable trait. Preferably, said trait is selected from the group consisting of insect tolerance, nematode resistance, disease resistance (including but not limited to resistance to Scab caused by *Streptomyces* spp, Powdery scab, *Rhizoctonia*, Silver scurf, *Phytophthora infestans*), herbicide tolerance, cold tolerance, drought tolerance, wet tolerance, tolerance to dry and wet rot, salinity tolerance, and cold sweetening resistance, or any other agronomically beneficial trait or desirable characteristic as defined herein.

The second or third potato plant as described above may suitably be a diploid potato clone selected from the plants D1-D21 as listed in Table 6 of Example 3 below. The skilled person will understand that other diploid potato clones may also be used. Highly preferred is the use of potato clone IVPAA-096-18 (D2) which is available from Laboratory of Plant Breeding (IVP) (Dr. Ir Ronald B. C. Hutten), Wageningen University, Droevendaalsesteeg 1, 6708 PB Wageningen, The Netherlands.

Proper (commercial) sources of tetraploid cultivars are provided through the European Cultivated Potato Database (ECPD) at www.europotato.org/menu.php and/or the Potato Pedigree Database of the expertise group Plant Breeding (a cooperation between the Laboratory of Plant breeding of Wageningen UR, the Netherlands) and the business unit Biodiversity and breeding of Plant Research International (PRI), Wageningen, the Netherlands at www.plantbreeding.wur.nl/potatopedigree/.

In another preferred embodiment of said method, said first potato plant is a plant of potato line NCIMB 41663, NCIMB 41664, NCIMB 41665, or NCIMB 41765, representative seeds of said line having been deposited with the NCIMB, Aberdeen, Scotland.

In yet another preferred embodiment of said method, said second potato plant is a plant of a second diploid, fertile, self-compatible and essentially homozygous potato line.

In yet a further preferred embodiment of said method, said second potato plant is a plant of a second diploid, fertile, self-incompatible potato line.

The method for producing a diploid potato breeding line may further comprise the steps of enhancing the breeding value of the diploid potato breeding line by intercrossing, selfing and backcrossing while continuous selecting for agronomically desirable traits. Experimental crosses are done to evaluate general combining abilities (intercrossability).

In another aspect, the present invention provides a diploid potato breeding line, more preferably an elite line, obtainable by the method of the present invention as described above.

In another aspect, the present invention provides a hybrid potato seed obtainable by crossing plants of a first and second diploid potato breeding line according to the present invention as described above, wherein said plants of said first and second diploid potato breeding line contain at least 20% contrasting homozygous loci as determinable by molecular marker analysis.

In another aspect, the present invention provides a method for producing a uniform hybrid potato seed, comprising:

(a) providing a first potato plant, which first potato plant is a plant of a first diploid, fertile, self-compatible and essentially homozygous potato line, (b) providing a second potato plant, wherein said second potato plant is a plant of a second diploid, fertile, self-compatible and essentially homozygous potato line, wherein said first and second plant contain at least 20% contrasting homozygous loci as determinable by molecular marker analysis, and (c) cross pollinating said first and second potato plant and allowing one of said parent plants to produce berries with seeds and collecting said seeds from said berries to provide an offspring generation in the form of a hybrid offspring seed.

In a preferred embodiment of a method for producing hybrid seed, said first and second potato plant are from potato lines comprising plants having an average tuber yield expressed in grams of fresh weight of at least 200 grams per plant, preferably wherein said first and second potato plant are plants having a tuber yield of at least 200 grams fresh weight per plant.

In another preferred embodiment of said method of producing hybrid seed, at least one of said first and second potato plants comprises at least one agronomically desirable trait, preferably selected from the group consisting of insect tolerance, nematode resistance, disease resistance (including but not limited to resistance to Scab caused by *Streptomyces* spp, Powdery scab, *Rhizoctonia*, Silver scurf, *Phytophthora infestans*), herbicide tolerance, cold tolerance, drought tolerance, wet tolerance, tolerance to dry and wet rot, salinity tolerance, and cold sweetening resistance.

In another preferred embodiment of a method for producing hybrid seed according to the present invention, said first potato line is a diploid, self-compatible and essentially homozygous offspring potato plant comprising the Sli-gene, preferably wherein said first potato plant is a plant of potato lines NCIMB 41663, NCIMB 41664, NCIMB 41665, or NCIMB 41765, representative seeds of said lines having been deposited with the NCIMB, Aberdeen, Scotland, or a diploid, self-compatible and essentially homozygous offspring potato plant thereof.

In another preferred embodiment of a method for producing hybrid seed according to the present invention, said second potato plant is a plant of a second diploid, self-compatible and essentially homozygous potato line preferably comprising at least two agronomically desirable traits selected from the group consisting of insect tolerance, nematode resistance, disease resistance (including but not limited to resistance to Scab caused by *Streptomyces* spp, Powdery scab, *Rhizoctonia*, Silver scurf, *Phytophthora infestans*), herbicide tolerance, cold tolerance, drought tolerance, wet tolerance, tolerance to dry and wet rot, salinity tolerance, and cold sweetening resistance.

In another aspect, the present invention provides a seed of potato lines NCIMB 41663, NCIMB 41664, NCIMB 41665, or NCIMB 41765, representative seeds of said line having been deposited with the NCIMB, Aberdeen, Scotland.

In another aspect, the present invention provides a seed produced by the method for producing a uniform hybrid potato seed as disclosed herein.

In another aspect, the present invention provides a hybrid potato plant, or part thereof, produced by growing the seed of the present invention.

In another aspect, the present invention provides pollen or an ovule of the hybrid potato plant, or part thereof, of the present invention.

In another aspect, the present invention provides a tuber from the hybrid potato plant of the present invention.

In another aspect, the present invention provides a potato plant having all of the physiological and morphological characteristics of the hybrid potato plant produced by growing the seed of the present invention.

In another aspect, the present invention provides a tissue culture of the hybrid potato plants of the present invention.

In another aspect, the present invention provides a potato plant regenerated from the tissue culture of the present invention, wherein said regenerated potato plant has all the physiological and morphological characteristics of the hybrid potato plant produced by growing the seed of the present invention.

In another aspect, the present invention provides a method for producing a hybrid potato seed wherein the method comprises crossing a first potato plant with a second potato plant and harvesting the resultant hybrid potato seed, wherein said first and/or second parent potato plant is a diploid, fertile, self-compatible and essentially homozygous plant according to the present invention that has an average tuber yield expressed in grams of fresh weight of at least 200 grams per plant.

In another aspect, the present invention provides a method of producing a hybrid potato plant, said method comprising producing a seed according to a method of the present invention and growing said seed into a potato plant.

In another aspect, the present invention provides a potato plant produced by the method of the invention, or a tuber thereof.

In another aspect, the present invention provides a method set of at least 4 intercrossable homozygous diploid, fertile, self-compatible and essentially homozygous potato lines comprising plants having an average tuber yield expressed in grams of fresh weight of at least 200 grams per plant according to the present invention, wherein each of said lines differ from another line in said set by having at least 20% contrasting homozygous loci as determinable by molecular genetic marker analysis.

The invention also provides as an embodiment of methods of the invention as described above methods comprising the steps of:

(a) providing a first potato plant, which first potato plant is a plant of a first diploid, self compatible and essentially homozygous potato line carrying chromosomes with alleles for agronomically desirable traits that are to be expressed in an offspring generations, (b) providing a second potato plant, wherein said second potato plant is a plant of a second diploid, self compatible and essentially homozygous potato line carrying chromosomes with alleles for agronomically desirable traits that are to be expressed in an offspring generations and that may be different form the traits in the said first plant, and (c) cross pollinating said first and second potato plant such that one of said parent plants produces berries with seeds and collecting said seeds from said berries to provide an offspring generation in the form of a hybrid offspring seed carrying combinations of chromosomes with said alleles.

Thus, in an alternative embodiment the plant of the first potato line may carry chromosomes with alleles for agronomically desirable traits that are to be expressed in an offspring generations, in which case the agronomically desirable trait in the plant of the second potato line may be different from the traits in the said first plant.

In another aspect, the present invention provides a method of producing a herbicide resistant, nematode resistant, insect resistant and/or disease resistant potato plant, said method comprising producing a seed according to a method of the invention described above by crossing parental lines that are herbicide resistant, nematode resistant, insect resistant and/or disease resistant and growing said seed a potato plant.

In another aspect, the present invention provides a herbicide resistant, nematode resistant, insect resistant and/or disease resistant potato plant produced by the method of the invention as described above.

In yet another aspect, the present invention provides a method for preventing transmittal of virus infections between potato generations, comprising:

(a) providing a first potato plant, which first potato plant is a plant of a first diploid, self-compatible and essentially homozygous potato line, (b) providing a second potato plant, wherein said second potato plant is a plant of a potato line that may have any level of ploidy and/or any level of homozygosity, said second potato plant carrying a chromosome with an allele for a agronomically desirable trait that is to be expressed in an offspring generation;

(c) cross pollinating said first and second potato plant such that one of said parent plants produces berries with seeds and collecting said seeds from said berries to provide an offspring generation in the form of a hybrid offspring seed carrying a chromosome with said allele;

(d) growing said hybrid offspring seed into a hybrid offspring potato plant carrying a chromosome with said allele, and (e1) harvesting tubers from said hybrid offspring potato plant to provide tubers expressing said trait, or (e2) selfing said hybrid offspring potato plant or backcrossing said hybrid offspring potato plant to a potato plant of said line of said first potato plant, thereby providing further offspring plants carrying a chromosome with said allele and wherein said offspring plants are increasingly homozygous following each backcrossing or selfing step.

In another aspect, the present invention provides a diploid, fertile, self-compatible and essentially homozygous potato line comprising plants having an average tuber yield expressed in grams of fresh weight of at least 200 grams per plant, said plant being obtainable by:

(a) providing a first potato plant, which first potato plant is a plant of a first diploid, fertile, self-compatible and essentially homozygous potato line, (b) providing a second potato plant, wherein said second potato plant is a plant of a diploid potato line having an average tuber yield expressed in grams of fresh weight of at least 200 grams per plant, (c) cross pollinating said first and second potato plant and allowing one of said parent plants to produce berries with seeds and collecting said seeds from said berries to provide an offspring generation in the form of a hybrid offspring seed, (d) growing said hybrid offspring seed into a hybrid offspring potato plant, (e) backcrossing said hybrid offspring potato plant to a potato plant of said line of said first potato plant, and selecting from the offspring plants thus generated a plant that is diploid, self-compatible and vigorous in that it produces tubers at a yield expressed in grams of fresh weight of at least 200 grams per plant, and (f) selfing said diploid, self-compatible and vigorous plant for between 1 to 8 generations while selecting for self-compatibility and vigour as defined in (e).

In another aspect, the present invention provides a hybrid potato seed which seed, when sown produces a diploid, fertile, self-compatible and essentially heterozygous potato plant having an average tuber yield expressed in grams of fresh weight of at least 200 grams per plant, said plant being obtainable by:

(a) providing a first diploid, fertile, self-compatible and essentially homozygous potato line comprising plants having an average tuber yield expressed in grams of fresh weight of at least 200 grams per plant, (b) providing a second diploid, fertile, self-compatible and essentially homozygous potato line comprising plants having an average tuber yield expressed in grams of fresh weight of at least 200 grams per plant, wherein said first and second plant contain at least 20% contrasting homozygous loci as determinable by molecular marker analysis, and (c) cross pollinating said first and second potato plant and allowing at least one of said parent plants to produce berries with seeds and collecting said seeds from said berries to provide an offspring generation in the form of a hybrid offspring seed.

The steps of selecting or providing plants that are homozygous, or the step of selecting or providing plants having at least 20% contrasting loci as defined herein above, may comprise marker assisted selection using the molecular genetic markers as provided herein.

0, Potato germplasm: The origin comprises in principle all potato genotypes within the cultivated potato species (*Solanum tuberosum*) and related crossable species;

1, Self-compatible diploid potato: Cultivated potato (*Solanum tuberosum*) is usually self incompatible. Self-compatibility is introduced from related species (see for instance Hermsen, J. G. Th. 1978, Euphytica 27, 1-11);

2, Homozygous fertile self-compatible diploid potato: Homozygous diploids can be obtained by doubling haploids (Uijtewaal et al., 1987, Theor. Appl. Genet. 73, 751-78) by anther culture (Jacobsen and Sopory, 1977, Theor. Appl. Genet. 52, 119-123), by ovule culture or by repeated selfings (Phumichai & Hosaka, 2006, Euphytica 149, 251-258). The example of the latter is illustrated herein;

3, Vigorous fertile homozygous self-compatible diploid potato: The vigour is enhanced by crossing with other diploid potato, selfing and backcrossing while selecting for higher vigour;

4, Diploid potato breeding Lines: Agronomically desirable traits are introduced by crossing with other diploid potato, selfing and backcrossing while selecting for these traits;

5, Elite diploid potato breeding Lines: The breeding value is further enhanced by intercrossing, selfing and backcrossing while continuous selecting for agronomically desirable traits. Experimental crosses are done to evaluate general combining abilities;

6 Potato hybrid cultivars: Good combining breeding lines are crossed. The seeds obtained are hybrid true potato seeds that are uniform.

Figure 2:
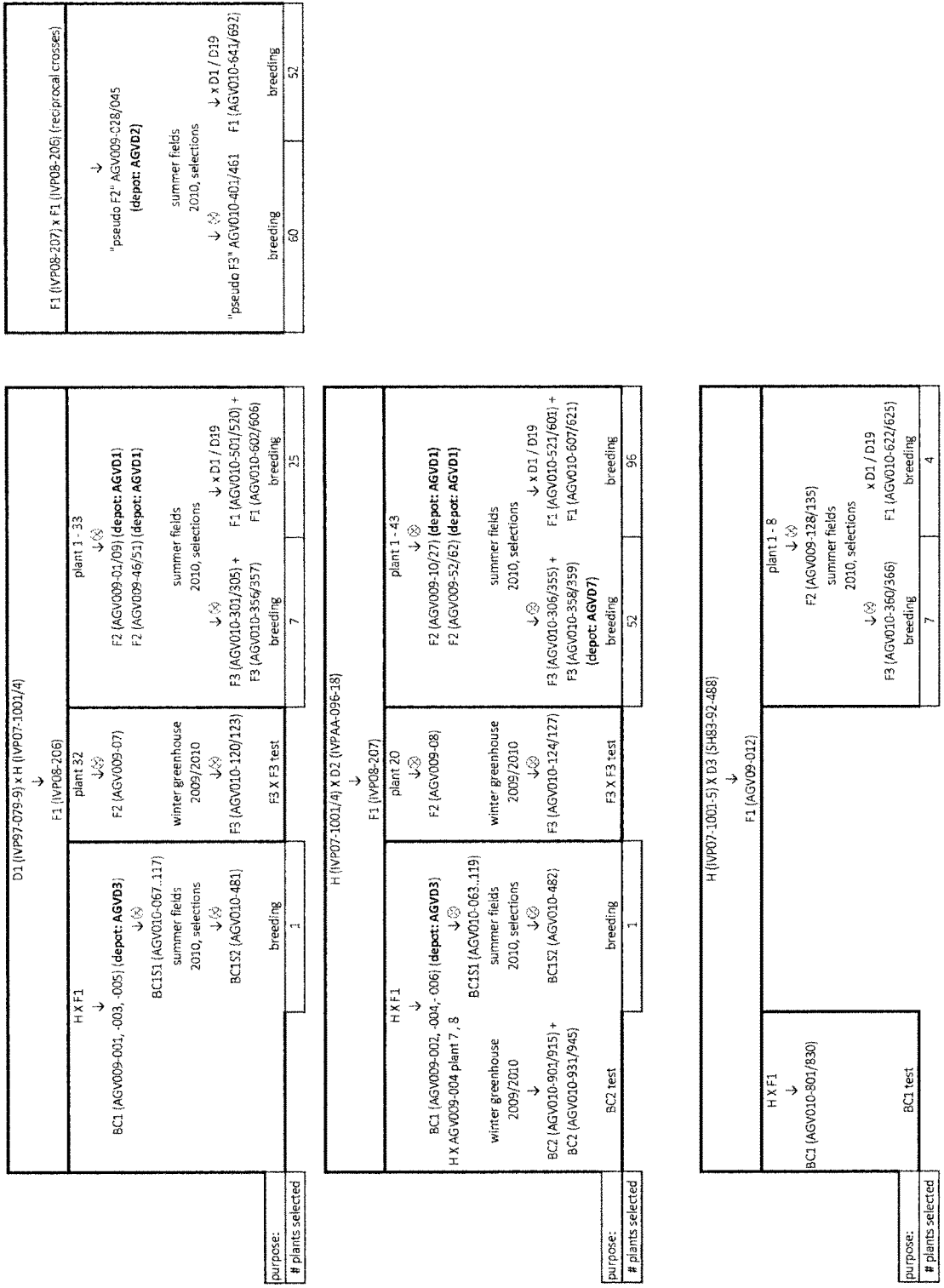

FIG. 2 shows a schematic presentation of the pedigrees of the populations, deposits and plants as described in the Examples, starting from a cross between a diploid, essentially homozygous and self-compatible potato plant ("H") and three different diploid clones (D1, D2, and D3) that are essentially non-homozygous and self-incompatible and that act as donor lines of one or more desirable agronomic traits. The production of an array of essentially homozygous lines from backcross lines to fully selfed clones, each having one or more desirable traits derived from the donor lines provides a set of elite breeding lines for the production of an array of hybrid potato cultivars in the form of hybrid seed. ⊗ Refers to selfings. As can be seen, and as detailed in the Examples, only donor line D2 resulted in the production of a large number of self-compatible plants that would show vigour as defined herein. Vigorous plants could be obtained from the other crossings as well, albeit at a much lower frequency (0.1-1%).

Figure 3:
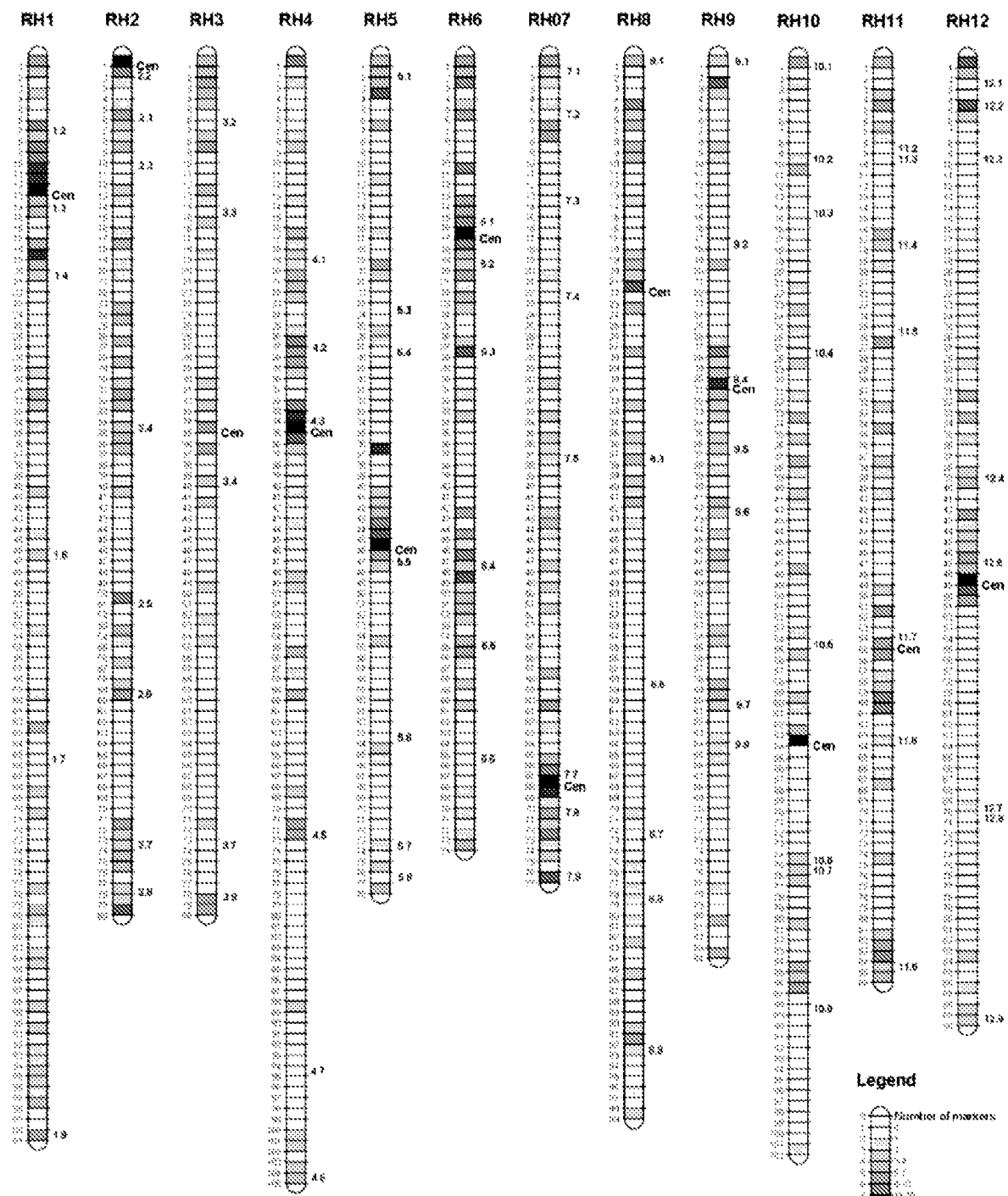

FIG. 3 displays the ultra-dense genetic linkage map of the genome of diploid breeding clone RH89-039-16. The number on the left of the linkage group indicates the cumulative number of recombination events counted from the top. The number of AFLP markers in each bin is represented by shades of grey according to the figure legend. Putative centromere positions are indicated with "Cen" alongside the chromosome (van Os et al., 2006 Genetics 173(2):1075-1087). The numbers on the right of the linkage group indicate the approximate location of the corresponding PotSNPmarker as used herein, wherein reference is made to Table 5B in Example 3, below, for marker annotations. The figure clearly indicates the distribution of informative markers over the potato genome of this clone. A similar distribution was observed for these markers with another clone used herein, clone SH83-92-488.

Figure 4:
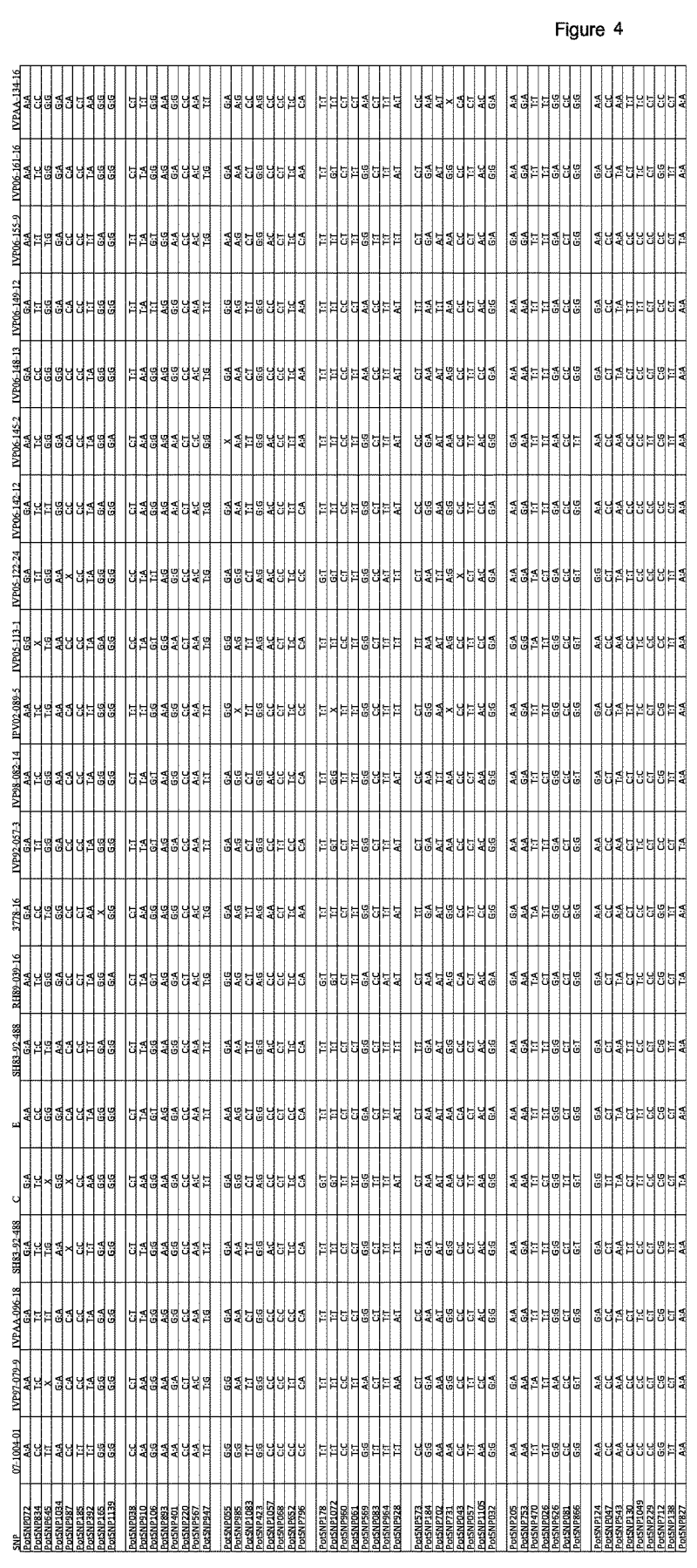
Figure 4:
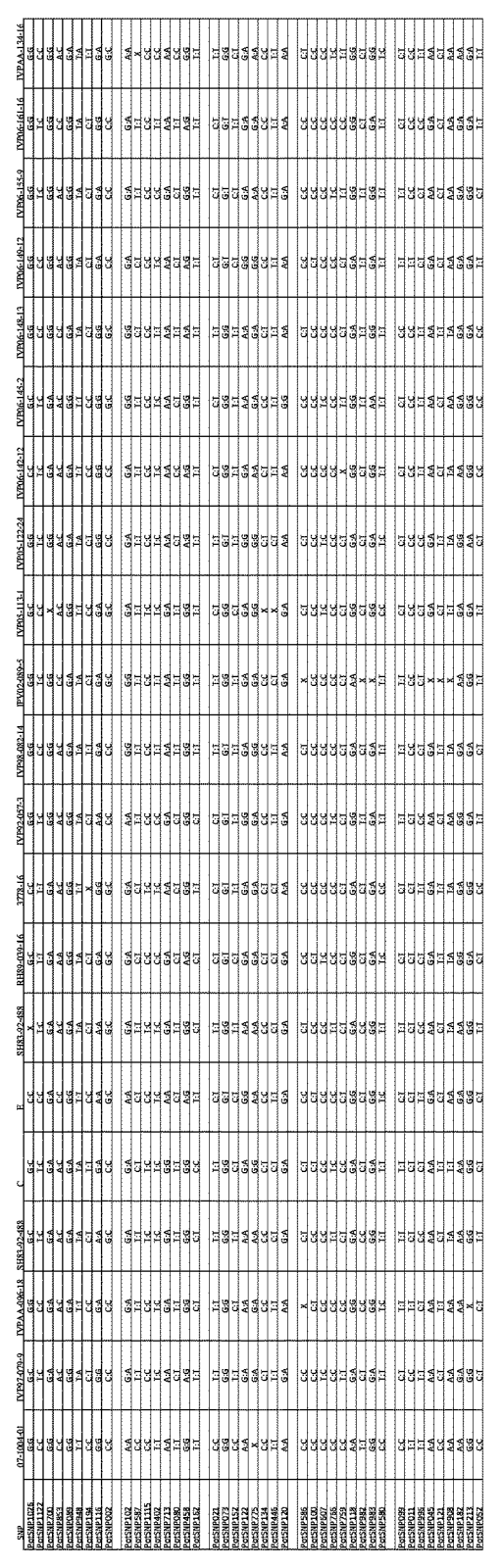

FIG. 4 shows marker data of 100 markers over 20 different diploid potato genotypes, representing the diploid potato breeding germplasm (Example 2).

Figure 5A:
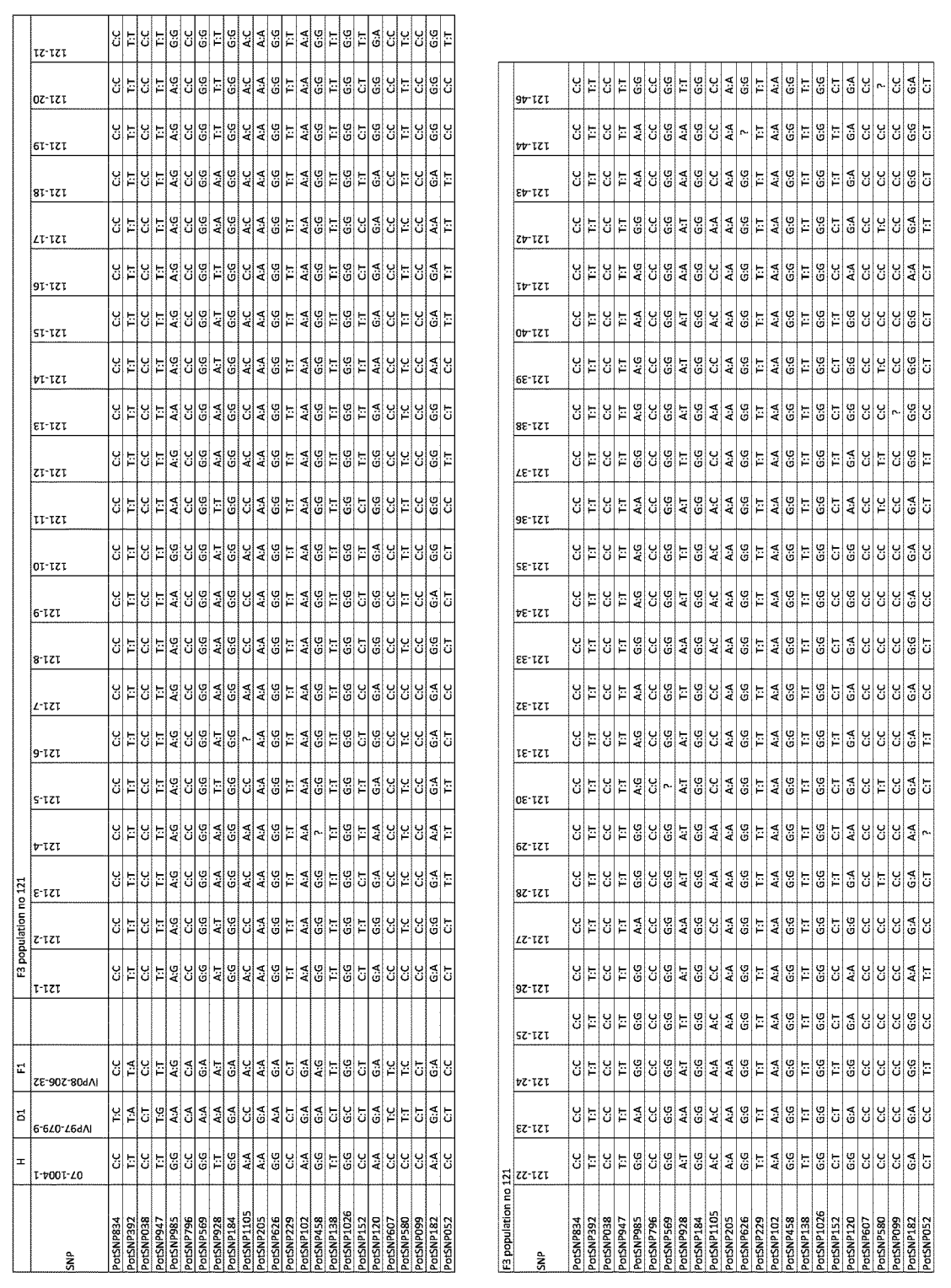
Figure 5B:
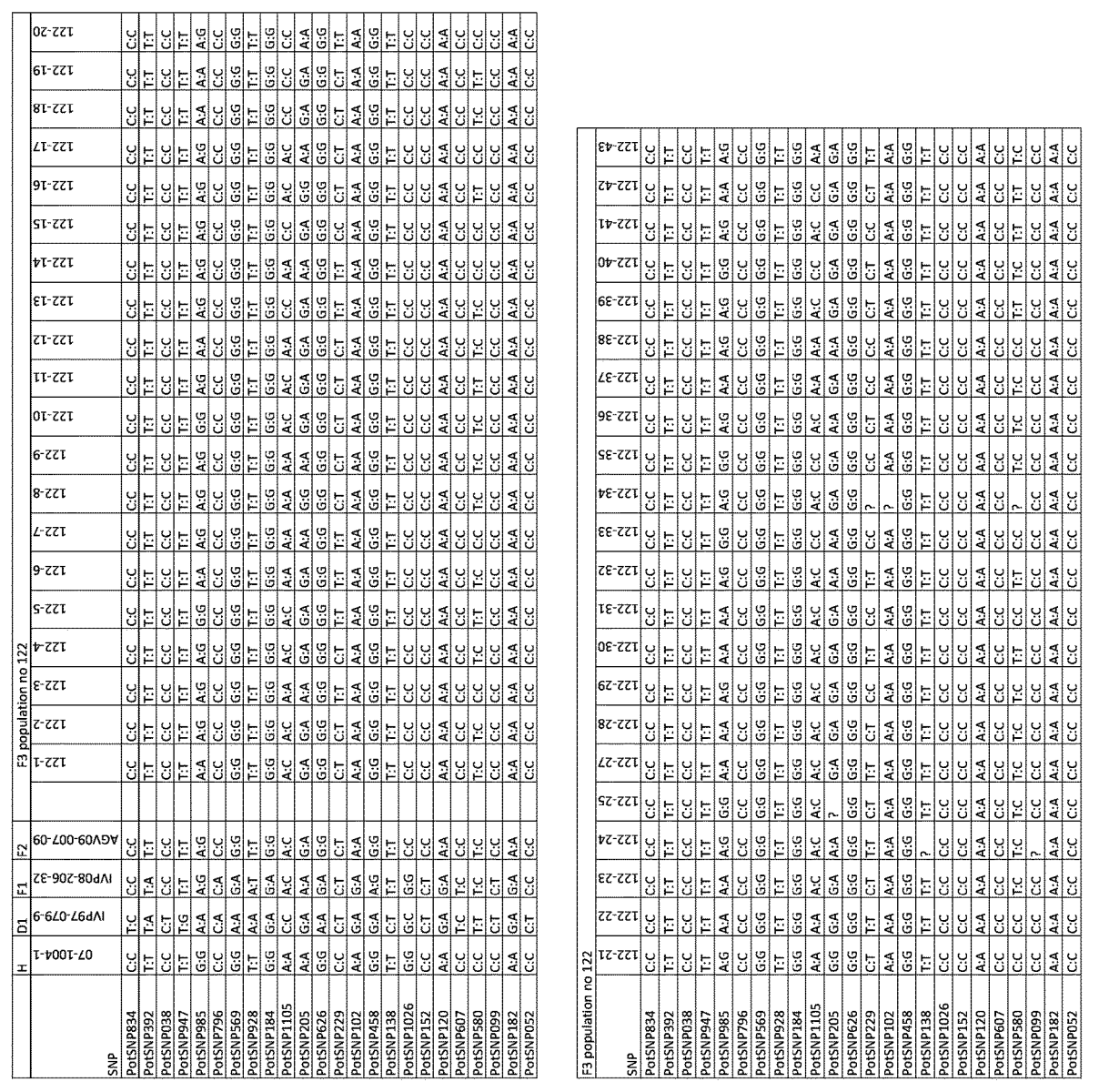
Figure 5C:
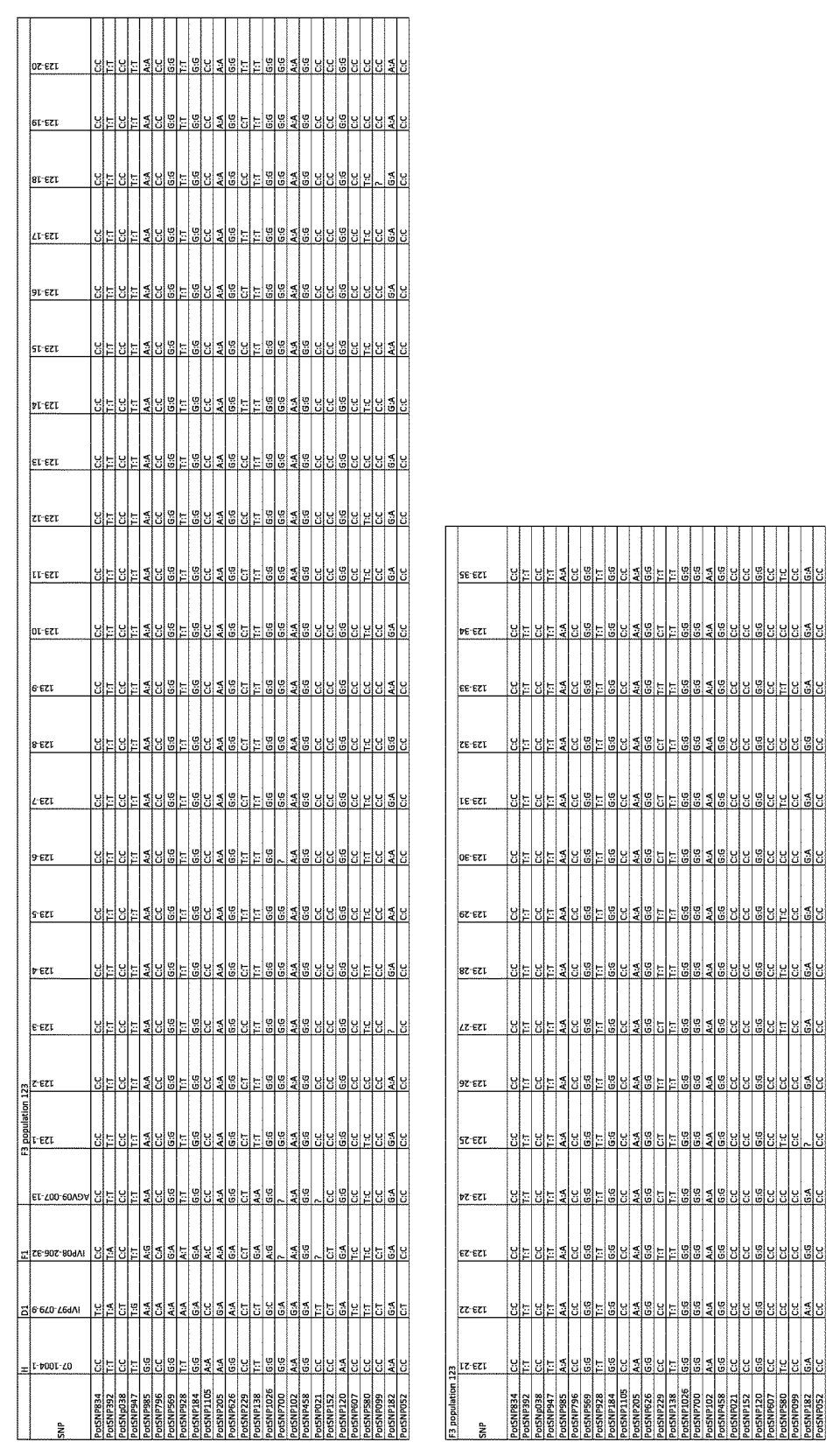
Figure 5D:
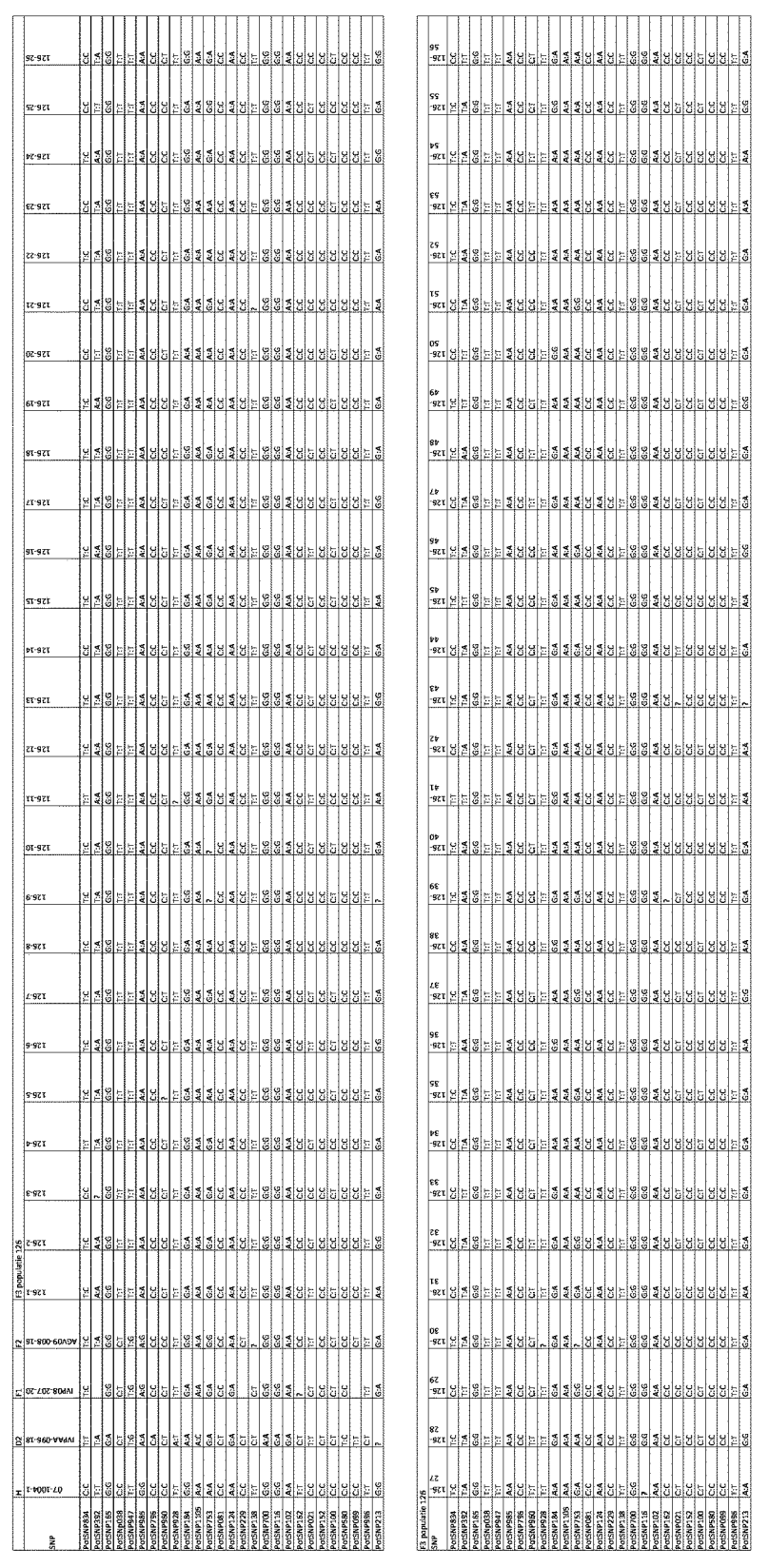
Figure 5E:
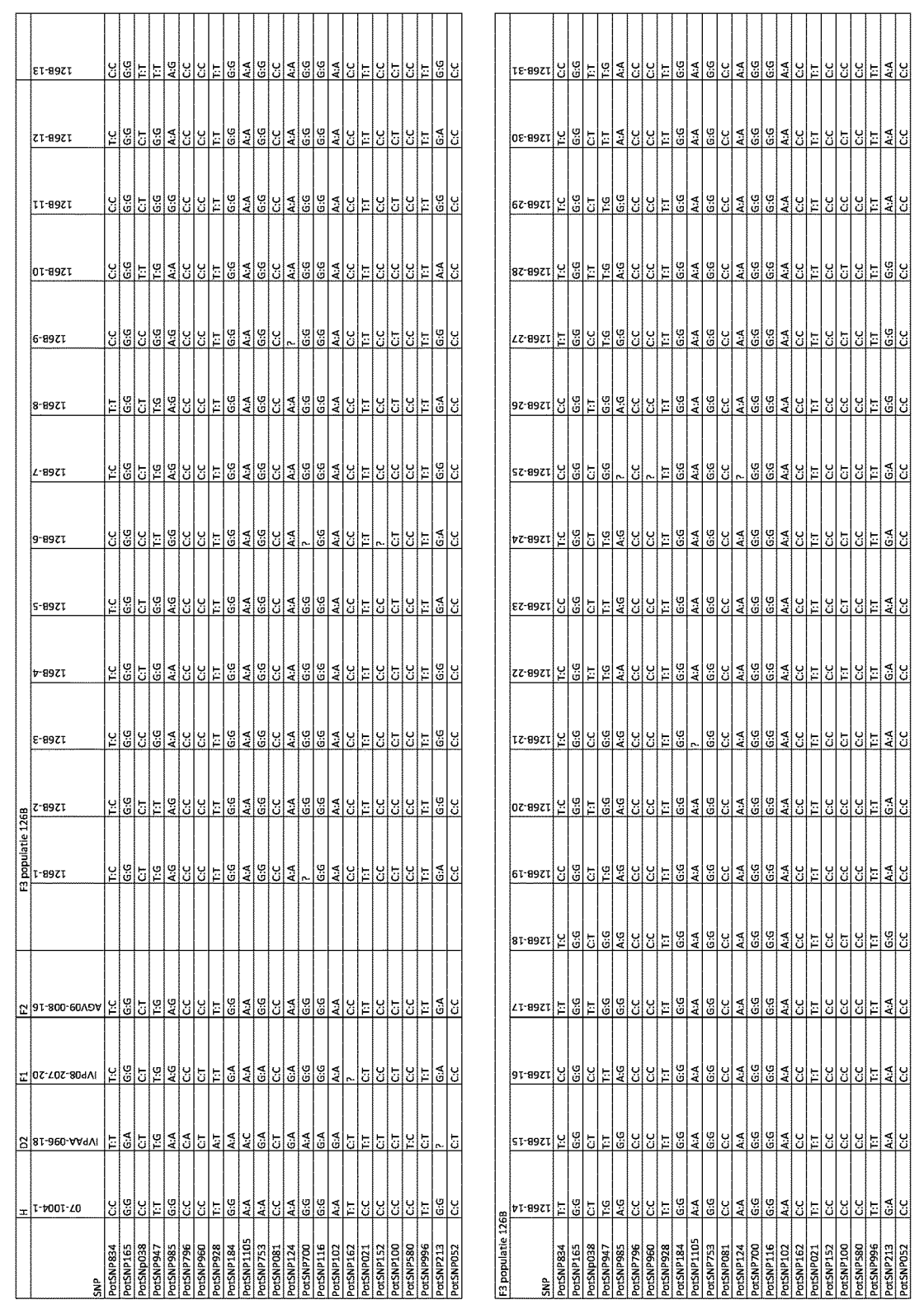
Figure 5F:
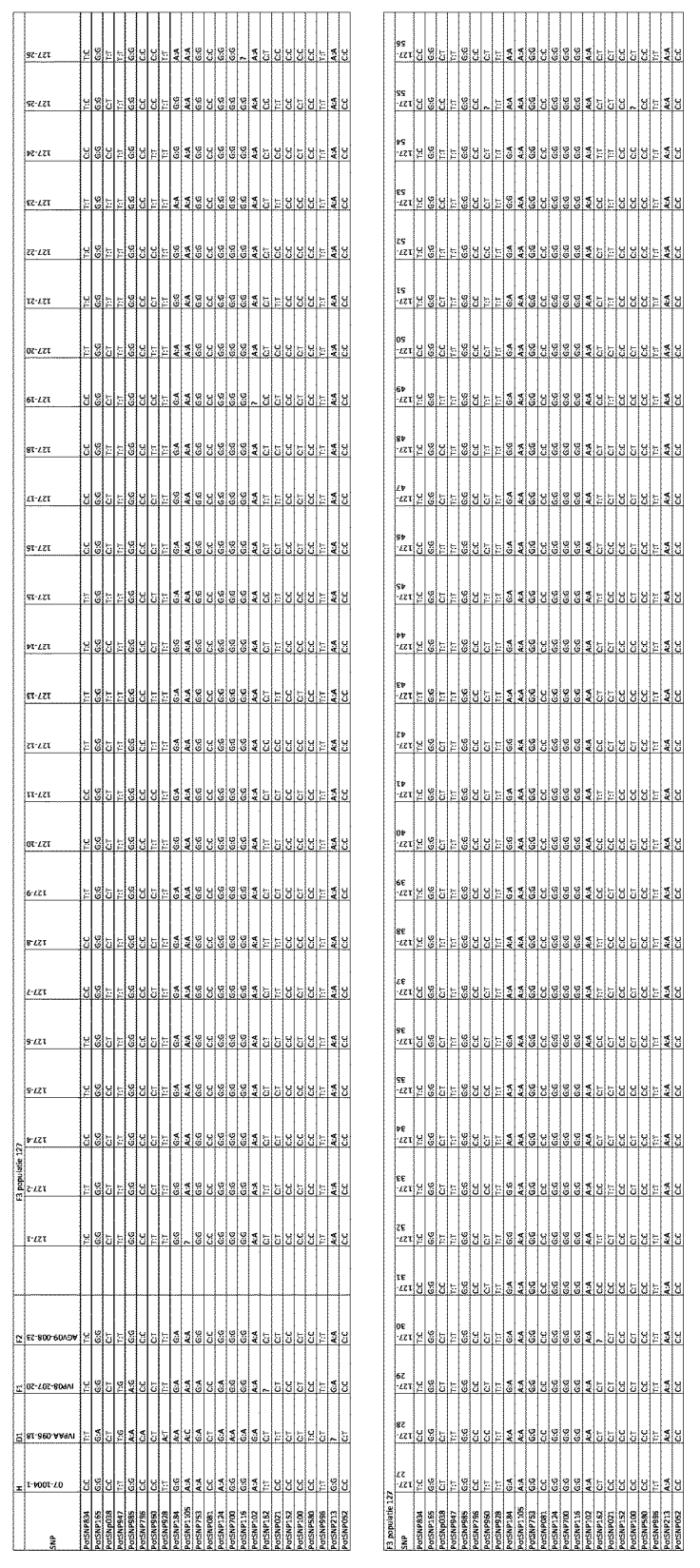

FIG. 5 shows the result of SNP marker analysis as described in Example 3 on a set of six F3 populations and their respective parents.

DETAILED DESCRIPTION OF THE INVENTION

Definitions

The term "potato" is used herein to refer to material that is essentially of species *Solanum tuberosum*, but may include introgression segments of other tuber bearing *Solanum* species such as *Solanum chacoense, Solanum phureja, Solanum andigena, Solanum demissum*.

The term "potato plant" is used herein to refer to a seedling or mature plant as grown from cell culture or seed. Persons of ordinary skill in the art will recognize that when the term "potato plant" is used in the context of the present invention, this also includes derivative varieties that retain the essential distinguishing characteristics of for instance potato varieties that are subject of the present invention, such as a Single Gene Converted plant of that variety or a transgenic derivative having one or more value-added genes incorporated therein (such as herbicide or pest resistance). Backcrossing methods can be used with the present invention to improve or introduce a characteristic into the variety.

The term "crossing" as used herein refers to the fertilization of female plants (or gametes) by male plants (or gametes). The term "gamete" refers to the haploid reproductive cell (egg or sperm) produced in plants by mitosis from a gametophyte and involved in sexual reproduction, during which two gametes of opposite sex fuse to form a diploid zygote. The term generally includes reference to a pollen (including the sperm cell) and an ovule (including the ovum). "Crossing" therefore generally refers to the fertilization of ovules of one individual with pollen from another individual, whereas "selfing" refers to the fertilization of ovules of an individual with pollen from the same individual. Crossing is widely used in plant breeding and results in a mix of genomic information between the two plants crossed one chromosome from the mother and one chromosome from the father. This will result in a new combination of genetically inherited traits. Usually, the progeny of a crossing is designated as: "F1". If the F1 is not uniform (segregates) it is usually designated as "F1 population". "Selfing" of a homozygous plant will usually result in a genetic identical plant since there is no genetic variation. "Selfing" of an F1 will result in an offspring that segregates for all traits that have heterozygotic loci in the F1. Such offspring is designated: "F2" or "F2 population"

When referring to "crossing" in the context of achieving the introgression of a genomic region or segment, the skilled person will understand that in order to achieve the introgression of only a part of a chromosome of one plant into the chromosome of another plant, it is required that random portions of the genomes of both parental lines will be recombined during the cross due to the occurrence of crossing-over events in the production of the gametes in the parent lines. Therefore, the genomes of both parents must be combined in a single cell by a cross, where after the production of gametes from said cell and their fusion in fertilization will result in an introgression event.

The term "intercrossable", as used herein, refers to the ability to yield progeny plants after making crosses between parent plants.

As used herein, the terms "introgressing", "introgress" and "introgressed" refer to both a natural and artificial process whereby individual genes or entire chromosomes are moved from one individual, species, variety or cultivar into the genome of another individual, species, variety or cultivar, by crossing those individuals, species, varieties or cultivars. In plant breeding, the process usually involves selfing or backcrossing to the recurrent parent to provide for an increasingly homozygous plant having essentially the characteristics of the recurrent parent in addition to the introgressed gene or trait.

The term "introgression" refers to the result of an introgression event.

The term "backcross" refers to the result of a "backcrossing" process wherein the plant resulting from a cross between two parental lines is (repeatedly) crossed with one of its parental lines, wherein the parental line used in the backcross is referred to as the recurrent parent. Repeated backcrossing results in replacement of genome fragments of the donor parent with those of the recurrent. The offspring of a backcross is designated "BCx" or "BCx population", where "x" stands for the number of backcrosses.

The term "backcrossing" as used herein refers to the repeated crossing of a hybrid progeny back to the recurrent parents. The parental potato plant which contributes the gene for the desired characteristic is termed the nonrecurrent or donor parent. This terminology refers to the fact that the nonrecurrent parent is used one time in the backcross protocol and therefore does not recur. The parental potato plant to which the gene or genes from the nonrecurrent parent are transferred is known as the recurrent parent as it is used for several rounds in the backcrossing protocol. In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a potato plant is obtained wherein essentially all of the desired morphological and physiological characteristics of the recurrent parent are recovered in the converted plant, in addition to the single gene or a limited number of genes transferred from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified, substituted or supplemented with the desired gene from the nonrecurrent parent, while retaining essentially all of the rest of the desired genes, and therefore the desired physiological and morphological constitution of the original variety. The choice of the particular nonrecurrent parent will depend on the purpose of the backcross. One of the major purposes is to add some commercially desirable, agronomically important traits to the recurrent parent. The exact backcrossing protocol will depend on the characteristic or trait being altered or added to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred. Preferably, such genes are monitored by diagnostic molecular markers.

Likewise, transgenes can be introduced into the plant using any of a variety of established recombinant methods well-known to persons skilled in the art.

Many single gene traits have been identified that are not regularly selected for in the development of a new variety but that can be improved by backcrossing and genetic engineering techniques. Single gene traits may or may not be transgenic, examples of these traits include but are not limited to: herbicide resistance; resistance to bacterial, fungal or viral disease; insect resistance; uniformity or increase in concentration of starch and other carbohydrates; enhanced nutritional quality; decrease in tendency of tuber to bruise; and decrease in the rate of starch conversion to sugars.

The term "selfing" refers to the process of self-fertilization wherein an individual is pollinated or fertilized with its own pollen. Repeated selfing eventually results in homozygous offspring.

A "line", as used herein, refers to a population of plants derived from a single cross, backcross or selfing. The individual offspring plants are not necessarily identical to one another. It is possible that individual offspring plants are not vigorous, fertile or self compatible due to natural variability. However, it is foreseen that suitable plants that are vigorous, fertile and self compatible can be easily identified in a line and used for additional breeding purpose.

As used herein, the term "allele(s)" means any of one or more alternative forms of a gene, all of which alleles relate to at least one trait or characteristic. In a diploid cell or organism, the two copies of a gene occupy corresponding loci on a pair of homologous chromosomes. Each copy may be a distinct allele.

A "gene" is defined herein as a hereditary unit (often indicated by a sequence of DNA) that occupies a specific location on a chromosome and that contains the genetic instruction for a contribution to potential phenotypic characteristics or trait in a plant.

A "locus" is defined herein as the position that a given gene occupies on a chromosome of a given plant species.

As used herein, the term "homozygous" means a genetic condition existing when identical alleles reside at corresponding loci on homologous chromosomes.

The term "essentially homozygous" refers to a level of homozygosity of at least 25%, preferably at least 50%, more preferably at least 75%, still more preferably at least 76, 77, 78, 79, 80, 81, 82, 83, 84, 85, 86, 87, 88, 89, 90, 91, 92, 93, 94, 95, 96, 97, 98, 99, or 100% homozygosity when testing 100, preferably 1000, more preferably at least 10,000 loci.

Homozygosity levels are average values for the population, and refer preferably to those loci wherein the parents differ.

As used herein, the term "heterozygous" means a genetic condition existing when different alleles reside at corresponding loci on homologous chromosomes.

The term "recombination" or "recombine" refers to the exchange of information between two homologous chromosomes during meiosis. In a "recombinant" plant, DNA that is originally present on a specific location within the chromosome, e.g. linked to a gene/locus, is exchanged for DNA from another plant (i.e. maternal for paternal or vice versa). In order to exchange only the required material, and maintain the valuable original information on the chromosome as much as possible, two flanking crossover or recombination events will usually be required. In a double recombinant this exchange has taken place on both sides of a gene/locus. one way to find such a double recombinant, is to screen a population of F2-plants. This population has to be large, since double recombination occurs in only a limited frequency. Alternatively, double recombinants within a genetic unit can be the result of subsequent backcrossing. The frequency of double recombination is the product of the frequencies of the single recombinants. (E.g. a recombinant in a 10 cM area can be found with a frequency of 10%, double recombinants are found with a frequency of 10%× 10%=1%).

As used herein, the term "progeny" means (a) genetic descendant(s) or offspring.

As used herein, the term "population" means a genetically heterogeneous collection of plants sharing a common genetic derivation.

A "recombination event" refers to a mitotic or meiotic crossing-over event, including a GMO event.

As used herein, the term "hybrid" means any offspring of a cross between two genetically unlike individuals, more preferably the term refers to the cross between two (elite or inbred) breeding lines which will not reproduce true to the parent from seed.

The term "segregate", as used herein, refers to the separation of paired alleles during meiosis so that members of each pair of alleles appear in different gametes. The term includes reference to the result of this genetic phenomenon wherein the offspring population of a crossing in which at least one of the parents is heterozygous for an allelic gene is non-uniform with respect to phenotypic trait conferred by said gene.

The term "breeding line", as used herein, refers to a line of a cultivated potato having commercially valuable or agronomically desirable characteristics, as opposed to wild varieties or landraces. The term includes reference to an elite breeding line or elite line, which represents an essentially homozygous, usually inbred, line of plants used to produce commercial F₁ hybrids. An elite breeding line is obtained by breeding and selection for superior agronomic performance comprising a multitude of agronomically desirable traits. An elite plant is any plant from an elite line. Superior agronomic performance refers to a desired combination of agronomically desirable traits as defined herein, wherein it is desirable that the majority, preferably all of the agronomically desirable traits are improved in the elite breeding line as compared to a non-elite breeding line. Elite breeding lines are essentially homozygous and are preferably inbred lines.

The term "elite line", as used herein, refers to any line that has resulted from breeding and selection for superior agronomic performance. An elite line preferably is a line that has multiple, preferably at least 3, 4 5, 6 or more (genes for) desirable agronomic traits as defined herein.

The terms "cultivar" and "variety" are used interchangeable herein and denote a plant with has deliberately been developed by breeding, cq crossing and selection, for the purpose of being commercialized, cq used by farmers and growers, to produce agricultural products for own consumption or for commercialization (fresh consumption, processing, feed, etc). The term "breeding germplasm" denotes a plant having a biological status other than a "wild" status, which "wild" status indicates the original non-cultivated, or natural state of a plant or accession.

The term "breeding germplasm" includes, but is not limited to, semi-natural, semi-wild, weedy, traditional cultivar, landrace, breeding material, research material, breeder's line, synthetic population, hybrid, founder stock/base population, inbred line (parent of hybrid cultivar), segregating population, mutant/genetic stock, market class and advanced/improved cultivar. Examples of cultivars include such cultivated varieties as Bintje, Russet Burbank, Eigenheimer, and Nicola.

As used herein, the terms "purebred", "pure inbred" or "inbred" are interchangeable and refer to a substantially homozygous plant or plant line obtained by repeated selfing and-or backcrossing.

As used herein, the term "molecular genetic marker" or short "marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion/deletion (INDEL) mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location.

As used herein, the term "plant part" indicates a part of the potato plant, including organelles, single cells and cell tissues such as plant cells that are intact in plants, cell clumps and tissue cultures from which potato plants can be regenerated. Examples of plant parts include, but are not limited to, single cells and tissues from pollen, ovules, leaves, embryos, roots, root tips, tubers, anthers, flowers, fruits, stems shoots, and seeds; as well as pollen, ovules, leaves, embryos, roots, root tips, anthers, flowers, fruits, stems, shoots, scions, rootstocks, seeds, tubers, protoplasts, calli, and the like.

Unless expressly stated otherwise, the term "seed", as used throughout this specification, refers to the body from which a new plant develops (or kernel in some plants) containing the small embryonic plant enclosed in a seed coat covering, usually together with some stored food. This seed, referred to as botanical or "true" seed is the product of the ripened ovule of gymnosperm and angiosperm plants which occurs after fertilization and some growth within the mother plant.

As used herein the terms "vigour" and "vigorous" refer to the relative amount of above-ground or below-ground tissues of a plant, which relative amount may be more or less independent of one another.

The relative amount of above-ground tissues can be expressed as visual observations of the amount of foliage, in terms of plant height, number of stems, number of leaves assessed on ordinal scales, and/or in terms of fresh weight or dry matter. This trait has relevance during the first period of the plant growth cycle with an average duration of 100 days of cultivation (range 75-130 days) under normal growth conditions that prevail in North Western Europe during the season from May trough to August. Under these conditions, the plants of the present invention attain a weight of the foliage and shoots (above-ground plant) expressed in grams of fresh or dry weight which is at least 50%, more preferably at least 60%, 70%, 80%, 90% or more of the (essentially heterozygous) diploid breeding clone RH89-039-16, which—in turn—has 68% (range 44-86%) of the tuber yield of tetraploid potato varieties based on nine years of testing. Clone RH89-039-16 is available for reference purpose from Dr. Ir Ronald B. C. Hutten, Laboratory of Plant Breeding, Wageningen University, Droevendaalsesteeg 1, 6708 PB Wageningen, The Netherlands.

Alternatively, or in addition, the term vigour may be used in connection with a certain minimal tuber yield. The term "tuber yield", as used herein, will generally refer to a tuber yield expressed in grams of fresh weight which at harvest in plants according to the present invention is at least 30-50%, more preferably at least 60%, 70%, 80%, 90% or more of the (essentially heterozygous) diploid breeding clone RH89-039-16, which—in turn—has 68% (range 44-86%) of the tuber yield of tetraploid potato varieties based on nine years of field testing under conditions of a 100 days cultivation period with normal growth conditions that prevail in North Western Europe during the season from May trough to August. As indicated above, clone RH89-039-16 is available for reference purpose from Dr. Ir Ronald B. C. Hutten, Laboratory of Plant Breeding, Wageningen University.

Tuber yield, unless expressly stated otherwise, is based on the tubers formed from a seedling plant, in contrast to the tubers formed from a tuber-grown plant—which yield may be 50-200% more than the yield of a seedling.

Alternatively, or in addition, the term vigour may refer to a tuber yield expressed in grams of fresh or dry weight which at harvest is at least 30-50%, more preferably at least 60%, 70%, 80%, 90% or more of the diploid breeding clone RH89-039-16. This means that the tuber yield expressed in grams of fresh weight may (in plants of the present invention, reach levels of at least 200, more preferably at least 300, 400 or 500 grams per plant grown from seed in clay soil under normal North Western European summer conditions, and even 400, 500, 600, 700, 800 or more, such as 900 or 1000 grams of fresh tuber weight or more per plant when said plant is raised from tubers and grown in clay soil under normal North Western European summer conditions.

The term "a line comprising plants", wherein said plants are indicated as having a certain characteristic, such as tuber yield, should preferably be understood as referring to a line essentially consisting of plants having the said trait, while allowing for some biological variation.

The term "diploid" as used herein refers to a plant wherein each vegetative cell contains two sets of chromosomes (2x=2n, wherein n is the number of chromosomes). One set of chromosomes is donated from each parent.

The term "tetraploid" as used herein refers to a plant wherein each vegetative cell contains four sets of chromosomes (2x=4n).

The term "nematode resistance" as used herein refers to a plant in which a functional resistance gene has been introgressed that prevents the multiplication of at least one nematode population or isolate.

The term "disease resistance" as used herein refers to the ability to show more than 50% reduction of the amount of diseased leaf surface or tuber volume, or the amount of multiplication of an insect or pathogenic microorganism including but not limited to *Streptomyces* spp, *Rhizoctonia*, Silver scurf and, *Phytophthora infestans*, The term "herbicide tolerance" as used herein refers to a plant which shows less than 50% damage of the foliage than the usual damage upon the application of a specified dosage of herbicide.

The term "cold tolerance" as used herein refers to the average amount of leaf surface of a plant which shows frost damage, which damage in cold tolerant plants is less than the average damage observed at a temp of minus 3° C. for relatively cold sensitive reference varieties such as e.g. Caribe and/or Kennebec.

The term "drought tolerance" as used herein refers to a plant which shows less than average damage at limiting water conditions as compared to relatively drought sensitive reference varieties such as Caribe and/or Carlton.

The term "flooding tolerance" as used herein refers to a 50% lower proportion of affected tubers (anaerobic degradation) relative to a plant which shows average damage at flooding The term "tolerance to wet rot" as used herein refers to a plant with the slightest level of resistance to *Erwinia* species (currently termed *Pectobacterium* spp.).

The term "tolerance to dry rot" as used herein refers to a plant with the slightest level of resistance to *Fusarium* species.

The term "salinity tolerance" as used herein refers to a plant which shows less damage than average at salinity conditions.

The term "growth rate" as used herein refers to the increase of plant biomass per unit of time.

The term "tuber development defects" (e.g. misshapen or damaged tubers)" as used herein refers to a plant which shows visual as well as internal malformations of tubers during plant development and/or tuber harvest.

The term "tuber yield" as used herein refers to the total weight of tubers of a plant or of a population of plants generally expressed in grams of fresh weight.

The term "tuber size" as used herein refers to the absolute width, height and length of a tuber. Beneficial tuber sizes include plant-average tuber sizes of about 80-160 grams per tuber. Mean tuber number for commercially valuable plants are about 8-12 tubers per plant.

The term "tuber skin colour" as used herein refers to the colour of the skin of a tuber after harvest as the result of anthocyanin accumulation in tuber skin tissues.

The term "eye depth" as used herein refers to the relative distance between the skin surface and the shoot primordium of a tuber.

The term "tuber shape" as used herein refers to the length/width ratio, to indicate the continuous variation from round, oval to long tuber shapes, as well as the height/width ratio, to indicate the continuous variation from cylindrical to the amount of flatness of a tuber.

The term "tuber flesh colour" as used herein refers to the colour of the interior of the tuber flesh after harvest as the result of the absence or presence of carotenoid compounds causing white or yellow flesh colour, respectively, as well as the absence of anthocyanins compounds causing red, blue, purple shades of flesh colour, irrespective of the presence of colour in patterns being partial or full.

The term "tuber taste" as used herein refers to the consumers appreciation by consuming a cooked potato tuber.

The term "tuber shelf life" and "tuber storage ability" as used herein are synonymous and refer to lack of changes in appearance of a tuber at storage.

The term "tuber dormancy period" as used herein refers to the time period between sowing and sprouting of a tuber, while sown at normal conditions.

The term "resistance to tuber dehydration" as used herein refers to a plant with shows less dehydration of the tuber than average at low humidity conditions (see shelf life).

The term "tuber starch content" as used herein refers to the starch weight over the total fresh weight of a tuber.

The term "tuber dry matter content" as used herein refers to the weight of the dry components of a potato divided over the total fresh weight.

The term "tuber cooking quality" as used herein refers to the continuous variation from firm to mealiness of a tuber after cooking.

The term "tuber frying quality" as used herein refers to the consumers appreciation of a tuber after frying.

The term "tuber chip making quality" as used herein refers to the consumers appreciation of a tuber after making chips.

The term "tuber uniformity" as used herein refers to the standard deviation of tuber traits, whereby a low standard variation refers to high uniformity and vice versa.

The term "cold sweetening resistance" as used herein refers to resistance of a tuber to produce glucose and/or fructose while stored at temperatures below 8° C.

The term "tetraploid" as used herein refers to a plant wherein each vegetative cell contains four sets of chromosomes (4n). The terms "fertile" and "fertility" broadly refer to the capacity to reproduce, i.e. to conceive and to produce offspring, preferably fertile offspring. Thus, the term fertility refers to individuals that can be crossed to produce fertile offspring in that the flowers, when pollinated produce berries that contain seeds which when sown result in a plant that itself carries fertile flowers, etc.

The term "fertile offspring" or "fertile seed" is defined herein as seed capable of growing into a flower-producing potato plant wherein flowers are male and female fertile. Thus, the term preferably refers to a plant or seed that when grown into a plant is capable of producing offspring as male and as female parent by virtue of the presence of fertile ovules and fertile pollen (i.e., both male and female flowers are fertile).

The term "fertile plant" is defined herein as a plant capable of producing fertile seed carrying berries. Preferably said berries each carry at least 5, more preferably at least 15-20, even more preferably at least 50 fertile seed, still more preferably between 50 and 500 seeds. Alternatively, a plant is said to be fertile when the number of seeds produced per berry is at least 10%, more preferably at least 30%, 40%, 50%, 60%, 70%, 80%, 90%, 100%, 150% 200% or more of the number found in berries of the diploid breeding clone RH89-039-16. The term also, or alternatively, refers to plant lines having more than 25%, preferably more than 90% fertile plants.

The term "self-compatible" refers to capacity to develop seeds in berries that are the result of self-pollination, self fertilization and producing fertile progeny.

The term "capable of being backcrossed/selfed/crossed and resulting in (self) fertile and self-compatible offspring" refers to the capability of producing one or more berries with seed as a result of backcrossing, selfing or crossing and wherein more than 60%, preferably more than 70%, 80%, 85%, 90% or more of said seed in said one or more berries is capable of developing into plants that are (self) fertile and self-compatible.

For other terms as used herein, reference is made to Allard, R. W. Principles of Plant Breeding, 2nd Edition, Wiley New York, 1999, and specifically to the Glossary therein.

DESCRIPTION OF THE PREFERRED EMBODIMENTS

The present inventors discovered that elite breeding lines for potato breeding can be successfully produced. Crossing of two elite breeding lines provides F1 hybrid seeds, such F1 hybrid seeds, when grown into plants, result in plants of superior agronomic performance. More importantly, all seeds are genetically essentially identical, meaning that, except for the occasional crossover or mutation event, all seeds are uniform.

The present inventors have discovered a method that allows the provision of elite potato breeding lines, which, when crossed mutually, provide uniform F1 hybrid potato seeds which, when grown into plants, result in plants having superior agronomic performance. The elite potato breeding lines may have complementary traits and, as a result of their homozygosity, the F1 plants grown from the F1 hybrid seeds are uniform, but when these F1 plants are subsequently selfed or cross-pollinated the resulting F2 plants will segregate for the various traits.

Thus, in contrast to the currently available true potato seeds (TPS) generated in the conventional ways of the prior art and harvested from berries in which every individual seed is genetically different from every other seed, the seeds obtained from crossing of the potato lines and elite potato breeding lines in accordance with aspects of the present invention are genetically essentially identical.

The TPS varieties of the prior art are derived from crosses between selected but heterozygous parents and hence variability is expected in plants and tubers. Hybrid potato breeding as proposed herein differs from the conventional production of TPS in that the present TPS are the result of the crossing of two pure breeding lines, resulting in uniform cultivars, whereas TPS varieties of the prior art are the result of open pollination or crossing between two genetically non-homozygous and often tetraploid breeding lines resulting in non-uniform cultivars.

Not only are the presently provided plants novel in that they combine a number of properties, heretofore never attained together in a single potato line, they also allow for novel and very advantageous breeding methods. Hence, the plants of the invention are an intermediate in the production of novel potato cultivars, which cultivars can be produced by methods as disclosed herein. The advantageous breeding methods allow for the elimination of many of the drawbacks of conventional potato breeding as indicated in hereinabove including the elimination of the time-consuming selection of clones to arrive at a new potato variety and the possibility to provide uniform hybrid potato seed. In addition, the novel plants and methods also allow for the elimination of drawbacks related to clonal propagation and production, including the possibility to eliminate high transportation costs and the clonal persistence of pests and diseases.

Novel Potato Plants
Parental Breeding Lines

The present invention provides potato plants that are essentially homozygous, diploid, vigorous, fertile and self-compatible.

Preferably the plants of the invention have fixed within their genome nucleic acid sequences encoding for genes that confer to the plant an agronomically desirable trait. Such nucleic acid sequences may be introgressions or transgenes derived from potato germplasm with agronomically desirable traits, preferably from diploid germplasm.

Essentially Homozygous

In breeding, plants are propagated by sexual reproduction, usually by crossing of selected parents with desirable traits to produce improved progeny. Progeny inherit genes for both desirable and undesirable traits from both parents. Repeated selection of meritorious individuals from each generation that will serve as parents of the next will conserve desired characteristics and eliminate undesirable ones. The ultimate parent in plant breeding is a purebred, a highly homozygous line that, when used in crossings with other purebreds results in offspring that is identical, both phenotypically and genotypically, within a single generation and between consecutive generations obtained from other crossings of the same parents. Purebreds, or pure inbreds, can be obtained by several generations of selfing or inbreeding (crossing of close relatives, such as brother to sister plants or offspring to parent (backcrossing)) each successive generation showing an increased degrees of genetic uniformity, or homozygosity. The use of homozygous inbreds as breeding parents results in offspring that is identical, both phenotypically and genotypically, within a single generation and between consecutive generations obtained from other crossings of those parents. Hence, the pure inbreds can be used repeatedly to produce the same offspring plants.

In potato, selfing and inbreeding results in severe inbreeding depression, or the expression of deleterious recessive genes, which expression is revealed by loss of vigour and loss of fertility. Hence, it has hitherto been impossible to produce homozygous pure inbreds in potato since until the present invention, high levels of homozygosity in potato with sufficient vigour could not be attained. The present invention now, for the first time, provides plants having a level of homozygosity that is above 25%, and preferably above 75% and that is combined with fertility, self compatibility and plant vigour.

Diploid

The plants of the present invention are diploid plants, in contrast to the commercial potato varieties, which are tetraploid. It should be noted that in plants of the present invention higher ploidy levels are expressly envisaged, since the diploid stage is used primarily during the development of the breeding lines. Once the purebreds have been established, the lines may be made tetraploid. Hence, plants of the invention may also be tetraploid. Tetraploid plants can be produced from tetraploid cells or tissue cultures, which in turn may be produced by duplicating the genome of diploid cells or tissue cultures by methods known per se, for instance by using oryzalin as described by Barandalla et al.

(Barandalla et al. Potato Research (2006) 49:143-154). Tetraploid plants may have the advantage that they provide higher yields.

Vigorous

Although commercial tetraploid potato varieties are fertile and self-compatible and vigorous in that they grow well, do not produce deformed plants, or fruits, but manifest as healthy plants with a high tuber yields, their selfed progeny shows serious inbreeding depression, that is, result in faint growing and low yielding plants with deformed tubers. Prior art diploid and essentially homozygous lines, such as those reported by Phumichai et al. as referred to herein, also grow only very poorly, and manifest as very weak and small plants, that have poor seed set. In fact, diploid potato plants resulting from inbreeding, and attaining homozygosity of at least 25% or 50% on the alleles are invariably weak growers.

The plants of the present invention are not weak and frail, and although they need not necessarily be as vigorous as present day commercial tetraploid varieties, they do not show inbreeding depression. Hence, within the context of the present invention, they are vigorous. Tuber formation exemplifies the vigour of the plants of the present invention. Although all commercial (tetraploid and seed-tuber derived) potato varieties produce large tubers, or at least tubers of sufficient size, prior art diploid lines and essentially homozygous plants produce only small tubers, which are, for instance, of no use in the production of potato chips or French fries. Prior art diploid lines and essentially homozygous plants produce also very few tubers such that the yield of tubers per plant is at least ten times lower than that of heterozygous diploids plants and commercial tetraploid potato varieties. In contrast, the plants of the present invention exhibit beneficial tuber formation characteristics, including tubers of beneficial size profile, and a tuber yield that may be at least 50% compared to the diploid heterozygous plants used as donors in the examples as described herein (D1, D2, and/or D3).

As was found herein, the tuber yield of the diploid F1's was on average 443 grams per plant, with values as high as 600 and 634 grams.

Backcrossing with the F1: "IVP08-06" yielded on average 155 and 209 grams, while backcrossing with the F1: "IVP08-07" yielded on average 209 and 259 grams.

The "pseudo F2's" yielded on average 172 and 332 grams per plant, and occasionally produced higher than the diploid F1's.

The F2's yielded on average 69 and 252 grams per plant. Several plants overlap with the yield values of the diploid F1s.

Fertile

The plants of the present invention—although essentially homozygous—are also fertile. That means that they can be used in breeding programs because their offspring will also be fertile.

Self Compatible

The plants of the present invention are self compatible. This feature is introduced in order to allow the selfing of plants and the production of homozygous lines. The preferred basis of the self compatibility is derived from the dominant S locus inhibitor gene (Sli) (Hosaka and Hanneman, 1998, Euphytica, 99: 191-197).

The essentially homozygous potato plants of the present invention have as an advantage that they can be crossed with other essentially homozygous potato plants whereby the hybrid offspring of said cross is essentially genetically uniform and will not segregate.

The present invention, in a preferred embodiment, provides essentially homozygous, diploid, vigorous, fertile, and self-compatible potato plants having agronomically desirable traits.

The novel potato plants of the invention are capable of:
being backcrossed to an essentially homozygous recurrent parent and resulting in (self) fertile and self-compatible offspring;
being selfed (self-fertilization of 1 offspring individual) and resulting in (self) fertile and self-compatible offspring;
being mutually crossed (fertilization between 2 offspring individuals) and resulting in (self) fertile and self-compatible offspring.

Plants according to the present invention include the line with breeders reference AGVD1, representative seeds of said line having been deposited on 23 Oct. 2009 with the NCIMB, Ferguson Building, Craibstone Estate, Bucksburn, Aberdeen, AB219YA, Scotland under accession number NCIMB 41663 and breeders reference AGVD1, which plant represents an F2 obtained by crossing a plant of parent IVP07-1001/4 (see Example 1), which is an essentially homozygous, diploid, fertile and self-compatible but non-vigorous potato line with a plant of parent D1, which is an elite diploid breeding clone that is essentially non-homozygous, and is not self-compatible, but which has the desirable agronomic trait of yellow flesh color and exhibits good cooking quality in that the flesh is not greying after cooking, and selfing the resulting F1 offspring plants. It is estimated that AGVD1 is about 50% homozygous, meaning that about 50% of the loci for which the parents differ are homozygous.

Plants according to the present invention also include the line with breeders reference AGVD2, representative seeds of said line having been deposited on 23 Oct. 2009 with the NCIMB, Ferguson Building, Craibstone Estate, Bucksburn, Aberdeen, AB219YA, Scotland under accession number NCIMB 41664 and under breeders reference AGVD2, which line represents an (F1×F1) line (or pseudo F2) obtained by crossing a plant of parent IVP07-1001/4 as indicated above with a plant of parent D1 as indicated above, and mutually crossing individual F1 offspring plants, that share the IVP07-1001/4 parent but have different individuals of the D1 parent. It is estimated that AGVD2 is about 25% homozygous for the loci for which the parents differ.

Plants according to the present invention also include the line with breeders reference AGVD3, representative seeds of said line having been deposited on 23 Oct. 2009 with the NCIMB, Ferguson Building, Craibstone Estate, Bucksburn, Aberdeen, AB219YA, Scotland under accession number NCIMB 41665 and under breeders reference AGVD3, which line represents a BC1 population obtained by crossing a plant of parent IVP07-1001/4 as indicated above with a plant of parent D1 as indicated above, and backcrossing the resulting F1 offspring plants with the IVP07-1001/4 parent. It is estimated that AGVD3 is about 75% homozygous for the loci for which the parents differ.

Plants according to the present invention also include the line with breeders reference AGVD17, representative seeds of said line having been deposited on 5 Oct. 2010 with the NCIMB, Ferguson Building, Craibstone Estate, Bucksburn, Aberdeen, AB219YA, Scotland under accession number NCIMB 41765 and under breeders reference AGVD17, which line represents an F3 population obtained by crossing a plant of parent IVP07-1001/4 as indicated above with a plant of parent D2 as indicated above, and backcrossing the resulting F1 offspring plants with the IVP07-1001/4 parent, followed by two steps of selfing. It is estimated that AGVD17 is >80% homozygous for the loci for which the parents differ.

A plant of the present invention can very suitably be used as a recurrent parent wherein additional agronomically desirable traits are introgressed by crossing, or introduced by other means such as by transgenic means. Once a number of agronomically desirable traits have been stacked into an essentially homozygous, vigorous, diploid, fertile and self-compatible plant according to the invention, that plant can be used as an elite breeding line for the production of commercial $F_1$ hybrid potato seed. Likewise, a second elite breeding line can be provided that can serve as the parent of opposite sex so that both plants can be crossed to produce the commercial $F_1$ seed of a novel potato variety.

The breeding of uniform hybrid seed depends on a number of technical conditions. Prerequisites to achieve uniform hybrid seed are that i) an initial introgression crossing can be made between an essentially homozygous, diploid, fertile and self-compatible plant and a plant that acts as donor for an agronomically desirable trait, that ii) a backcross can be produced between the offspring of that initial crossing and the essentially homozygous, diploid, fertile and self-compatible plant, and that iii) the offspring thereof can be selfed. Potato lines AGVD1, AGVD2 and AGVD3 exhibit these characteristics and individual plants of these lines can be used in additional introgression crossings, backcrossings and selfings to arrive at the elite breeding lines suitable for use as parents for commercial F1 hybrid seed that can be grown into hybrid potato plant of a new potato variety.

A highly preferred plant according to the present invention is a plant of line AGVD2 or an offspring plant thereof having all of the physiological and morphological characteristics of the plant of line AGVD2.

Another line deposited as example of embodiments of the present invention is AGVD17 (NCIMB 41765, deposited 5 Oct. 2010). The advantage of AGVD17 is that it is a highly homozygous line (>80% homozygous) combining vigour and fertility with a tuber yield of on average 300 grams (fresh weight) per plant. Individual plants of related populations even showed tuber yields of 500 grams per plant. These data were generated from field grown plants that were raised from seedlings. Potato plants raised from clones generally yield tuber weights that are 50 to 100% higher than plants raised from seedlings. Hence, the tuber yield expressed in grams of fresh weight from plants as claimed herein—when clonally propagated and raised from tubers and grown in clay soil under normal North Western European summer conditions—is expected to reach levels of at least about 1000 grams fresh weight per plant.

Thus, line AGVD17 demonstrates in particular the possibility to intercross individual elite lines of the present invention (i.e. that are self-compatible, fertile, and essentially homozygous) to arrive at the hybrid seed that is the aim of the present invention. Hence, another highly preferred plant according to the present invention is a plant of line AGVD17 or an offspring plant thereof having all of the physiological and morphological characteristics of the plant of line AGVD17.

Hybrids

Figure 1:
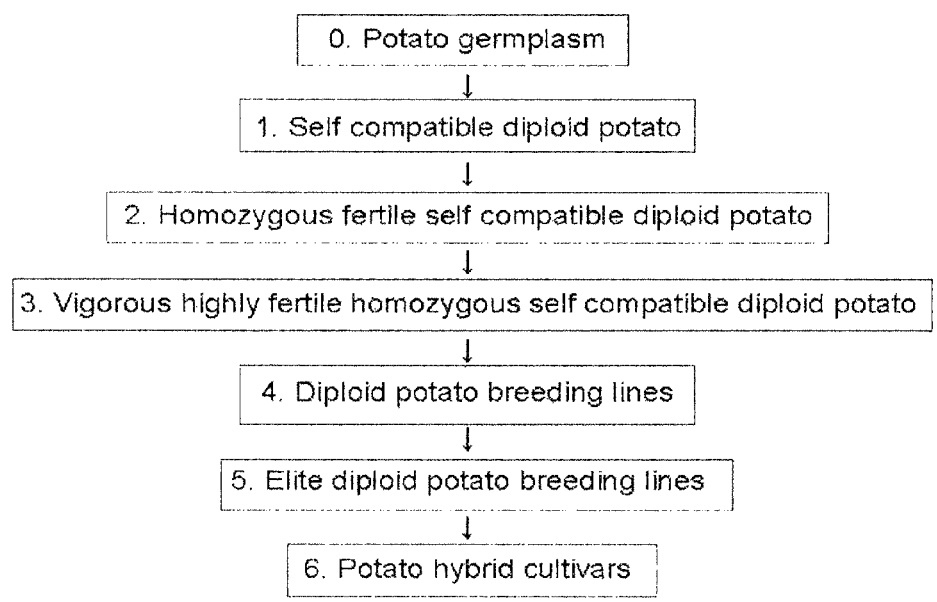
FIG. 1 shows a schematic presentation of a development scheme for the development of hybrid potato cultivars using the methods and plants of the present invention, wherein the various steps in obtaining commercial potato hybrids are indicated.

The hybrid plants of the invention are produced by a method of the invention as exemplified in FIG. 1. The hybrid plants of the invention are produced by crossing two essentially homozygous elite potato parental breeding lines comprising among them a number of agronomically desirable traits selected from the group consisting of insect tolerance, nematode resistance, disease resistance (including but not limited to resistance to Scab caused by *Streptomyces* spp, Powdery scab, *Rhizoctonia*, Silver scurf, *Phytophthora infestans*), herbicide tolerance, cold tolerance, drought tolerance, wet tolerance, tolerance to dry and wet rot, salinity tolerance, cold sweetening resistance and resistance to tuber dehydration. In addition to these agronomically desirable traits, the parental breeding lines may exhibit such characteristics as desired in specific use markets such as desirable tuber skin color, desirable tuber shape, desirable tuber flesh color, desirable tuber taste, desirable tuber starch content, desirable tuber dry matter content, desirable tuber cooking quality, or desirable tuber frying quality. In addition to such market-specific characteristics, the parental breeding lines, when crossed, preferably result in hybrids that exhibit such beneficial traits as beneficial growth rate, beneficial tuber yield, beneficial tuber size, beneficial tuber storage ability, beneficial tuber dormancy period, beneficial tuber shelf life, beneficial tuber chip making quality, and beneficial tuber uniformity.

The present invention now provides a set of potato plants or a set of potato plant lines, which plants or plant lines are: diploid (2n); essentially homozygous (preferably more than 60% on all alleles); self compatible; fertile; and vigorous. Hitherto it has proven impossible to provide the combination of all these features in a single potato plant (line). The set of potato plant of the invention can be used to produce novel varieties or cultivars.

The invention particularly relates to a set of at least 2 diploid (2n), essentially homozygous (preferably more than 60% on all alleles), self compatible, fertile, and vigorous plants that are crossable to produce hybrid varieties according to the invention.

Novel Method of Potato Seed Breeding

The provision of the novel potato plants now provides for the first time the attainment of the method of the invention.

The present inventors have generated potato plants that are essentially homozygous, diploid, vigorous, fertile and self-compatible and having fixed within their genome nucleic acid sequences encoding genes that confer to the plant an agronomically desirable trait derived from suitable diploid donor lines. The said nucleic acid sequences are the result of introgressions from potato germplasm having agronomically desirable traits. Conventionally, at least in most species other than potato, homozygous plants can in principle be obtained in as little as two generations by doubling of monohaploids generated from unfertilised generative cells such as egg or pollen cells by methods known as doubled haploid (DH) technology. This is not possible in potato, as the resulting plants have hitherto shown to be infertile, due to—what is considered—expression of recessive deleterious genes. The DH method was extensively tested by the present inventors, but was found unsuccessful.

The present inventors used the strategy of repeated selfing, backcrossing and crossing of potato germ plasm of a single self-compatible potato line and one or more self-incompatible potato lines harbouring agronomic traits. The homozygous plants of the present invention were obtained by continuous selfing of diploid potato plants and selection for fertile offspring (besides the inherent selection for self-compatibility). This is an entirely new approach, as in the prior art methods, plants are obtained by selection for agronomical traits, such as tuber formation or general growth characteristics of the offspring plants, not by selection for fertile offspring from selfings. Moreover, and unlike the prior art methods the procedures are performed using diploid plant lines, instead to of tetraploid plants. Unexpectedly, this radically new approach proved successful for obtaining increasingly homozygous, diploid offspring plants, that were self-compatible and fertile. In addition, when (out)crossed with plants of diploid lines harbouring beneficial traits, such as resistance or white tuber color, these traits could be introduced into the essentially homozygous germ plasm without loss of self-compatibility and fertility.

In essence the method for obtaining the plants is as follows:

Starting point is a diploid self-compatible potato line (examples of suitable lines have been deposited under depositors reference AGVD 1, AGDV 2, AGDV 3 and AGVD17). In general a line being self-compatible due to the presence of the Sli gene may be used as starting point. Plants of this diploid self-compatible line are selfed and seeds obtained from seed-carrying berries are sown and grown into offspring plants. Offspring plants carrying flowers are again selfed and seeds obtained from seed-carrying berries are again sown and grown into offspring plants. No, or at least little, attention is paid to the agronomical appearance of the plants at this stage. They may look withered and frail, with only a few flowers. Nonetheless, the selfing is repeated at least three times, but preferably 4 or 5 or even 6-8 times. In this manner a line of essentially homozygous, fertile, self-compatible, and diploid potato plants is obtained, essentially by selfing and selecting for plants that produce fertile offspring.

Next, an agronomically desirable trait is added to the essentially homozygous, fertile, self-compatible, diploid potato genotype by crossing a plant of that line with a plant of an unrelated essentially heterozygous diploid potato line, preferably a line containing an agronomically desirable trait. This essentially heterozygous line (which term merely reflects that the line is not an essentially homozygous line as used herein) functions as a donor for an agronomically desirable trait, in this case vigour.

The resulting hybrid is selfed and/or backcrossed to the self-compatible line while selecting for higher vigour. In this way, the vigour of the essentially homozygous, fertile, self-compatible, diploid potato plant line is enhanced and at the same time the line is agronomically improved. These steps will thus result in a vigorous fertile homozygous self-compatible diploid potato: The vigour may further be enhanced by crossing with other essentially heterozygous diploid potato lines, which additional lines serve as donors for additional agronomically desirable traits, followed by selfing and/or backcrossing to to the self-compatible line while selecting for these additional traits, which additional steps will result in the provision of diploid potato breeding lines.

In order to produce elite diploid potato breeding lines, the breeding value of the breeding lines is further enhanced by intercrossing, selfing and backcrossing while continuous selecting for the agronomically desirable traits provided to the breeding line, and by establishing lines that exhibit good combining abilities with other lines. Such combining abilities are evaluated by the use of experimental crosses.

Finally, hybrid potato cultivars can be produced by crossing individual elite diploid potato breeding lines that exhibit good combining abilities. The seeds resulting from this cross of homozygous parents are hybrid true potato seeds that are uniform.

Using the methods of the present invention, generally, around 7 to 8 selfing cycles will result in essentially homozygous plants, but the skilled artisan will understand that more generations of selfing may also be used. Also fewer generations, such as six generations may be used to provide essentially homozygous plants of the present invention. The number of backcross generation can even be reduced to three to reach more than 95% homozygosity when applying molecular genetic markers.

Essentially, the novel method of producing hybrid potato cultivars provides for the possibility to produce a new potato variety within about 5 years. A detailed process for the production of hybrid potatoes starting from AGVD17 (F3 line) is provided in Example 5. This line is >80% homozygous such that very few selfings are needed to obtain a plant that is about 95%-100% homozygous. In addition AGVD17 is already vigorous as defined herein.

The present invention now provides a method for producing a genetically homogenous or uniform true potato seed (TPS). This method is inter alia useful in a method of preventing transmittal of virus infections between potato generations, but also for overcoming many of the other problems associated with classical potato breeding, "seed" potato production and transport and cultivation. Moreover, the present parental material for production of hybrid seed can be maintained in the form of seed, and not in the form of vegetative material as is required by traditional TPS production.

The present invention provides in one aspect a method for producing a hybrid potato cultivar comprising the use of the deposited plant material provided herein as a starting material.

Alternatively, other essentially homozygous, diploid, fertile, vigorous and self-compatible plant lines different from the deposits referred to herein may be developed and the production of a hybrid potato cultivar can commence from that early stage level by using the teaching provided herein since the present inventors have demonstrated that this route, although laborious, is successful. Such an alternative breeding material is also vigorous, essentially homozygous, diploid, fertile and self-compatible.

As a first step, such an early stage development may comprise the provision of a plant of a first cultivated potato species (*Solanum tuberosum*) or a related crossable species (generally a tuber bearing *Solanum* species).

Next, said plant is developed into a line of self-compatible diploid potato plants, preferably a *Solanum tuberosum*. Diploid potato is usually self incompatible. Self-compatibility may suitably be introduced from related species (see for instance Hermsen, J. G. Th. 1978, Euphytica 27, 1-11).

The resulting line of self-compatible diploid potato plants is then developed into a homozygous fertile self-compatible diploid potato line. Homozygous diploids can be obtained by doubling haploids (Uijtewaal et al., 1987, Theor. Appl. Genet. 73, 751-78) by anther culture (Jacobsen and Sopory, 1977, Theor. Appl. Genet. 52, 119-123), by ovule culture or by repeated selfings (Phumichai & Hosaka, 2006, Euphytica 149, 251-258). The latter method was used for producing the homozygous fertile self-compatible diploid potato line that formed the basis of the vigorous plants as described herein.

Next, the homozygous fertile self-compatible diploid potato line is developed into a vigorous fertile homozygous self-compatible diploid potato line. The vigour may be enhanced by crossing with other diploid potato plants, selfing and backcrossing while selecting for higher vigour. It must be noted that high populations are needed and that even for some unrelated essentially heterozygous diploid potato lines that are used as donor of the agronomically desirable trait, very few self compatible plants may be found in a population of 1000 plants. Generally, such attempts are terminated, and only when about 10-50% of the offspring plants is self-compatible (such as in the case of D2 in Example 2 below) the donor line exhibits such good general combining ability that a successful introduction of the agronomical trait into the self-compatible lineage is foreseen.

Next, the vigorous, fertile, homozygous, self-compatible, diploid potato line is developed into a diploid potato breeding line. Most preferably, at least two separate vigorous fertile homozygous self-compatible diploid potato lines are produced and at least two distinct diploid potato breeding lines are developed. Such breeding lines comprise a high number of agronomically desirable traits. Agronomically desirable traits are introduced by crossing with other diploid potato plants, selfing and backcrossing while selecting for these traits. This breeding program may comprise testing for disease, such as whether the shoots or tubers are free of disease, or whether they are resistant for disease.

Next, the diploid potato breeding lines are developed into elite diploid potato breeding lines. This is accomplished by enhancing the breeding value by intercrossing, selfing and backcrossing while continuously selecting for agronomically desirable traits. At this stage experimental crosses are performed to evaluate general combining abilities. The diploid elite lines can now also be developed into tetraploid (4x) elite lines by methods known per se, such as by chemical treatment with e.g. colchicine, or by "spontaneous" doubling of the genome using tissue culture.

Finally, potato hybrid cultivars are produced from these elite diploid or tetraploid potato breeding lines by crossing of good combining breeding lines. The seeds obtained are hybrid true potato seeds that are uniform.

The method of the invention for producing a potato hybrid cultivar comprises the steps of producing a diploid potato breeding line. Said method comprises the steps of:

(a) providing a first potato plant, which first potato plant is a plant of a diploid, self-compatible and essentially homozygous potato line, preferably a plant of a vigorous fertile homozygous self-compatible diploid potato line, more preferably a diploid potato breeding line;

(b) providing a second potato plant of a potato line that may have any level of ploidy, preferably diploid, and/or any level of homozygosity wherein said second potato plant serves as a donor for an agronomically desirable trait which trait is to be introgressed into said essentially homozygous line of said first potato plant or at least in an offspring plant resulting from a crossing between said first and second plant, wherein said trait is selected from the group consisting of insect tolerance, nematode resistance, disease resistance (including but not limited to resistance to Scab caused by *Streptomyces* spp, Powdery scab, *Rhizoctonia*, Silver scurf, *Phytophthora infestans*), herbicide tolerance, rooting ability, cold tolerance, drought tolerance, wet tolerance, tolerance to dry and wet rot, salinity tolerance, growth rate, tuber development defects (e.g. misshapen or damaged tubers), tuber yield, tuber size, tuber skin color, eye depth, tuber shape, tuber flesh color, tuber taste, tuber storage ability, tuber dormancy period, tuber shelf life, resistance to tuber dehydration, tuber starch content, tuber dry matter content, tuber cooking quality, tuber frying quality, tuber chip making quality, tuber uniformity and cold sweetening resistance.

Following the provision of these two plants, the method then comprises the step of:

(c) cross-pollinating said first and second potato plant such that one of said parent plants produces seed-carrying fruits (berries) and collecting said seeds from said fruits to provide a hybrid offspring seed.

Seeds are then grown to plants and the plants that comprise the agronomically desirable trait from the donor plant are selected, either directly or following additional selfing and backcrossing steps, as is well known in the art of plant breeding. In these methods markers may be used to assist in the breeding process.

The hybrid offspring seed is preferably grown into a plant that is subsequently backcrossed a plant to the recurrent parent line The following steps are not essential to either of the above methods. However, these additional steps may either provide for the production of consumption tubers by growing the seeds of the invention and/or may provide for the production of new homozygous, self-compatible, diploid elite breeding lines that can serve as parents for the inclusion of yet further traits into an offspring generation. The plants of the invention are fertile and vigorous. These additional benefits are attained by the following further steps of:

(d) growing said offspring seed into a hybrid offspring potato plant, and (e1) harvesting tubers from said hybrid offspring potato plant to provide tubers carrying said trait, or (e2) selfing said hybrid offspring potato plant or backcrossing said hybrid offspring potato plant to a potato plant of said line of said first potato plant to provide further offspring plants carrying said trait and wherein said of offspring plants are increasingly homozygous following each backcrossing or selfing step.

Preferably said second potato plant used in the method described above is a hybrid offspring potato plant as defined in step (d) above and obtained by the method as described above. More preferably, said second potato plant used in the method described above is a hybrid offspring potato plant as defined in step (e2) above and obtained by the method as described above.

Preferably, said step (e2) comprises from 2 to 7 backcrosses using a plant of line AGVD1, AGVD2, AGVD3 or AGVD17 as the recurrent parent and testing offspring plants for the presence of the trait (e.g. in the form of the homozygous or heterozygous presence of alleles responsible for the trait), followed by one or two (or more) selfings, to provide an essentially homozygous plant that is genetically equal to a plant of population AGVD1, AGVD2, AGVD3 or AGVD17, but in which alleles responsible for the trait are heterozygously, preferably homozygously present. This plant has at least one additional allele not available in population AGVD1, AGVD2, AGVD3 or AGVD17.

The above method now provides a breeding process for the production of homozygous breeding lines or elite breeding lines based on the background of population AGVD1, AGVD2, AGVD3 or AGVD17, to which background successively additional alleles are added, thereby providing elite breeding lines wherein desirable traits are stacked.

The method of the present invention now for the first time provides for a method for preventing transmittal of virus infections between potato generations while at the same time also solving many of the other problems of the prior art related to breeding of new potato varieties and commercial production of potatoes for consumption. This has become possible through the provision of true potato seed, i.e. botanical seed, which seed can be grown to a potato plant that produces tubers for consumption, and which seeds are from a cross in which at least one of the parents is a plant of a diploid, self-compatible and essentially homozygous potato line, preferably said seeds are from a cross wherein both of the parents are plants from a diploid, self-compatible and essentially homozygous breeding line.

An important advantage of this new method is that, in this way, the transmittal of infection with a virus that is not spread through the gametes and seeds can effectively be prevented.

The present inventors now provide a method for further breeding for homozygous lines that are easy to handle, and which exhibit improved fertility and plant vigour when compared to prior art inbreds, while maintaining the self-compatibility and high level of homozygosity. It will be appreciated that—just as in tomato—a 100% homozygosity is not always needed to provide for an effective breeding program. This is not a problem as long the self-compatibility is maintained.

The genetic transfer of agronomically desirable or beneficial traits into a homozygous potato line has now for the first time been successfully shown.

Based on the means and methods provided herein, the skilled person will be able to successfully produce homozygous potato breeding lines based on his own germplasm. In addition, the skilled person will appreciate that means and methods are provided by which he is able to, for instance, stack additional traits into the presently provided self-compatible and essentially homozygous lines in order to establish a population of lines that are enriched for agronomically desirable traits and that can serve as germplasm for commercial breeding in their own right.

EXAMPLES

Example 1. General Description of the Breeding Procedure and Pedigrees

Many attempts were made to generate homozygous, fertile, self compatible diploid genotypes of potato without success. These attempts included the formation of doubled haploids, and the subsequent screening for fertile flowers. Several methods were employed like anther culture to regenerate haploid and eventually double haploid homozygous plants, repeated selfings to gradually increase the level of homozygosity in existing diploid germplasm and prickle pollination by using *S. phureja* as pollen donor to induce embryo formation from unfertilized egg cells. Especially the latter method was done at a large scale, by analyzing more than two million offspring but without the desired success. None of these tests resulted in vigorous self compatible plants.

An essentially homozygous potato line was obtained by multiple generations of selfing of plants of a line derived from public germplasm which plants have the self-compatibility controlling Sli gene (Phumichai et al. Euphytica (2006) 148: 227-234). These plants, designated "H" or IVP07-1001/4 herein, grew poorly, had very few flowers and each berry contained only few seeds. Moreover, the plants were very small (max 60 cm). The plants produced almost no tubers and those that formed were very small (average tuber weight about 5 grams/tuber). In all, the plants were of no value to commercial potato breeding, as they exhibited a plant weight and tuber yield that was less than 20% of that of diploid breeding clone RH89-039-16. The plants merely contained homozygous alleles on many of the loci in their genome, were self-compatible and diploid.

In the summer of 2008 plants of this IVP07-1001/4 line were crossed with different diploid donor lines (D1, D2 and D3, See for complete pedigree FIG. 2). D1 is early, has long sized oval tubers, light yellow flesh, and good cooking fries making quality and good cooking quality and was used as male parent (Table 6). The resulting progeny is referred to as F1(D1) in this example. Other F1 offspring plants were obtained in the similar way but using donor D2 as a female parent. D2 is an elite diploid breeding clone that is essentially non-homozygous, and is not self-compatible, but which has the desirable agronomic trait of early cooking, oval tubers, yellow flesh and good cooking chips making quality). This resulted in lines designated as F1(D2).

The above F1's were (D1) was selfed to produce an F2(D1). This line was deposited under breeders reference AGVD1. It is estimated that AGVD1 is about 50% homozygous, meaning that about 50% of the loci for which the parents differ are homozygous.

F1(D1) was crossed with F1(D2) to produce a pseudo F2. This line (F2(D1/2)) was deposited under breeders reference AGVD2. It is estimated that AGVD2 contains about 25% homozygous alleles originating from IVP07-1001/4.

The F1's were (D1) was also backcrossed with IVP07-1001/4 to produce a BC1's line. This line (BC1(D1) and BC1(D2)) was deposited under breeders reference AGVD3. It is estimated that AGVD3 is about 75% homozygous for the loci for which the parents differ.

Other F1 offspring plants were obtained in a similar way by using donor D3 as female parent. D3 is a diploid breeding clone with yellow flesh and with the resistance genes R3, H1, Gpa2, RXadg. This resulted in a line designated F1(D3).

Similarly as described above, F1(D3) was selfed to generate an F2(D3) and backcrossed with the Sli gene donor to generate BC1(D3) offspring.

F1(D1) was crossed with F1(D2) to produce a pseudo F2. This line (F2(D1/2)) was deposited under breeders reference AGVD2. It is estimated that AGVD2 is about 25% homozygous for the loci for which the parents differ.

F1(D1) was also backcrossed with IVP07-1001/4 to produce a BC1 line. This line (BC1(D1)) was deposited under breeders reference AGVD3. It is estimated that AGVD3 is about 75% homozygous for the loci for which the parents differ.

The BC1's were selfed in a winter nursery resulting in BC1S1 populations. Next summer (2010) the F2's, the pseudo F2's and the BC1S1's were sown in seed beds in a nursery and transplanted in small peat pots. In June 2010 the seedlings were transplanted to the field at a clay and at a sandy soil in The Netherlands. In total more than 15000 plants were grown from seedlings and selected for self compatibility and for good tuber quality and yield. Most F2 and BC1S1 populations showed a very low frequency of self-compatibility. Rare plants with reasonable good berry- and seed set were selected for progeny testing without further agronomic evaluations. Only two F2 populations, originating from the D2×H cross, showed about 25% self compatibility. For each of the most self-compatible populations maximally fifteen plants with the best tuber quality and quantity were selected for progeny testing.

Plants of the pseudo F2's showed much more vigour than the other populations, probably as these plants do not harbour any locus with homozygous alleles of the donor parents. One of these populations showed more than 50% self-compatibility. Similarly as described above, also maximally fifteen plants of the most self-compatible populations were selected for progeny testing.

In addition, crosses were made with self-compatible plants from the field as pollen donor on two to twelve plants of the donors D1-D19 (Example 3). After evaluation of the tuber quality and quantity only crosses with selected plants or their full sibs, in case of lack of sufficient numbers of crosses, were selected for progeny testing.

In this way, in each generation, plants are selected for self-compatibility and good agronomic performance. Seeds of the selfed berries of these selected plants are collected for further testing in order to generate homozygous lines. In addition, crosses of the selected plants with other diploid donors or other breeding lines are made to enhance the genetic variation. These F1 seeds are heterozygous and several rounds of inbreeding are needed to generate homozygous offspring with the desired traits.

In this way two generations of selections, selfings and crosses can be done per year. This process is even further enhanced by exploiting marker aided breeding by using diagnostic markers for specific traits and random markers to select for the recurrent parent genome. When elite parents have been obtained, derivatives of these lines can be made by two to three generations of backcrossing and two generations of selfing.

Example 2. Breeding Self Compatible Diploid Potato

1. Introduction

A common characteristic of diploid potato is self-incompatibility (SI); upon self-fertilisation no vital progeny is generated. The S-locus inhibitor gene (Sli) originating from *Solanum chacoense* has been described (*Euphytica* 99, 191-197, 1998) to inhibit this self-incompatibility and rendering diploid potato self-compatible (SC). Upon repeated selfings, close to homozygous self-compatible diploid potato clones have been generated (Genome 48, 977-984, 2005). The agricultural quality of these clones was very poor indeed reflecting a poor germination, plant growth, tuber quality and tuber yield.

2. Experiments 2.1 Materials

In order to develop self-compatible potato clones with much higher level of agricultural traits we crossed the Sli gene donor with various potato clones, designated: IVP97-079-9, IVPAA-096-18 and SH83-92-488. These clones are available at Dr. R. C. B. Hutten, Laboratory of Plant Breeding, Wageningen University, The Netherlands. As used herein, these clones are designated as clones D1, D2 and D3 resp. The progenies (F1) were selfed and backcrossed to the Sli gene donor generating F2 and BC1 populations, respectively. The BC1 was selfed to generate BC1S1 populations. All these crosses and self fertilisations were performed without any other selection than self compatibility of the plants.

2.2 Evaluation of Progenies in a Wintertrial

In a pilot experiment several random BC1 and F2 progenies were grown in a heated greenhouse with 16 hours artificial light in while outside temperatures were below zero for almost three months. We evaluated the self-compatible % as the number of plants with berries after hand pollination and the yield as the weight of tubers per plant (Table 2).

Results

The Sli donor is self-compatible (SC) and most of the F1 and BC1 plants were also self-compatible, while a minority of the F2 plants was self-compatible. The Sli donor showed an extremely low tuber yield, while the BC1 and one F2 was about 50% of the F1 tuber yield. The tuber yield of some BC1 plants was close to that of the F1 plants and some (unselected) F2 plants were better than the weakest F1 plants.

TABLE 2

Some characteristics of winter grown plants of a diploid potato breeding program to introduce the Sli gene.

| | # plants | compatibility frequency (%) | yield (gram per SC plant) average | variation |
|---|---|---|---|---|
| Sli donor | 2 | 100 | 22* | 0-43 |
| F1 (H × D3) | 9 | 89 | 443** | 258-634 |
| BC1 (H × (H × D1) | 49 | 81 | 206** | 0-524 |
| BC1 (H × (H × D2) | 64 | 72 | 237** | 28-543 |
| F2 selfed (H × D1) | 23 | 22 | 252** | 131-376 |
| F2 selfed (H × D2) | 20 | 25 | 69** | 0-201 |

*from tuber
**from seedling 2.3 Evaluations of Progenies in the Field

In the summer of 2010 progeny plants of F2 and BC1S1 populations were tested in the field to select self-compatible progeny plants with good agricultural performance (Table 3).

TABLE 3

Breeding scheme to introduce self-compatibility (SC) into diploid potato.

| | F1 (H × D) | F2: selfed (H × D) | | | | BC1S1: selfed (H × (H × D) | | | |
|---|---|---|---|---|---|---|---|---|---|
| P donor | plants (D × H) # | Populations tested # | plants in the field # | self compatible plants # | plants selected* # | populations tested # | plants in the field # | self compatible plants # | plants selected # |
| D1 | 33 | 15 | 2460 | ±50 | 7 | 38 | 2521 | <10 | 1 |
| D2 | 45 | 29 | 5598 | >500 | 55 | 24 | 1380 | <10 | 1 |
| D3 | 8 | 8 | 1602 | ±10 | 7 | | | | |

In bold the most promising materials are indicated.
*sufficient seedset
parents H = Sli Results We tested 52 F2 populations comprising 30 to 840 plants and 62 BC1S1 populations comprising 1 to 390 plants, in total 9660 F2 plants and 3901 BC1S1 plants resp. Most of the populations showed a weak plant growth and a low frequency of self-compatibility. Only two F2 populations derived from the D2 parent showed about 25% self compatible plants. The best plants of these populations were selected on the basis of tuber yield and tuber quality.

3. Conclusion

Only two out of the 52 F2 populations and none of the BC1S1 populations showed a reasonable level of self-compatibility. However, unexpectedly, the desired plants could be obtained, starting from material that would otherwise have been neglected by breeders. The main differences of the plants of the invention and those of the prior art are given in Table 4 below.

TABLE 4

Characteristics of the parental potato lines of the present invention proposed for the production of hybrid (true) potato seed.

| | Vigour | Ploidy | Tuber yield | Fertility | Self-compatibility. |
|---|---|---|---|---|---|
| Sli-gene donor (Phumichai et al. Euphytica (2006) 148: 227-234). | low | 2n | low | low/ intermediate | high |
| Diploid trait Donor (e.g. D1) | intermediate | 2n | intermediate | intermediate | low |
| Commercial variety | high | 4n | high | high | low |
| Lines of present invention | Intermediate/ high | 2n | Intermediate/ high | low/ intermediate | high |

Example 3. Development of a Molecular Marker Platform

Introduction

Numerous marker systems are available to support genetic research. For the present invention a molecular marker platform in potato was developed and used to evaluate the level of homozygosity versus heterozygosity in diploid potato.

Selection of Most Informative Sequences for SNP Assays

In order to analyse SNPs in potato, the Illumina standard GoldenGate protocol (Shen et al. 2005. Mutation Research 573:70-82) has been used previously (Anithakumari et al. 2010. Mol. Breeding, 26:65-75). This platform comprises 384 SNPs and was later expanded with another 768 SNPs. These 384 and 768 SNPs have been developed using EST sequences, which represent the mRNA without intron sequences. Since the present inventors have access to the first draft sequence of the potato genome (www.potatogenome.net) it was possible to compare the mRNA with the genomic DNA sequence including the intervening sequences. This comparison with the potato genome sequence was performed with the Basic Local Alignment Search Tool (BLAST; Altschul et al. 1990. J. Mol. Biol. 215: 403-410). This resulted in 538 and 1681 hits, respectively. The occurrence of multiple BLAST hits was considered to reflect paralogs or intron spanning sequences. These were removed from the initial collection of SNPs that were first developed for GoldenGate analysis (Anithakumari et al. 2010). This resulted in 279 and 453 unique BLAST hits representing the occurrence of only one copy in the potato genome sequence of Solanum tuberosum Group Phureja DM1-3 516R44 (CIP801092) as known hitherto (Potato Genome Sequencing Consortium, www.potatogenome.net).

From the total of 732 SNPs with unique BLAST hits only a few (31 cases, equally distributed over the 384 and 768 set) were omitted due to high level of sequence mismatches (3-6 SNPs within 101 bp). One mismatch should be expected and a second SNP was tolerated to be included in the SNP-spanning sequences selected.

For the present SNP design the minimal sequence length was set at 101 bp. Therefore 81 sequences were removed as they were shorter. The resulting 553 sequences have a length of at least 101 bp. A total of 100 sequences were then removed for having incomplete matches of only 35 up to 94 nucleotides within a scaffold of a doubled monoploid (DM-3 516R44; www.potatogenome.net). Also removed were sequences with introduced alignment gaps and sequences having other potential mismatch problems.

Though twenty-five sequences did not meet the criteria described above, they were kept as these were known to be highly informative in the GoldenGate SNP assays. These SNPs even allowed to discriminate between the five genotype classes that occur in tetraploids (Voorrips et al, EAPR-EUCARPIA congress "Potato Breeding after completion of the DNA Sequence of the Potato Genome", 27-30 Jun. 2010, Wageningen, the Netherlands, e-publication at edepot.wur.nl/143559, pg 42).

Finally, 515 sequences were selected. The final selection of 100 sequences was based on the known map position of 237 markers (out of the 515) on the potato genetic map (Anithakumari et al, 2010 and Van Os et al. Genetics 173: 1075-1087, 2006). The selected markers were evenly distributed over the 12 potato chromosomes including the most distal telomeric as well as centromeric markers and with a preference for SNPs that were heterozygous in clone RH (RH89-039-16; www.potatogenome.net), because clone RH is a progenitor of the material used in the present research. Or in other words, the alleles of clone RH are also present in material used in the present research (see Table 2 and FIG. 3).

Testing of Markers

The 100 SNP sequences selected as described above were used in a KASPar SNP genotyping system (KBioscience Ltd. Hoddesdon, UK; www.kbioscience.co.ukllab%20services/SNP%20Genotyping/genotyping_chemistry.html). The markers were tested on a set of 20 diploid potato genotypes (see FIG. 4) including the three diploid parents used in the present study and further on the donor of the Sli gene, clone 07-1004-1 (see also Example 2 herein above).

Results

All SNP sequences generated polymorphisms in the KASPar SNP genotyping system (see FIG. 4), corresponding to a 100% success rate. In total, 100 markers×20 genotypes were tested, comprising 2000 datapoints. We observed 29 missing data, which is less than 2%. As control, one genotype was tested twice whereby plant samples from different locations were used (FIG. 4, columns 4 and 7). All data were identical. These results illustrate that the KASPar SNP genotyping system is an efficient, reliable and reproducible marker platform for diploid potato. This indicated that The KASPar SNP genotyping system is efficient, reliable and reproducible for diploid potato.

All markers showed a high frequency of occurrence in the diploid potato germplasm used in this experiment. The heterozygote frequency in the germplasm by using these 100 markers ranged from 26% to 77%, while the Sli gene donor was 100% homozygous as is in accordance with expectations (Phumichai et al. 2005 Genome 48: 977-984).

The number of informative markers between the Sli donor and the three parents used in the present study was 54, 52 and 62 resp. This indicates that the KASPar SNP genotyping system is also informative for diploid potato.

Based on the above, it was concluded that the KASPar SNP genotyping system as described herein and based on the markers as developed herein is efficient, reliable and reproducible and very informative to describe the level of homozygosity/heterezygosity in diploid potato.

TABLE 5A

Sequences of 100 SNP markers in potato

| SNPs SNPID | SNPNum | AlleleY | AlleleX | Sequence | Sequence Identifier |
|---|---|---|---|---|---|
| PotSNP002 | 11940065 | G | C | ACCTGGTGCAGGCCT[C/G]CGTATTGATACGATT | SEQ ID NO: 1 |
| PotSNP011 | 11940098 | C | T | GACTGTGATTCGAAA[T/C]GTTTACCTATCTCTT | SEQ ID NO: 2 |
| PotSNP021 | 11940075 | C | T | TCGTAGAAATGACAT[T/C]TGGGGTGCTAGAGAT | SEQ ID NO: 3 |
| PotSNP026 | 11940044 | C | T | AGTTTCCAGCTGATG[T/C]TATTCTAGGAGACGA | SEQ ID NO: 4 |
| PotSNP032 | 11940037 | G | A | AGAGGCTCTTGAGGC[A/G]CAGCGAAAAGAGGAA | SEQ ID NO: 5 |
| PotSNp038 | 11940016 | C | T | TGGTGACGTTCATGT[T/C]GGACGTAATGCTTCT | SEQ ID NO: 6 |
| PotSNP043 | 11940036 | C | A | AGTATCTCCGTCCGA[A/C]TCACAGTCCTACTCT | SEQ ID NO: 7 |
| PotSNP045 | 11940094 | G | A | GGTGCTAAGATTCGC[A/G]TTGATGATTCACTAG | SEQ ID NO: 8 |
| PotSNP047 | 11940054 | C | T | CCAACACTGGAAAAA[T/C]TATGGAAGCAGAAAG | SEQ ID NO: 9 |
| PotSNP052 | 11940097 | C | T | GCTAGCATTAGAGCT[T/C]GCTAAGCGACTCAAT | SEQ ID NO: 10 |
| PotSNP055 | 11940021 | G | A | GCCTTGGAGTAAGAG[A/G]TTTTCTGTTTTGGGC | SEQ ID NO: 11 |
| PotSNP057 | 11940040 | C | T | GGATGTTCATCAACG[T/C]CGACTTCGACAAGCT | SEQ ID NO: 12 |
| PotSNP061 | 11940032 | C | T | ACAACCTGCAAGAGC[T/C]TTGCATCTGTTTAGT | SEQ ID NO: 13 |
| PotSNP068 | 11940023 | C | T | TACAATCATGATCCT[T/C]TTGCCTAATTGCCCT | SEQ ID NO: 14 |
| PotSNP072 | 11940005 | G | A | CTGAGCTAGTAGATC[A/G]ATCAAACGGTGCTCC | SEQ ID NO: 15 |
| PotSNP073 | 11940076 | G | T | GACTGTATGGACAGT[T/G]ATTGGGTCAGAGGAC | SEQ ID NO: 16 |
| PotSNP080 | 11940068 | C | T | AAGATGACGTGGAGT[T/C]CGGCACTGCGCCGTT | SEQ ID NO: 17 |
| PotSNP081 | 11940047 | C | T | GCCGCACAAGGTGCT[T/C]GCCGTCGATGTTAGC | SEQ ID NO: 18 |
| PotSNP083 | 11940033 | C | T | AGGTAGTGTTGCAAA[T/C]ACAATTAGAGGGTTG | SEQ ID NO: 19 |
| PotSNP089 | 11940062 | G | A | AAGTACATTTATGAG[A/G]AGATTAACAAGTGTT | SEQ ID NO: 20 |
| PotSNP099 | 11940092 | C | T | ACTGCTGGAACTGAG[T/C]TGAACAATGCTATTA | SEQ ID NO: 21 |
| PotSNP100 | 11940083 | C | T | GAGTGCCGGCAGCGT[T/C]ACAGATCCGACGATG | SEQ ID NO: 22 |
| PotSNP102 | 11940070 | G | A | TATGGCAGAGAAAGA[A/G]ATGGAGTATAGAGTG | SEQ ID NO: 23 |
| PotSNP1026 | 11940059 | G | C | TAAACTCCAACATAT[C/G]AACACAAATTAGTGC | SEQ ID NO: 24 |
| PotSNP1034 | 11940001 | G | A | TTCTACATCCTTCGC[A/G]GGCATTTTTGAGGAG | SEQ ID NO: 25 |
| PotSNP1049 | 11940051 | T | C | TTTGGGGAGGAACAC[C/T]TGTGCTTTAGAACTC | SEQ ID NO: 26 |
| PotSNP1057 | 11940022 | A | C | TGTCACTAAGAAAGC[C/A]CAAGAGGCAATGCAG | SEQ ID NO: 27 |
| PotSNP106 | 11940010 | G | T | GCAAGCTACTTGTTC[T/G]AAAGGACCTGCTACT | SEQ ID NO: 28 |
| PotSNP1072 | 11940027 | G | T | AGCGAGTTTGGATGC[T/G]GAGCTTTTGCAGTTA | SEQ ID NO: 29 |
| PotSNP1083 | 11940019 | C | T | TACAAAGTTCACTGC[T/C]GAGGAGGTCATGCAG | SEQ ID NO: 30 |
| PotSNP1105 | 11940041 | A | C | GATGAGGAAAGGCAC[C/A]GGCGGAGGTGTTGGA | SEQ ID NO: 31 |
| PotSNP1115 | 11940071 | T | C | CACCACCGTCCAAAC[C/T]GGTTTTGCCAATCGC | SEQ ID NO: 32 |

TABLE 5A-continued

Sequences of 100 SNP markers in potato

| SNPs SNPID | SNPNum | AlleleY | AlleleX | Sequence | Sequence Identifier |
|---|---|---|---|---|---|
| PotSNP1122 | 11940060 | T | C | GGTCCCTGAGCAAGG[C/T]AATCAACGAATTAGG | SEQ ID NO: 33 |
| PotSNP1139 | 11940004 | G | A | AGTCTCTACAAACCC[A/G]TGGTTTCGATCTTGA | SEQ ID NO: 34 |
| PotSNP116 | 11940058 | G | A | TAATGTGGTCGGCAC[A/G]CTGACGCTTGCTGAT | SEQ ID NO: 35 |
| PotSNP118 | 11940091 | G | A | AGATGCATTCTATGC[A/G]GAACCACAAAGATAT | SEQ ID NO: 36 |
| PotSNP120 | 11940082 | G | A | TTCGTGTTGCACTCA[A/G]CGATTCAGTTGGATG | SEQ ID NO: 37 |
| PotSNP121 | 11940099 | C | T | AGCTTGTGCTAATAG[T/C]TGTGCTGATTTTCTC | SEQ ID NO: 38 |
| PotSNP122 | 11940078 | G | A | TATGCAATCCCAGCC[A/G]ACATATCCGATCCAT | SEQ ID NO: 39 |
| PotSNP124 | 11940055 | G | A | TCATACTTCACATAT[A/G]TCAGAGTGGTCTGAT | SEQ ID NO: 40 |
| PotSNP130 | 11940050 | C | T | AGAGAAAAAGCTGT[T/C]GTTGTTGATGACGAG | SEQ ID NO: 41 |
| PotSNP134 | 11940080 | C | T | CGCGTATTTCCCTTA[T/C]TATAACTCGTTCTCT | SEQ ID NO: 42 |
| PotSNP138 | 11940052 | C | T | TTACATATGCAATAG[T/C]GGTGGTGATCTTTAT | SEQ ID NO: 43 |
| PotSNP152 | 11940077 | C | T | GAAGTTGTCTTACAT[T/C]GCTCTTGACTATGAA | SEQ ID NO: 44 |
| PotSNP162 | 11940074 | C | T | CTATGATGCATTTAG[T/C]TCATGGAGCAAACTT | SEQ ID NO: 45 |
| PotSNP165 | 11940009 | G | A | AGTTCCTTTTTCTCC[A/G]AGTTCTCAGACTCCG | SEQ ID NO: 46 |
| PotSNP178 | 11940026 | G | T | GAGGAATTGATGCGT[T/G]CTGAACTGGCACAGT | SEQ ID NO: 47 |
| PotSNP182 | 11940095 | G | A | ATACACAGGAAGGGT[A/G]AAGTGCTTCAAATTG | SEQ ID NO: 48 |
| PotSNP184 | 11940038 | G | A | TTTGACCATTCTTTC[A/G]GTCCTAGCTAACCAC | SEQ ID NO: 49 |
| PotSNP185 | 11940002 | C | T | AAGATAAGAAGAAAG[T/C]TAAGAGAACCAAGAT | SEQ ID NO: 50 |
| PotSNP194 | 11940064 | C | T | GGCCCACTTTCCACA[T/C]ATTCAATTTGGTCTC | SEQ ID NO: 51 |
| PotSNP205 | 11940042 | G | A | TCAACTCACCACTGG[A/G]TTTTACTCAAAATCA | SEQ ID NO: 52 |
| PotSNP213 | 11940096 | G | A | TAATATGTTGTGTCT[A/G]TAATTTTTGGGTCAT | SEQ ID NO: 53 |
| PotSNP220 | 11940013 | C | T | CATTAACCAAGGTTG[T/C]ATCGTTCGAGAGATC | SEQ ID NO: 54 |
| PotSNP229 | 11940056 | C | T | TCCTTTGTCATTGTA[T/C]GCCATGGAAGAAGCA | SEQ ID NO: 55 |
| PotSNP392 | 11940003 | T | A | GCTTTGTTTAAGAAC[A/T]GCCAGAAGAAGTTGC | SEQ ID NO: 56 |
| PotSNP401 | 11940012 | G | A | GCCTACGCGGCATGA[A/G]GATGTGGATATTGTT | SEQ ID NO: 57 |
| PotSNP402 | 11940072 | T | C | AAAGCTCAAATTAAA[C/T]GACGATGTTCAGGAA | SEQ ID NO: 58 |
| PotSNP423 | 11940020 | A | G | GGCCAACCAATTCCA[G/A]CGTCTTCTCCCAGAC | SEQ ID NO: 59 |
| PotSNP446 | 11940081 | C | T | AAAACCATTTGGTCT[T/C]GTTGATAATTCTGAG | SEQ ID NO: 60 |
| PotSNP458 | 11940069 | A | G | TACATAGCTCTACAA[G/A]CTTGGAAACATGTCA | SEQ ID NO: 61 |
| PotSNP470 | 11940043 | T | A | GACACAAAATTCATA[A/T]TGGCTGATACTTTGT | SEQ ID NO: 62 |
| PotSNP543 | 11940049 | T | A | GCAACTTGTCGTCGG[A/T]AAACTCGACTAGATT | SEQ ID NO: 63 |
| PotSNP567 | 11940014 | A | C | CTAGAAACAAAATCA[C/A]AATATAAGTTACATA | SEQ ID NO: 64 |
| PotSNP569 | 11940028 | G | A | GTTGTTTGCTTTGTT[A/G]TGCTGACTTATTGTA | SEQ ID NO: 65 |
| PotSNP573 | 11940034 | C | T | ATGCTTCTTGGTTGC[T/C]GTTTGTTTAGGCTCT | SEQ ID NO: 66 |
| PotSNP580 | 11940087 | T | C | AAATATGTTGTTCCA[C/T]TAGAAAAAAGAGTAA | SEQ ID NO: 67 |
| PotSNP586 | 11940088 | C | T | GTGAATACTGGTATC[T/C]TTCCAATTGAAGTCA | SEQ ID NO: 68 |
| PotSNP587 | 11940067 | C | T | AATATTCTTGTAGTA[T/C]ATATTGTCTAAAATC | SEQ ID NO: 69 |

TABLE 5A-continued

Sequences of 100 SNP markers in potato

| SNPs SNPID | SNPNum | AlleleY | AlleleX | Sequence | Sequence Identifier |
|---|---|---|---|---|---|
| PotSNP607 | 11940084 | T | C | CAACGATATCGAGAA[C/T]TATTGTTCTAAGGGA | SEQ ID NO: 70 |
| PotSNP626 | 11940045 | G | A | GCTGAAAGTAAAGAC[A/G]GTGTTCAACATCTTG | SEQ ID NO: 71 |
| PotSNP645 | 11940007 | T | G | CATGCAATTGTAATA[G/T]TATCAATGTTTGTTG | SEQ ID NO: 72 |
| PotSNP652 | 11940024 | T | C | TGCTCAAGCTGCCAA[C/T]GCTAATCCGCTTTAC | SEQ ID NO: 73 |
| PotSNP700 | 11940061 | G | A | CAAGATATATGCAGC[A/G]GAGTCCCTTCGAGCA | SEQ ID NO: 74 |
| PotSNP702 | 11940039 | A | T | TTATGGTTATGGTGG[T/A]GGAGGTTGGATTAAT | SEQ ID NO: 75 |
| PotSNP712 | 11940057 | C | G | GGGAGGGTGAAAATA[G/C]TCGAAAACGGGCAAC | SEQ ID NO: 76 |
| PotSNP713 | 11940073 | G | A | GATTGTTATCCTTCC[A/G]CCACCTCCAACAGAT | SEQ ID NO: 77 |
| PotSNP731 | 11940035 | A | G | CAACTTCCAGTCGTG[G/A]GAGTGGGGTTAACGG | SEQ ID NO: 78 |
| PotSNP753 | 11940046 | G | A | ATGGTGTCTCCAAGG[A/G]ACTATTACAGTCACT | SEQ ID NO: 79 |
| PotSNP759 | 11940090 | C | T | AACATCGATAGGACT[T/C]TGAAGGCCGCGGATG | SEQ ID NO: 80 |
| PotSNP766 | 11940089 | T | C | CTGCCACTGCGGCTG[C/T]AGGTTCTGCAGCTGC | SEQ ID NO: 81 |
| PotSNP775 | 11940079 | G | A | TGAAATGATTGGATT[A/G]TGACCCATAGTTTAG | SEQ ID NO: 82 |
| PotSNP796 | 11940025 | C | A | ATCTCTAAGTTGGGG[A/C]AACCCATAATTTCTA | SEQ ID NO: 83 |
| PotSNP827 | 11940053 | T | A | CGCTTGGGAAGAACC[A/T]TTCGGTCCAGTTTTG | SEQ ID NO: 84 |
| PotSNP834 | 11940006 | T | C | CCAATTCCGACGGCC[C/T]TCGTCGTTTCACCGC | SEQ ID NO: 85 |
| PotSNP853 | 11940066 | A | C | GGTCGACCATTGGGG[C/A]CCCGTAGAGGGTATA | SEQ ID NO: 86 |
| PotSNP866 | 11940048 | G | T | AAGGCGAATTCCGGT[T/G]CCCGAAATGGATCTC | SEQ ID NO: 87 |
| PotSNP893 | 11940011 | A | G | TCATTACATCAAAAT[G/A]TTTTATCAATGCCCA | SEQ ID NO: 88 |
| PotSNP908 | 11940100 | T | A | TGATCCATTTGGTCT[A/T]GACCAGTTCTTGACA | SEQ ID NO: 89 |
| PotSNP910 | 11940017 | T | A | TGCTGTGCTCCTTCT[A/T]TTCCTCATCTCTCAC | SEQ ID NO: 90 |
| PotSNP928 | 11940030 | A | T | TCATTCTCACTCTCC[T/A]GCTGAACAAGCCATT | SEQ ID NO: 91 |
| PotSNP947 | 11940015 | T | G | AAAAGACAAGAATCT[G/T]GTTCAGATTCTCCAG | SEQ ID NO: 92 |
| PotSNP948 | 11940063 | T | A | TGGGGAAAACTTAAT[A/T]TGACAGCCAAGGCGT | SEQ ID NO: 93 |
| PotSNP960 | 11940031 | C | T | GGTTTTGTGGACTGC[T/C]AACACTGAAAGATAC | SEQ ID NO: 94 |
| PotSNP964 | 11940029 | A | T | TTATTTCAATGAAGC[T/A]TCTGGTGGACGTTAT | SEQ ID NO: 95 |
| PotSNP982 | 11940085 | C | T | TCTGTGGTTTTTTCA[T/C]CACCTCCATCTTCAA | SEQ ID NO: 96 |
| PotSNP983 | 11940086 | G | A | TAAGATTAGTTCTAA[A/G]CTTAGCGCAGAAGAC | SEQ ID NO: 97 |
| PotSNP985 | 11940018 | A | G | GAGCTCTATAAGTGC[G/A]CCTGTTACTCCACCT | SEQ ID NO: 98 |
| PotSNP987 | 11940008 | C | A | GGGCTATGGTTGGTT[A/C]GGAAAAAAGGTGCAA | SEQ ID NO: 99 |
| PotSNP996 | 11940093 | C | T | GGATATTGGGTTCGT[T/C]CCATGATTCGTGGCA | SEQ ID NO: 100 |

TABLE 5B

List of PotSNPmarkers and their specific annotation for position on the SH and RH map of FIG. 3.

| Marker | Annotation |
|---|---|
| PotSNP072 | 1.1 |
| PotSNP834 | 1.2 |
| PotSNP645 | 1.3 |
| PotSNP1034 | 1.4 |
| PotSNP987 | 1.5 |
| PotSNP185 | 1.6 |

TABLE 5B-continued

List of PotSNPmarkers and their specific annotation for position on the SH and RH map of FIG. 3.

| Marker | Annotation |
|---|---|
| PotSNP392 | 1.7 |
| PotSNP165 | 1.8 |
| PotSNP1139 | 1.9 |
| PotSNP038 | 2.1 |
| PotSNP910 | 2.2 |
| PotSNP106 | 2.3 |
| PotSNP893 | 2.4 |
| PotSNP401 | 2.5 |
| PotSNP220 | 2.6 |
| PotSNP567 | 2.7 |
| PotSNP947 | 2.8 |
| PotSNP055 | 3.1 |
| PotSNP985 | 3.2 |
| PotSNP1083 | 3.3 |
| PotSNP423 | 3.4 |
| PotSNP1057 | 3.5 |
| PotSNP068 | 3.6 |
| PotSNP652 | 3.7 |
| PotSNP796 | 3.8 |
| PotSNP178 | 4.1 |
| PotSNP1072 | 4.2 |
| PotSNP960 | 4.3 |
| PotSNP061 | 4.4 |
| PotSNP569 | 4.5 |
| PotSNP083 | 4.6 |
| PotSNP964 | 4.7 |
| PotSNP928 | 4.8 |
| PotSNP573 | 5.1 |
| PotSNP184 | 5.2 |
| PotSNP702 | 5.3 |
| PotSNP731 | 5.4 |
| PotSNP043 | 5.5 |
| PotSNP057 | 5.6 |
| PotSNP1105 | 5.7 |
| PotSNP032 | 5.8 |
| PotSNP205 | 6.1 |
| PotSNP753 | 6.2 |
| PotSNP470 | 6.3 |
| PotSNP026 | 6.4 |
| PotSNP626 | 6.5 |
| PotSNP081 | 6.6 |
| PotSNP866 | 6.7 |
| PotSNP124 | 7.1 |
| PotSNP047 | 7.2 |
| PotSNP543 | 7.3 |
| PotSNP130 | 7.4 |
| PotSNP1049 | 7.5 |
| PotSNP229 | 7.6 |
| PotSNP712 | 7.7 |
| PotSNP138 | 7.8 |
| PotSNP827 | 7.9 |
| PotSNP1026 | 8.1 |
| PotSNP1122 | 8.2 |
| PotSNP700 | 8.3 |
| PotSNP853 | 8.4 |
| PotSNP089 | 8.5 |
| PotSNP948 | 8.6 |
| PotSNP194 | 8.7 |
| PotSNP116 | 8.8 |
| PotSNP002 | 8.9 |
| PotSNP102 | 9.1 |
| PotSNP587 | 9.2 |
| PotSNP1115 | 9.3 |
| PotSNP402 | 9.4 |
| PotSNP713 | 9.5 |
| PotSNP080 | 9.6 |
| PotSNP458 | 9.7 |
| PotSNP162 | 9.8 |
| PotSNP021 | 10.1 |
| PotSNP073 | 10.2 |
| PotSNP152 | 10.3 |
| PotSNP122 | 10.4 |
| PotSNP775 | 10.5 |
| PotSNP134 | 10.6 |
| PotSNP446 | 10.7 |
| PotSNP120 | 10.8 |
| PotSNP586 | 11.1 |
| PotSNP100 | 11.2 |
| PotSNP607 | 11.3 |
| PotSNP766 | 11.4 |
| PotSNP759 | 11.5 |
| PotSNP118 | 11.6 |
| PotSNP982 | 11.7 |
| PotSNP983 | 11.8 |
| PotSNP580 | 11.9 |
| PotSNP099 | 12.1 |
| PotSNP011 | 12.2 |
| PotSNP996 | 12.3 |
| PotSNP045 | 12.4 |
| PotSNP121 | 12.5 |
| PotSNP908 | 12.6 |
| PotSNP182 | 12.7 |
| PotSNP213 | 12.8 |
| PotSNP052 | 12.9 |

TABLE 6

Diploid potato genotypes used for SNP marker development and testing

| Nr. | Abbr. | code | Short description | reference |
|---|---|---|---|---|
| 1 | H | 07-1004-1 | Sli gene donor | 07-1004-1 is a progeny of the Sli-donor F1-1 as described in Phumichai et al. (2005) Genome Vol. 48: 977-984, Phumichai and Hosaka (2006) Euphytica 149: 251-258 and Phumichai et al. (2006) Euphytica 148: 227-234. |
| 2 | D1 | IVP97-079-9 | Parent 1 used in present research, early, long, Y (yellow flesh), Qcook | Examples 1, 2 and 4 herein; available from Ronald Hutten, Laboratory for Plant Breeding, Wageningen University. |
| 3 | D2 | IVPAA-096-18 | Parent 2 used in present research, early, Y, Qcook | Examples 1, 2 and 4 herein; available from Ronald Hutten, Laboratory for Plant Breeding, Wageningen University. |

TABLE 6-continued

Diploid potato genotypes used for SNP marker development and testing

| Nr. | Abbr. | code | Short description | reference |
|---|---|---|---|---|
| 4 | D3 | SH83-92-488 | Parent 3 used in present research, R3, H1, Gpa2, RXadg, Y | Examples 2 and 4 herein; available from Ronald Hutten, Laboratory for Plant Breeding, Wageningen University. |
| 5 | D4 | parent C | Parent of the C × E population | Anithakumari A. M. et al. (2010) Molecular Breeding 26(1): 65-75 |
| 6 | D5 | parent E | Parent of the C × E population | Anithakumari A. M. et al. (2010) Molecular Breeding 26(1): 65-75 |
| 7 | D3 | SH83-92-488 | Independent duplo of nr 3 | Van Os, H. et al. (2006) Genetics 173(2): 1075-1087 |
| 8 | D6 | RH89-039-16 | Used for genome sequencing | Van Os, H. et al. (2006) Genetics 173(2): 1075-1087; available from Ronald Hutten, Laboratory for Plant Breeding, Wageningen University |
| 9 | D7 | 3778-16 | Grp1, early, long (shape), Ro1 | Rouppe van der Voort et al. (1997) Mol Gen Genetics 255(4): 438-447 |
| 10 | D8 | IVP92-057-3 | early, long, Y, Qfry | Used for marker development in Example 3 |
| 11 | D9 | IVP98-082-14 | Long, Y, Qfry, H1, Qcook | Used for marker development in Example 3 |
| 12 | D10 | IVP02-089-5 | Early, long, Y, H1, Qcook, Zep (orange flesh) | Used for marker development in Example 3 |
| 13 | D11 | IVP05-113-1 | Early, y(white flesh) | Used for marker development in Example 3 |
| 14 | D12 | IVP05-122-24 | Qstarch, Y | Used for marker development in Example 3 |
| 15 | D13 | IVP06-142-12 | Wild species hybrid: *Phyt* avl | Used for marker development in Example 3 |
| 16 | D14 | IVP06-145-2 | Wild species hybrid: *Phyt* rch | Used for marker development in Example 3 |
| 17 | D15 | IVP06-148-13 | Round (shape), Qcook, Qfry | Used for marker development in Example 3 |
| 18 | D16 | IVP06-149-12 | Early, round, Zep, Y, spectacled, Qcook, blue anthocyans | Used for marker development in Example 3 |
| 19 | D17 | IVP06-155-9 | Wild species hybrid: *Phyt* tar | Used for marker development in Example 3 |
| 20 | D18 | IVP06-161-16 | Early, *Phyt* vnt1, round, Y, H1 | Used for marker development in Example 3 |
| 21 | D19 | IVPAA-134-16 | Early, round, y (white flesh) | Used for marker development in Example 3 |

Early: early flowering (short cycle); Qcook: good cooking quality; Qfry: good frying quality; *Phyt* indicates *Phytophthera* resistance genes Example 4. Development of Homozygous Diploid Potato Plants and Generation of Heterozygous F1 Hybrid Progeny Introduction The objectives of this Example were to develop homozygous diploid potato lines that are self-compatible (SC) and have good agronomic performance. A breeding programme to combine self-compatibility with good agronomic performance is described above in Example 2 above. The aim of the current experiment is to prove that homozygous diploid self-compatible potato genotypes can be generated by inbreeding and that diploid potato plants containing contrasting homozygous loci scattered over the potato genome can be crossed (are intercrossable) to generate heterozygous F1 hybrid progeny.

Materials and Methods

A self-compatible diploid homozygous potato genotype, that harbours the Sli-gene as described in the Examples above was crossed with two potato clones, designated D1 and D2 (see Examples 1 and 2) The F1 progenies were selfed and two F2 progenies were generated from two random SC F1 plants. Random self-compatible plants of these two F2 populations were selfed and per F2 population three F3 populations were tested for level of homozygosity and for segregation of SNP markers.

The 6 F2 plants were tested for ploidy level (by fluorescent quantitation of DNA) and were all found to be diploid.

A set of 36 markers was used on 265 individual F3 plants by applying the KASPar SNP genotyping system (see Example 3) covering all 24 chromosome arms of potato (see FIG. 5).

Results

Subsets of 35 to 56 plants from the six F3 populations, in total 265 plants, were tested with at least 24 informative markers per parent pair. In total 36 markers were used (see FIG. 5). For position of markers on the potato genome see Example 3, above. The Sli donor was 100% homozygous for these markers tested, while the D1 and D2 parents contained 20 and 19 loci resp. that were heterozygous out of the 24 informative markers tested per parent pair, while the other five and six loci resp. contained homozygous alleles originating from the from the donor parent (D1 or D2).

Six Homozygous F3 Plants

As expected, the F3 populations segregated for markers that were heterozygous in the F2 and not for markers that were fixed in the F2 (FIG. 5). The mean heterozygote level ranged from 84 to 95%, while that of individual plants ranged from 71 to 100% (Table 7).

TABLE 7

Homozygote frequencies (%) of six F3 populations

| F3 population | Donor parent | mean | range |
|---|---|---|---|
| 126 | D1 | 85 | 74-96 |
| 126B | D1 | 88 | 74-100 |
| 127 | D1 | 84 | 71-96 |
| 121 | D2 | 85 | 71-96 |
| 122 | D2 | 89 | 79-100 |
| 123 | D2 | 94 | 88-100 |

Three F3 populations of the D1×H and of the H×D2 crosses were analysed for frequency of homozygous loci based on the data in FIG. 5 as shown in Table 9.

These frequencies are expected giving the allele frequencies of the parents. There were six plants from three populations that were already 100% homozygous. These harboured mainly homozygous loci with Sli donor alleles. This is expected as the Sli donor harbours homozygous alleles, while the other parents contained one common allele with the Sli donor per heterozygous marker. So, Sli-donor derived alleles were abundant in all offspring populations. These six homozygous F3 plants, designated 122-34, 123-6, 123-20, 123-23, 123-24 and 126B-17, contained two, five, four, three, five and seven loci resp. with homozygous alleles from the donor parent. So, already in two selfed generations 100% homozygosity was reached for 24 marker loci representing 24 chromosome arms.

No Absolute Lethal Allele

It is often stated that repeated selfings in diploid potato will only result in weak plants due to inbreeding depression. This should be due to numerous deleterious alleles that reduce plant fitness, when these alleles are homozygously present. Therefore, we tested the segregation of 36 markers in the six F3 populations mentioned (see FIG. 5).

These markers, that were chosen because they are informative for the parent pairs used in this study, were also tested for the frequencies in 19 diploid potato genotypes, that were chosen as donors for the breeding programme (see Example 3, FIG. 4 and Table 9). If lethal alleles are present, then loci with homozygous alleles should be absent. Indeed, seven markers (designated PotSNP165, PotSNP205, PotSNP753, PotSNP 238, PotSNP 700, PotSNP 100 and PotSNP 607) did not show homozygous alleles that were different from the Sli-donor alleles in this diploid germplasm. Most of these markers were already fixed in the F2, most of them for Sli donor alleles as these were more abundant in the parents, but also examples were observed whereby the F3 population was fixed for the allele of the non-Sli parent (PotSNP753 in populations 126B and 127). Three of these seven markers (PotSNP205, PotSNP753 and PotSNP100) segregated in the F3 populations, whereby the PotSNP753 segregated normally and PotSNP205 and PotSNP100 showed distorted segregation. These may represent deleterious alleles. Only one plant with homozygous PotSNP100 donor alleles was identified. Without wishing to be bound by theory, it is believed that this may represent a very deleterious allele. As a single plant has been identified with a homozygous allele of the donor parent, this does not provide full proof for an absolute lethal allele.

F3×F3 Crosses

The 265 F3 plants tested were raised in an unheated greenhouse in the summer of 2010. In addition about 600 additional F3 plants were raised in the field with clay soil (see also Example 2). All these plants were from unselected F2 plants grown in a winter-nursery in The Netherlands (see Example 2). Crosses were made by applying pollen from greenhouse and field grown self-compatible plants on stigma of greenhouse grown self-compatible F3 plants. Only crosses were made between F3 plants with different great-grandparents (F3 plants of populations 121-123 crossed with 126-127). The greenhouse plants designated 126-24, 126-31, 126B-2 and 127-21 were successfully crossed as female self-compatible parent with a self-compatible F3 plant from population 123 as male parent. The female F3 plants were more than 80% homozygous, while the F3 plant in the field was not tested but the population mean homozygosity level was 94% with a range from 88 to 100%.

The parents of the F3×F3 crosses were compared for loci that are already fixed in the F3 populations (see Table 8). Ten homozygous loci on nine chromosomes were identified that were at least contrasting between one of the four female and the one male parent used for the F3×F3 crosses. As a consequence, the F1 hybrid progeny will be at least heterozygous for those contrasting loci. As each individual parent pair contained at least five contrasting loci, each individual progeny plant will harbour at least five contrasting chromosome regions.

TABLE 8

Contrasting fixed loci between the parents of the F3 × F3 crosses.

| Homozygosity level | % | chr | 126-24 86 | 126-31 80 | 126B-2 88 | 127-21 88 |
|---|---|---|---|---|---|---|
| Contrasting homozygous loci with F3 population 123 | PotSNP392 | 1 | x | | | |
| | PotSNP038 | 2 | x | x | | x |
| | PotSNP985 | 3 | | | x | x |
| | PotSNP1105 | 5 | x | x | x | x |
| | PotSNP753 | 6 | | | x | |
| | PotSNP124 | 7 | | | | x |
| | PotSNP162 | 9 | x | x | x | |
| | PotSNP021 | 10 | | | x | x |
| | PotSNP120 | 10 | x | x | x | x |
| | PotSNP213 | 12 | x | x | | |
| Total # | 10 | 9 | 6 | 5 | 6 | 6 |

The codes 126-24, 126-31, 126B-2 and 127-21 refer to individual F3 plants that were used as females in crosses with one field grown plant of the F3 population designated "123" (see above). The homozygosity level was calculated as the percentage of homozygous loci over all loci tested (FIG. 5). The "x" refers to homozygous markers that with contrasting alleles between the four female plants and the one plant of population 123.

Conclusions

It was found that after two generations of selfings homozygous diploid potato plants were obtained comprising alleles from both parents. Not a single marker out of 36 markers tested provided proof for a lethal allele. Furthermore, plants with more than 84% homozygous loci can be successfully crossed to obtain hybrid plants with at least five heterozygous chromosome regions. This means that hybrid seeds that are essentially uniform and that represent true potato seed have now been produced.

TABLE 9

Allele frequencies of genome wide SNP markers in diploid germplasm and F3 populations.

| | | allele frequencies | | | | | | | | | | | |
|---|---|---|---|---|---|---|---|---|---|---|---|---|---|
| | | diploid germplasm | | | | F3 from H × D1 | | | | F3 from H × D2 | | | |
| SNP marker code | chrom no | HH ** # * | HD # | DD # | HD % *** | HH # | HD # | DD # | HD % | HH # | HD # | DD # | HD % |
| PotSNP834 | 1 | 4 | 9 | 5 | 50 | 47 | 79 | 17 | 55 | 122 | 0 | 0 | 0 |
| PotSNP392 | 1 | 5 | 11 | 3 | 58 | 9 | 32 | 14 | 58 | 122 | 0 | 0 | 0 |
| PotSNP165 | 1 | 13 | 5 | 0 | 28 | 142 | 0 | 0 | 0 | n.i. | | | |
| PotSNP038 | 2 | 2 | 12 | 5 | 63 | 15 | 48 | 80 | 34 | 122 | 0 | 0 | 0 |
| PotSNP947 | 2 | 8 | 9 | 1 | 50 | 118 | 13 | 12 | 9 | 122 | 0 | 0 | 0 |
| PotSNP985 | 3 | 3 | 8 | 6 | 47 | 62 | 17 | 63 | 12 | 18 | 46 | 58 | 38 |
| PotSNP796 | 3 | 2 | 12 | 5 | 63 | 142 | 0 | 0 | 0 | 122 | 0 | 0 | 0 |
| PotSNP960 | 4 | 6 | 10 | 3 | 53 | 59 | 61 | 20 | 44 | n.i. | | | |
| PotSNP569 | 4 | 13 | 2 | 4 | 11 | n.i. | | | | 121 | 0 | 0 | 0 |
| PotSNP928 | 4 | 5 | 13 | 1 | 68 | 141 | 0 | 0 | 0 | 88 | 19 | 15 | 16 |
| PotSNP184 | 5 | 2 | 7 | 10 | 37 | 61 | 59 | 23 | 41 | 122 | 0 | 0 | 0 |
| PotSNP1105 | 5 | 2 | 12 | 5 | 63 | 140 | 0 | 0 | 0 | 19 | 40 | 62 | 33 |
| PotSNP205 | 6 | 13 | 6 | 0 | 32 | n.i. | | | | 91 | 27 | 3 | 22 |
| PotSNP753 | 6 | 9 | 10 | 0 | 53 | 28 | 20 | 91 | 14 | n.i. | | | |
| PotSNP626 | 6 | 9 | 8 | 2 | 42 | n.i. | | | | 122 | 0 | 0 | 0 |
| PotSNP081 | 6 | 12 | 6 | 1 | 32 | 142 | 0 | 0 | 0 | n.i. | | | |
| PotSNP124 | 7 | 8 | 9 | 2 | 47 | 85 | 0 | 55 | 0 | n.i. | | | |
| PotSNP229 | 7 | 7 | 11 | 1 | 58 | 56 | 0 | 0 | 0 | 15 | 37 | 69 | 31 |
| PotSNP138 | 7 | 9 | 10 | 0 | 53 | 55 | 0 | 0 | 0 | 121 | 0 | 0 | 0 |
| PotSNP1026 | 8 | 10 | 6 | 3 | 32 | n.i. | | | | 80 | 0 | 42 | 0 |
| PotSNP700 | 8 | 9 | 9 | 0 | 50 | 140 | 0 | 0 | 0 | 34 | 0 | 0 | 0 |
| PotSNP116 | 8 | 7 | 9 | 3 | 47 | 140 | 0 | 0 | 0 | n.i. | | | |
| PotSNP102 | 9 | 3 | 12 | 2 | 71 | 141 | 0 | 0 | 0 | 122 | 0 | 0 | 0 |
| PotSNP458 | 9 | 11 | 7 | 1 | 37 | n.i. | | | | 122 | 0 | 0 | 0 |
| PotSNP162 | 9 | 14 | 4 | 1 | 21 | 11 | 31 | 98 | 22 | n.i. | | | |
| PotSNP021 | 10 | 0 | 10 | 9 | 53 | 33 | 55 | 53 | 39 | 35 | 0 | 0 | 0 |
| PotSNP152 | 10 | 0 | 8 | 11 | 42 | 141 | 0 | 0 | 0 | 82 | 23 | 17 | 19 |
| PotSNP120 | 10 | 9 | 9 | 1 | 47 | n.i. | | | | 48 | 23 | 51 | 19 |
| PotSNP100 | 11 | 14 | 5 | 0 | 26 | 53 | 89 | 1 | 62 | n.i. | | | |
| PotSNP607 | 11 | 14 | 5 | 0 | 26 | n.i. | | | | 122 | 0 | 0 | 0 |
| PotSNP580 | 11 | 2 | 5 | 12 | 26 | 142 | 0 | 0 | 0 | 43 | 53 | 24 | 44 |
| PotSNP099 | 12 | 1 | 10 | 8 | 53 | 56 | 0 | 0 | 0 | 120 | 0 | 0 | 0 |
| PotSNP996 | 12 | 7 | 8 | 4 | 42 | 142 | 0 | 0 | 0 | n.i. | | | |
| PotSNP182 | 12 | 6 | 10 | 3 | 53 | n.i. | | | | 56 | 43 | 21 | 36 |
| PotSNP213 | 12 | 9 | 8 | 1 | 44 | 22 | 38 | 80 | 27 | n.i. | | | |
| PotSNP052 | 12 | 4 | 8 | 7 | 42 | 142 | 0 | 0 | 0 | 89 | 18 | 14 | 15 |

: number of plants; HH: homozygous Sli-donor locus; DD: homozygous donor locus; HD: heterozygous locus; % is percentage heterozygous plants, low numbers indicate high level of homozygosity in F3.

Example 5. Breeding Scheme for a Commercial Potato Variety

Starting from F3 materials obtained from crosses between an Sli donor and another diploid potato as described in Examples 2 and 4 above, a breeding scheme for producing commercial potato varieties is set out herein below. This scheme consists of a number of consecutive steps, which, in combination with the teaching as described herein, will allow the skilled person to arrive at a diploid or tetraploid hybrid potato variety that is as good as or preferable better then existing commercial hybrids and that can be multiplied much faster than conventional bred varieties within five years.

1. Definition of the Product Variety

Based on the invention as described herein, the production of a novel potato variety based on the production of commercial hybrids is not a matter of chance, but a directed design process, starting with the articulation of the product profile of the variety. Herein, the desired product profile (target product profile) for a specific market (chips potatoes, starch industry, consumption potato) must be defined. In addition, evaluation methods for the relevant traits in the product profile must be defined. Preferably, the presence of relevant traits is assessed by diagnostic markers. Such markers are well known in the art of conventional potato breeding.

2. Field Trials

Depending on the season at which the development process is started, a suitable trial field is selected. When starting in September or October, it is preferred that a suitable trial field located on the southern hemisphere is selected. Field trials may start with at least 2, preferably more F3 populations, selected from at least one, but preferably more crosses of a diploid Sli donor and another diploid potato genotype serving as a donor for an agronomical trait, preferably the trait of vigour, which F3 populations represent the diploid, fertile, self-compatible, essentially homozygous and vigorous potato lines of the invention as exemplified in Example 2. In addition to these F3 populations, F1 progenies are taken from at least two, preferably more selected F2 plants (as exemplified in Example 2 herein above) crossed with at least two, preferably more diploid potato genotypes that are different from the grandparents of the selected F2 plants. At least 50, preferably more individual plants of these F3 and F1 populations are then grown on the selected potato field and are selfed.

3. Evaluations and Selection

During the growth in the field, the frequency of self-compatible plants that carry berries within a period of 2-6 weeks following the onset of flowering is evaluated, and at least two, preferably more F3 and F1 populations with at least 10%, preferably more self-compatible plants are selected. Further, during the growing season, the agronomic characteristics as defined in the product profile of the self-compatible plants in the selected populations is evaluated. Leaf samples of all self-compatible plants of the selected populations are collected for DNA marker testing.

At the end of the growing season the tuber quality and quantity of the self-compatible plants in the selected populations is evaluated, and the DNA marker genotypes is assessed by using diagnostic and random markers. Based on this evaluation and assessment, at least the five, preferably more, self-compatible plants of each population are selected based on: (i) the combination of traits that is closest to the target product profile; (ii) the highest level of homozygosity, and (iii) with the maximum number of contrasting homozygous loci. The selected and selfed F3 and F1 plants provide F4 and F2 progenies, respectively, in the form of seeds.

4. Tuber and Seeds Harvest and Shipment

The tubers of the selected F3 and F1 plants as well as the F2 and F4 seeds in the berries of these selected plants are harvested at a period of at least at six weeks, preferably more, after flowering. The F4 seeds are collected for further field trials involving testing of the general combining abilities between F4 plants grown therefrom, and the F2 seeds provide additional gene pools for breeding and are collected for further field trials. Depending on the season and in order to safe time, the seeds may suitably be shipped to the northern hemisphere for growing in a greenhouse, provided that all phytosanitary regulations of the countries involved are met.

5. Tuber Storage and Evaluation

The tubers of the selected F1 and F3 plants are preferably stored in the region of cultivation to avoid undesired spread of pathogens and pests, and these stored tubers are evaluated for some relevant intrinsic tuber traits of the stored tubers as defined in the product profile.

6. Tuber Propagation and Evaluations After 1 Year

The tubers of the selected F1 and F3 plants are grown the next season, preferably in the same region as the original potato field to avoid spread of unwanted pathogens or pest. At least two, preferably more potato tubers are used per plot and preferably one preferably more replicates per clone are used. At least one, preferably more relevant commercial cultivars are included as controls. Side-rows with commercial cultivars are preferably included to avoid side effects. The relevant plant characteristics as defined in the product profile (e.g. cooking, frying, chips making, starch content, etc) are evaluated. Further evaluated are the tuber yield per plot as well as the intrinsic relevant tuber characteristics as defined in the product profile. Such evaluations are used for family characterisation and progeny selections. These trials are repeated each year, preferably at locations in both hemispheres to continuously select the ancestor properties of plants, grown in the field. At later stages, when hybrids are obtained that are tested for commercial introductions, the evaluation trials are extended to at least two, preferably more, replicates at plot sizes of at least one, preferably more $m^2$ and at two, preferably more, locations preferably in but not restricted to the target markets.

7. Testcrosses with F4 Seeds and Field Trials

Soon after the collection of the F4 progeny seeds of the selected selfed F3 plants, at least fifty, preferably more, of these seeds are sown. If needed, this sowing may occur in a heated greenhouse. The seedlings are preferably transplanted in small pots about 1 month after sowing and then transferred to the field in a suitable location some weeks thereafter. Evaluations and selections as described above are continued and at least two, preferably more selected F4 plants per population are testcrossed with at least two, preferably more, other selected F4 progeny plants of two, preferably more selected parents with maximum number of contrasting loci to produce test hybrids (F4×F4→hybrid). Additionally, at least two, preferably more selected F4 plants per population may be crossed with at least one, preferably more diploid genotypes with desirable characteristics or traits that are missing in the selected plants to enhance the genetic diversity of the breeding germplasm. Further, at least two, preferably more selected F4 plants per population may be selfed to produce F5 seeds. Still further, plant parts of at least two, preferably more selected F4 plants per population may be sterilised, in vitro propagated and treated with suitable chemicals (colchicine/oryzaline) to produce tetraploid F4 genotypes, and testcrosses are made with tetraploid F4 plants between the same parents as described above. In addition, similarly F2 progeny seeds are sown, transplanted and evaluated, crossed and selfed but not test/crossed The above breeding scheme is repeated each year whereby an incremental increase in plant traits as defined in the product profile is achieved. The evaluations of the tubers from testcrosses are instrumental to determine the general combining abilities of parents. General combining ability is defined herein as the average performance of a line in a series of crosses. For each market at least two, preferably more elite parent lines are achieved that will render commercial hybrid seeds. It is expected that in five years a diploid or tetraploid hybrid variety is generated that is as good as or preferable better then existing commercial hybrids and that can be multiplied much faster than conventional bred varieties.

The invention claimed is:

1. A diploid, fertile and self-compatible *Solanum tuberosum* potato line, said potato line comprising a plant having a tuber yield expressed in grams of fresh weight of at least 200 grams; wherein at least 50% of genomic loci in said plant are homozygous;

wherein said self-compatibility originating from *Solanum chacoense* and is referred to as S-locus inhibitor (Sli) gene, a copy of said gene is present in a plant of potato lines NCIMB accession number 41663, NCIMB accession number 41664, NCIMB accession number 41665, or NCIMB accession number 41765, representative seeds of said lines having been deposited with the NCIMB, Aberdeen, Scotland under breeders reference AGVD1, AGVD2, AGVD3, and AGVD17 respectively;

wherein at least 25% of the plants of said line produce seed-carrying berries, each carrying at least 5 seeds, and wherein at least 25% of the homozygous genomic loci in a plant of said line are from one or more of NCIMB accession number 41663, NCIMB accession number 41664, NCIMB accession number 41665, and NCIMB accession number 41765.

2. The potato line of claim 1, wherein said plant of said line, in addition to said tuber yield, comprises at least one agronomically desirable trait selected from the group consisting of insect tolerance, nematode resistance, disease resistance, herbicide tolerance, cold tolerance, drought tolerance, wet tolerance, tolerance to dry and wet rot, salinity tolerance, yellow flesh color and cold-sweetening resistance.

3. The potato line of claim 1, wherein said plant of said line, when mature, attains a fresh weight of the foliage and shoots of at least 500 grams.

4. A plant of the line according to claim 1.

5. A seed or tuber of the plant according to claim 4.

6. A method for producing a uniform hybrid potato seed, comprising:

(a) providing a first potato plant, which first potato plant is a plant of the first diploid, fertile, self-compatible and essentially homozygous *Solanum tuberosum* potato line according to claim 1, (b) providing a second potato plant, wherein said second potato plant is a plant of the second diploid, fertile, self-compatible and essentially homozygous *Solanum tuberosum* potato line according to claim 1, wherein said first and second plant contain at least 20% contrasting homozygous loci as determined by molecular marker analysis, and (c) cross pollinating said first and second potato plant and allowing one of said parent plants to produce berries with seeds and collecting said seeds from said berries to provide a hybrid off spring seed.

7. The method according to claim 6, wherein at least one of said first and second potato plants comprises at least one agronomically desirable trait selected from the group consisting of insect tolerance, nematode resistance, disease resistance, herbicide tolerance, cold tolerance, drought tolerance, wet tolerance, tolerance to dry and wet rot, salinity tolerance, yellow flesh color and cold-sweetening resistance.

8. The method of claim 6, wherein said first potato plant is a plant of potato line NCIMB accession number 41663, NCIMB accession number 41664, NCIMB accession number 41665, or NCIMB accession number 41765, representative seeds of said lines having been deposited with the NCIMB, Aberdeen, Scotland.

9. The method of claim 6, wherein said second potato plant is a plant of a second diploid, self-compatible and essentially homozygous *Solanum tuberosum* potato line, said second potato line comprising an additional agronomically desirable trait; and wherein said trait is insect tolerance, nematode resistance, disease resistance, herbicide tolerance, cold tolerance, drought tolerance, wet tolerance, tolerance to dry and wet rot, salinity tolerance, yellow flesh color or cold-sweetening resistance.

10. A seed of potato lines NCIMB accession number 41663, NCIMB accession number 41664, NCIMB accession number 41665, or NCIMB accession number 41765, representative seeds of said line having been deposited with the NCIMB, Aberdeen, Scotland.

11. A method for producing a hybrid potato seed wherein the method comprises crossing a first potato plant with a second potato plant and harvesting a hybrid potato seed resulting from said crossing, wherein said first or second parent potato plant is the potato plant of claim 4, and wherein said first and second parent potato have at least 20% contrasting homozygous loci as determined by molecular genetic marker analysis.

12. A method of producing a hybrid potato plant, said method comprising producing a seed according to a method of claim 6 and growing said seed into a potato plant.

13. A set of 2 homozygous diploid, fertile, self-compatible and essentially homozygous potato lines according to claim 1, wherein each of said lines differ from each other by having at least 20% contrasting homozygous loci as determined by molecular genetic marker analysis.

14. A method for producing a diploid, fertile, self-compatible and essentially homozygous *Solanum tuberosum* potato line, said potato line comprising plants having an average tuber yield expressed in grams of fresh weight of at least 200 grams per plant, comprising:
  (a) providing a first potato plant, which first potato plant is a plant of potato line NCIMB accession number 41663, NCIMB accession number 41664, NCIMB accession number 41665, or NCIMB accession number 41765, representative seeds of said line having been deposited with the NCIMB, Aberdeen, Scotland under breeders reference AGVD1, AGVD2, AGVD3, and AGVD17 respectively;
  (b) providing a second potato plant, wherein said second potato plant is a plant of a diploid or tetraploid *Solanum tuberosum* potato line, said potato line of said second potato plant having any level of homozygosity, said line of said second potato plant comprising plants having an average tuber yield expressed in grams of fresh weight of at least 200 grams per plant;
  (c) cross pollinating said first and second potato plant to provide seeds and collecting said seeds to thereby provide a hybrid offspring seed;
  (d) growing said hybrid offspring seed into a population of hybrid offspring potato plant and selecting from said population plants producing tubers at a yield expressed in grams of fresh weight of at least 200 grams per plant, and
  (e) selfing said hybrid offspring potato plant or backcrossing said hybrid offspring potato plant to at least one potato plant of potato line NCIMB accession number 41663, NCIMB accession number 41664, NCIMB accession number 41665, and NCIMB accession number 41765, for between 1 to 8 selfings or backcrosses, to thereby provide a diploid, fertile, self-compatible and essentially homozygous *Solanum tuberosum* potato breeding line, said potato breeding line comprising plants having an average tuber yield expressed in grams of fresh weight of at least 200 grams per plant; and wherein at least 50% of loci in the plant provided by step (e) are homozygous.

15. A tetraploid potato line produced by doubling the genome of the plant of claim 4.

16. A plant of the tetraploid potato line according to claim 15.

17. The potato line according to claim 1, wherein at least 75% of loci in said plant of said line are homozygous.

18. A method for producing a uniform hybrid potato seed, comprising:
  (a) providing a first potato plant of potato lines NCIMB accession number 41663, NCIMB accession number 41664, NCIMB accession number 41665, or NCIMB accession number 41765, representative seeds of said lines having been deposited with the NCIMB, Aberdeen, Scotland,
  (b) providing a second potato plant, wherein said second potato plant is a plant of a second diploid, fertile, self-compatible and essentially homozygous *Solanum tuberosum* potato line according to claim 1, wherein said first and second plant contain at least 20% contrasting homozygous loci as determined by molecular marker analysis, and
  (c) cross pollinating said first and second potato plant and allowing one of said parent plants to produce berries with seeds and collecting said seeds from said berries to provide a hybrid offspring seed.

19. A method for producing a diploid, fertile, self-compatible and essentially homozygous *Solanum tuberosum* potato line, said potato line comprising a plant having a tuber yield expressed in grams of fresh weight of at least 200 grams, comprising:
  (a) providing a first potato plant of potato lines NCIMB accession number 41663, NCIMB accession number 41664, NCIMB accession number 41665, or NCIMB accession number 41765, representative seeds of said lines having been deposited with the NCIMI3, Aberdeen, Scotland,
  (b) providing a second potato plant, wherein said second potato plant is a plant of a diploid Solarium *tuberosum* potato line, said potato line which may have any level of homozygosity, said line of said second potato plant comprising plants having an average tuber yield expressed in grams of fresh weight of at least 200 grains per plant;
  c) cross pollinating said first potato plant and said second potato plant to provide a seed and collecting said seed to thereby provide a hybrid offspring seed;
  (d) growing a multiplicity of said hybrid offspring seed into a population of hybrid offspring potato plants and selecting from said population plants producing tubers at a yield expressed in grains of fresh weight of at least 200 grams per plant, and (e) selfing said hybrid offspring potato plants or backcrossing said hybrid offspring potato plants to at least one potato plant of potato line NCIMB accession number 41663, NCIMB accession number 41664, NCIMB accession number 41665, and NCIMB accession number 41765, for between 1 to 8 selfings or backcrosses, and selecting for plants that produce fertile offspring wherein at least 90% of the plants produce seed-carrying berries, each carrying 5-500 seeds, to thereby provide a diploid, fertile, self-compatible and essentially homozygous *Solanum tuberosum* potato breeding line, said potato line comprising a plant having a tuber yield expressed in grams of fresh weight of at least 200 gram and wherein at least 50% of loci in the plant are homozygous.

* * * * *